United States Patent [19]

Deninno

[11] Patent Number: 5,698,526
[45] Date of Patent: Dec. 16, 1997

[54] STEROIDAL GLYCOSIDES

[75] Inventor: Michael Paul Deninno, Gales Ferry, Conn.

[73] Assignee: Pfizer Inc., New York, N.Y.

[21] Appl. No.: 652,477

[22] PCT Filed: Nov. 10, 1994

[86] PCT No.: PCT/IB94/00349

§ 371 Date: Jun. 19, 1996

§ 102(e) Date: Jun. 19, 1996

[87] PCT Pub. No.: WO95/18144

PCT Pub. Date: Jul. 6, 1995

Related U.S. Application Data

[63] Continuation of Ser. No. 174,100, Dec. 28, 1993, abandoned.

[51] Int. Cl.$^6$ .................................................. A61K 31/705
[52] U.S. Cl. .................................. 514/26; 514/173; 536/6
[58] Field of Search ........................... 514/26, 173, 6; 536/6.1, 4.1, 6; 549/344

[56] References Cited

U.S. PATENT DOCUMENTS 4,265,886  5/1981  Pegel ............................................ 514/26

OTHER PUBLICATIONS

Protective Groups in Organic Synthesis; Greene, T.W., 1981, Wiley and Sons Inc., pp. 16, 39–50, 61, 69, 70, and 72–82, Feb. 1982.

*Primary Examiner*—C. Warren Ivy
*Assistant Examiner*—Garth M. Dahlen
*Attorney, Agent, or Firm*—Peter C. Richardson; Gregg C. Benson; A. Dean Olson

[57] ABSTRACT

This invention relates to certain steroidal glycosides of Formula I

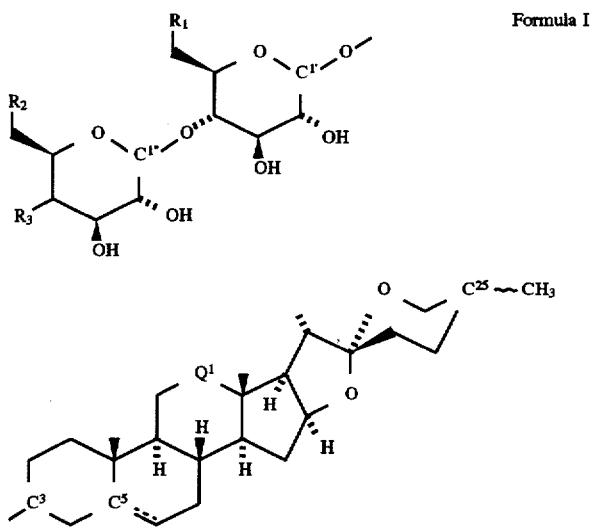

wherein the values for the variables are described herein, which are useful as hypocholesterolemic agents and anti-atherosclerosis agents and certain protected intermediates useful in the preparation of said steroidal glycosides.

26 Claims, No Drawings

1

STEROIDAL GLYCOSIDES

This application was filed under 35 U.S.C. §371 based on PCT/IB94/00349, which was filed on Nov. 10, 1994 which is a continuation of U.S. application Ser. No. 08/174,100 which was filed on Dec. 28, 1993 and is now abandoned.

BACKGROUND OF THE INVENTION

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficiency. Thus, the effective hypocholesterolemic dose of these materials is excessive, typically 18–24 grams of formulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of non-useful chemical substances. Due to the variations in composition, it is difficult to set a standard dosage or predict the impurities present. Thus, such extracts are not well suited for use by humans. Furthermore purification of these extracts would be expensive. As an alternative certain synthetically produced, pure "sapogenin-derived" compounds e.g., substances compounded from spirostane, spirostene or sterol-derived compounds depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive amounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, Iu. K. Vasilenko, G. M. Gorianu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyramine. PCT publication WO 93/07167 discloses several steroidal glycosides in particular 3-O-(5-C-hydroxymethyl-L-arabino-hexopyranosyl)-tigogenin and 3-O-(5-C-hydroxymethyl-L-arabino-hexopyranosyl)-diosgenin and their use in the control of hypercholesterolemia.

Recently commonly assigned PCT publication WO 93/11150 has disclosed a number of steroidal glycosides including 11-ketotigogenyl-beta-O-cellobioside, hecogenin-beta-O-cellobioside, diosgenin-beta-O-cellobioside and their use as antihypercholesterolemic agents. Also commonly assigned PCT publication WO 94/00480 the disclosure of which is hereby incorporated by reference, discloses a variety of steroidal glycosides and their use as antihypercholesterolemic agents.

Although the hypocholesterolemic compounds described above make a significant contribution to the art there is a continuing search in this field of art for improved hypocholesterolemic pharmaceuticals.

SUMMARY OF THE INVENTION

This invention is directed to steroidal glycosides, particularly spirostanyl glycosides, that are useful as hypocholesterolemic agents and antiatherosclerosis agents. The compounds of this invention have the formula

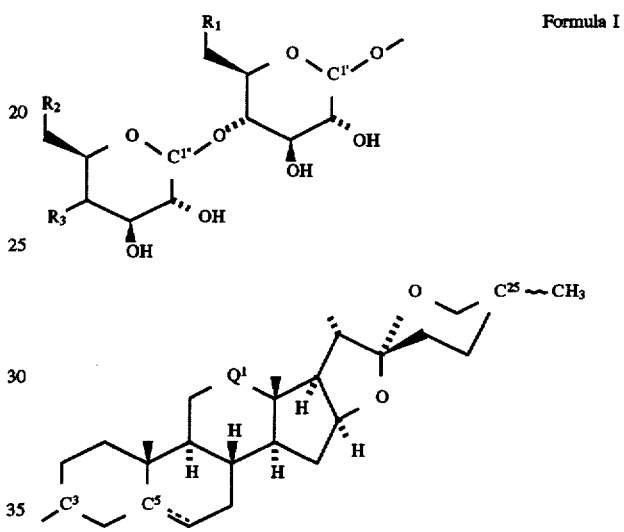

Formula I and the pharmaceutically-acceptable salts and hydrates thereof
wherein
$Q^1$ is carbonyl, methylene,

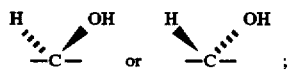

$R_1$, $R_2$, and $R_3$ are each independently hydrogen, hydroxy, halo, amino, azido, $(C_1-C_6)$alkoxy$(C_1-C_6)$alkoxy or —Z—$R_4$;

Z for each occurrence is independently —NH—C(=O)—, —O—C(=O)—, —O—C(=O)—N($R^5$)—, —NH—C(=O)—N($R^5$)— or —O—C(=S)—N($R^5$)—;

$R_4$ for each occurrence is independently aryl, aryl$(C_1-C_6)$alkyl, $(C_2-C_4)$alkenyl, $(C_1-C_6)$alkyl, cyclo$(C_3-C_7)$alkyl or cyclo$(C_3-C_7)$alkyl$(C_1-C_6)$alkyl; each $R_4$ optionally mono-, di-, or tri-substituted independently with halo, $(C_1-C_4)$alkyl, hydroxy, phenoxy, trifluoromethyl, nitro, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, dimethylamino, mono-or di-$(C_1-C_4)$alkylaminocarbonyl, $(C_1-C_4)$alkylcarbonyl, $(C_1-C_4)$alkoxycarbonyl, pyrrolidinylcarbonyl wherein aryl is carbon-linked and is phenyl, furyl, thienyl, pyrrolyl, oxazolyl, isoxazolyl, oxadiazolyl, thiazolyl, isothiazolyl, benzothiazolyl, thiadiazolyl, pyrazolyl, imidazolyl or pyridyl; and $R_5$ for each occurrence is independently hydrogen, $(C_1-C_4)$alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with $(C_1-C_4)$alkoxycarbonyl;

with the proviso that $R_1$, $R_2$ and $R_3$ are not all hydroxy.

A first group of preferred compounds of Formula I consists of those compounds wherein $R_1$, $R_2$ and $R_3$ are each independently hydroxy or —Z—$R_4$, Z is —O—C(=O)—N($R_5$)— and $R_5$ is hydrogen. Especially preferred within this group are compounds wherein the $C^{1'}$ anomeric oxy is beta, the $C^{1''}$ anomeric oxy is beta, $R_3$ is alpha, the $C^5$ hydrogen is alpha, $C^{25}$ is (R), the $C^3$ oxy is beta, $Q^1$ is carbonyl and $R_1$ is hydroxy. Particularly preferred compounds within this especially preferred group are compounds wherein $R_2$ and $R_3$ are —Z—$R_4$ and $R_4$ is 2,4-difluorophenyl, phenyl, 2-fluorophenyl, 2-methylphenyl, 2-thienyl-methyl, 2-methoxycarbonyl-ethyl, thiazol-2-yl-methyl or 2-methoxycarbonyl-butyl. Other particularly preferred compounds within this especially preferred group are compounds wherein $R_3$ is hydroxy, $R_2$ is —Z—$R_4$ and $R_4$ is 2,4-difluorophenyl or 2,6-dichlorophenyl.

A second group of preferred compounds of Formula I consists of those compounds wherein $Q^1$ is carbonyl, $R_1$ is hydroxy, hydrogen, halo, azido, or $(C_1-C_6)$alkoxy$(C_1-C_6)$alkoxy, $R_2$ is hydrogen, halo, azido, or $(C_1-C_6)$alkoxy $(C_1-C_6)$alkoxy, $R_3$ is —Z—$R_4$, Z is —O—C(=O)N—($R_5$)— and $R_5$ is hydrogen. Especially preferred within this second group are compounds wherein the $C^{1'}$ anomeric oxy is beta, the $C^{1''}$ anomeric oxy is beta, $R_3$ is alpha, the $C^5$ hydrogen is alpha, $C^{25}$ is (R) and the $C^3$ oxy is beta. A particularly preferred compound within this group is a compound wherein $R_1$ is hydroxy, $R_2$ is hydrogen and $R_4$ is 2-fluorophenyl.

A third group of preferred compounds of Formula I consists of those compounds wherein $Q^1$ is carbonyl, $R_1$, $R_2$ and $R_3$ are each independently hydroxy or —Z—$R_4$, Z is —O—C(=O)— and $R_4$ for each occurrence is independently $(C_1-C_6)$alkyl, phenyl or phenyl mono-, di- or tri-substituted independently with $(C_1-C_6)$alkoxy, halo or nitro.

A fourth group of preferred compounds of Formula I consists of those compounds wherein $Q^1$ is carbonyl, $R_3$ is hydroxy, at least one of $R_1$ and $R_2$ is —Z—$R_4$, Z is —NH—C(=O)— and $R_4$ for each occurrence is independently $(C_1-C_6)$alkyl.

A fifth group of preferred compounds of Formula I consists of those compounds wherein $Q^1$ is carbonyl, $R_3$ is hydroxy and $R_1$ and $R_2$ are each independently halo or azido.

Protected intermediates of the above Formula I compounds include compounds of Formula IIA

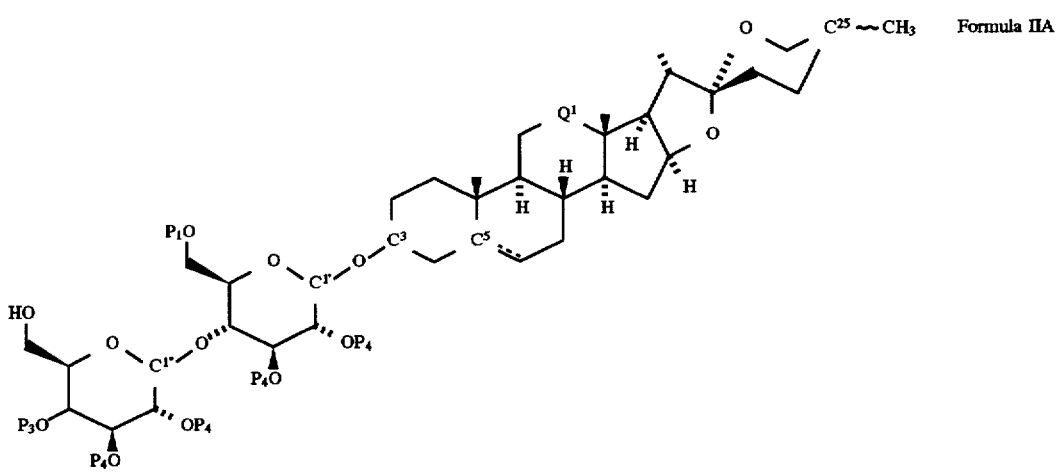

Formula IIA wherein $Q^1$ is carbonyl, methylene,

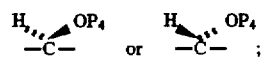

$P_4$ is an alcohol protecting group; and $P_1$ is hydrogen and $P_3$ is an alcohol protecting group or $P_3$ is hydrogen and $P_1$ is an alcohol protecting group, Preferred compounds of Formula IIA consist of those compounds wherein the alcohol protecting group is acetyl or chloroacetyl.

Other protected intermediates of the above Formula I compounds include compounds of Formula IIB

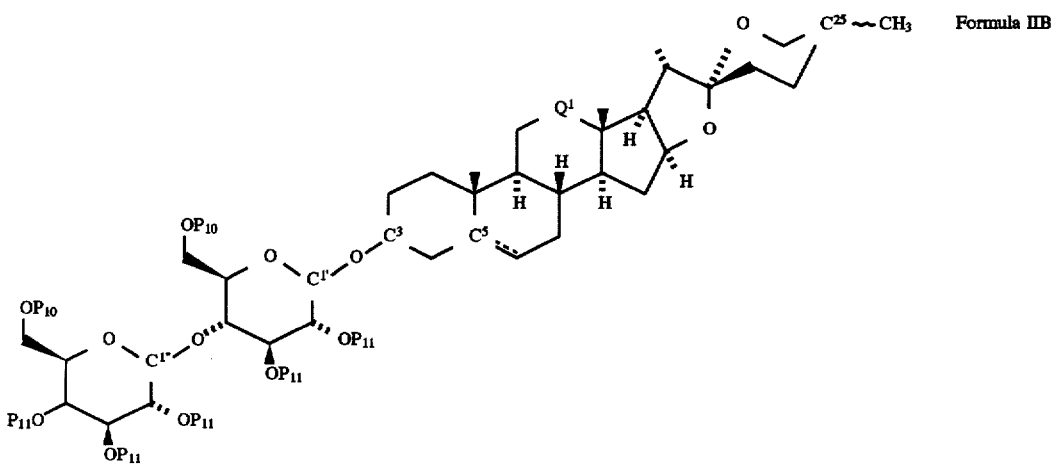

wherein

Q¹ is methylene, carbonyl,

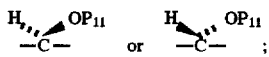

$P_{10}$ is a silyl protecting group; and $P_{11}$ is an alcohol protecting group that is different from $P_{10}$.

Preferred compounds of Formula IIB consist of those compounds wherein the alcohol protecting group is acetyl and the silyl protecting group is t-butyldiphenylsilyl, triisopropylsilyl or t-butyldimethylsilyl.

Other protected intermediates of the above Formula I compounds are compounds of Formula IIC Yet another aspect of this invention is directed to a method for treating hypercholesterolemia or atherosclerosis in a mammal by administering to a mammal suffering from hypercholesterolemia or atherosclerosis a hypercholesterolemia or atherosclerosis treating amount of a Formula I compound.

This invention is also directed to pharmaceutical compositions for the treatment of hypercholesterolemia or atherosclerosis in mammals which comprise a compound of the Formula I and a pharmaceutically acceptable carrier.

The compounds of Formula I are herein defined as the single enantiomer having the absolute stereochemistry depicted in Formula I.

By alcohol protecting group is meant a conventional alcohol protecting group known to those skilled in the art such as is used to protect a hydroxy group. Such alcohol

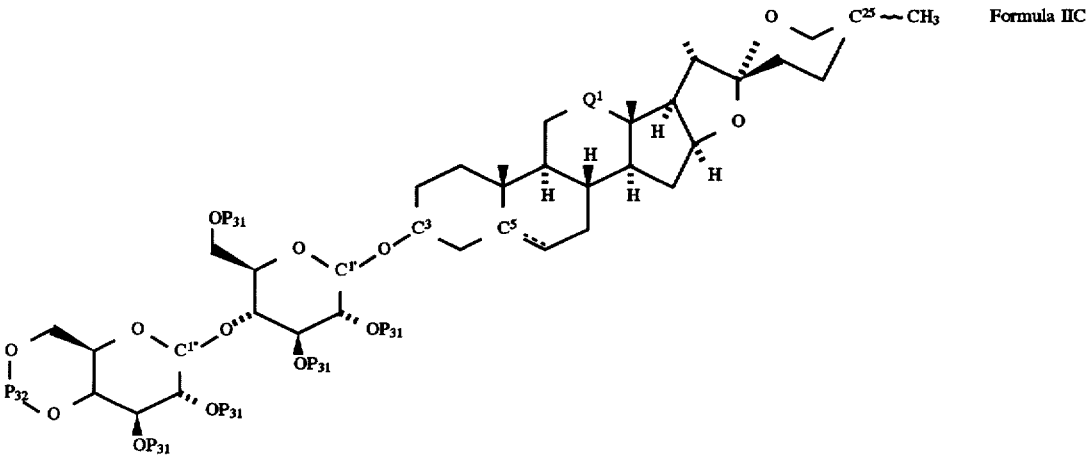

wherein

Q¹ is methylene, carbonyl,

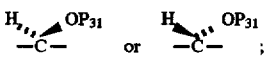

$P_{31}$ is an alcohol protecting group; and $P_{32}$ forms a cyclic protecting group for a 1,3 diol.

Preferred compounds of Formula IIC consist of those compounds wherein $P_{31}$ is acetyl or chloroacetyl and $P_{32}$ is benzylidene or paramethoxybenzylidene.

protecting groups are described in T. W. Greene, *Protective Groups in Organic Synthesis*, John Wiley & Sons, New York, N.Y., 1991, 2nd Edition, which is hereby incorporated by reference (e.g., see pages 10–13) and include for example, esters such as formyl, ($C_1$–$C_{10}$)alkanoyl optionally mono-, di- or tri-substituted with ($C_1$–$C_6$)alkoxy, halo, aryl, aryloxy or haloaryloxy; aroyl optionally mono-, di- or tri-substituted on carbon with halo, ($C_1$–$C_6$)alkyl, ($C_1$–$C_6$) alkoxy wherein aryl is phenyl, 2-furyl etc; carbonates; sulfonates; and ethers such as benzyl, paramethoxybenzyl, methoxymethyl, etc.

By silyl protecting group is meant a conventional trisubstituted silyl protecting group known to those skilled in the art such as is used to protect a hydroxy group (not to protect a silyl group). Such silyl protecting groups are described in the above cited T. W. Greene book (e.g., page 12) and include for example, silyl compounds where each of the three silyl substituents may be ($C_1$–$C_6$)alkyl optionally substituted with ($C_1$–$C_6$)alkoxy, halo or aryl; and aryl optionally substituted on carbon with halo, ($C_1$–$C_6$)alkyl, ($C_1$–$C_6$)alkoxy wherein aryl is phenyl, 2-furyl etc.

By forms a cyclic protecting group for a 1,3 diol is meant a conventional ketal or acetal protecting group known to those skilled in the art. Such cyclic protecting groups are described in the above cited T. W. Greene book (e.g., page 13 and 14) and include for example, wherein the protecting group is cyclic acetal, ($C_1$–$C_6$)alkylidene optionally substituted with ($C_1$–$C_6$)alkoxy or halo; and arylidene optionally substituted on carbon with halo, ($C_1$–$C_6$)alkyl, ($C_1$–$C_6$) alkoxy wherein arylidene is phenylidene, 2-furylidene etc, and their cyclic ketal analogs wherein the additional substituent is ($C_1$–$C_6$)alkyl optionally substituted with ($C_1$–$C_6$) alkoxy or halo or aryl optionally substituted on carbon with halo, ($C_1$–$C_6$)alkyl or ($C_1$–$C_6$)alkoxy wherein aryl is phenyl, 2-furyl etc.

By halo is meant chloro, bromo, iodo, or fluoro.

By alkyl is meant straight chain or branched saturated hydrocarbon.

This invention describes steroidal glycosides in which the sugars are substituted (e.g. with carbamoyl, thiocarbamoyl, acyl and silyl groups). In the nomenclature (see Examples and Preparations) all such groups are herein defined as substituted on oxygen unless otherwise designated as deoxy.

The Z moities described above are herein defined such that they are to be read from left to right (i.e., the left or first atom is attached to the sugar molecule and not to $R_4$).

The $C^5$–$C^6$ dotted line in the above steroidal moiety is herein defined as an optional carbon-carbon double bond.

Other features and advantages will be apparent from the specification and claims which describe the invention.

DETAILED DESCRIPTION OF THE INVENTION

SCHEME I

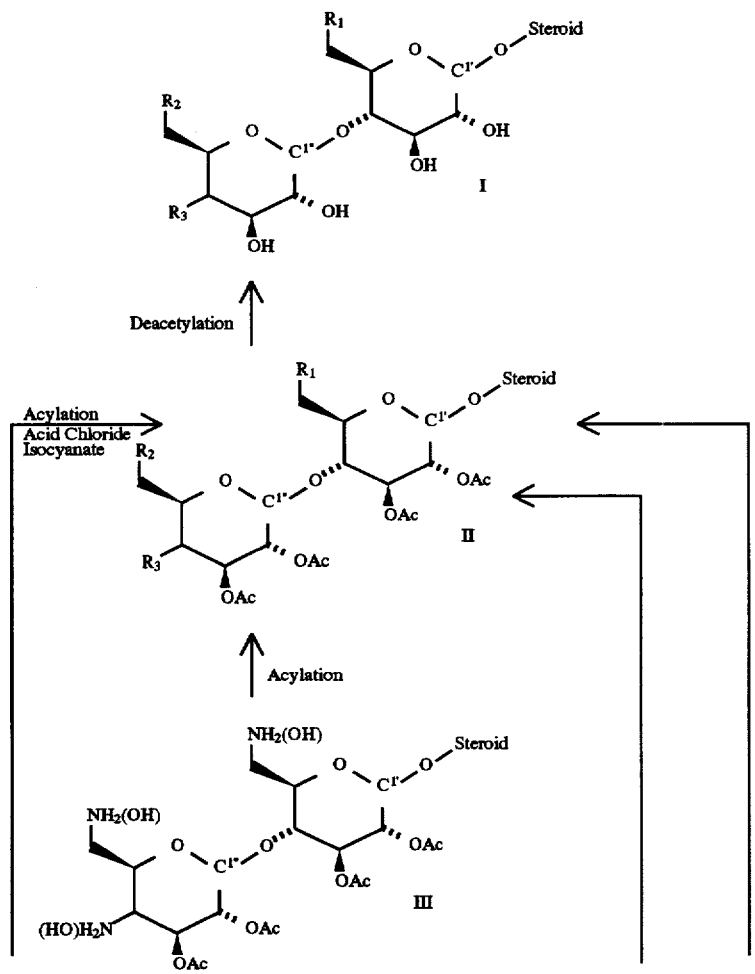

-continued
SCHEME I
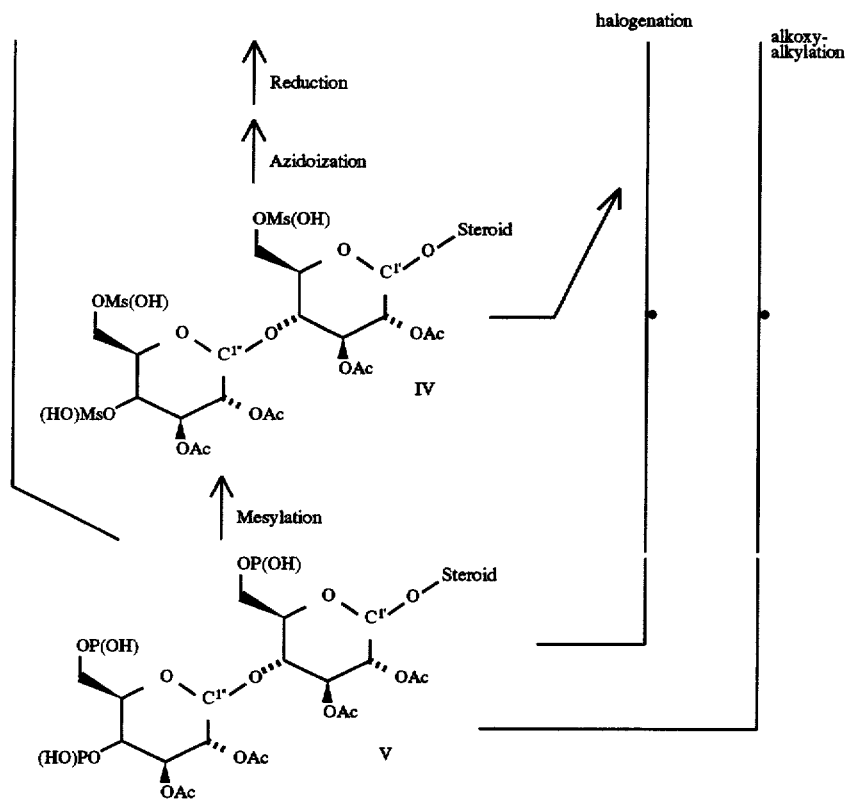
SCHEME II
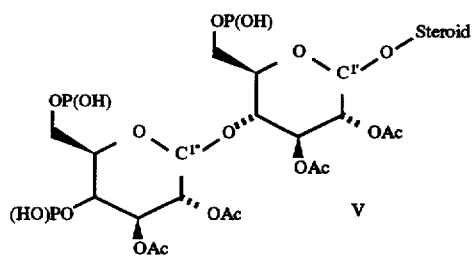

-continued
SCHEME II

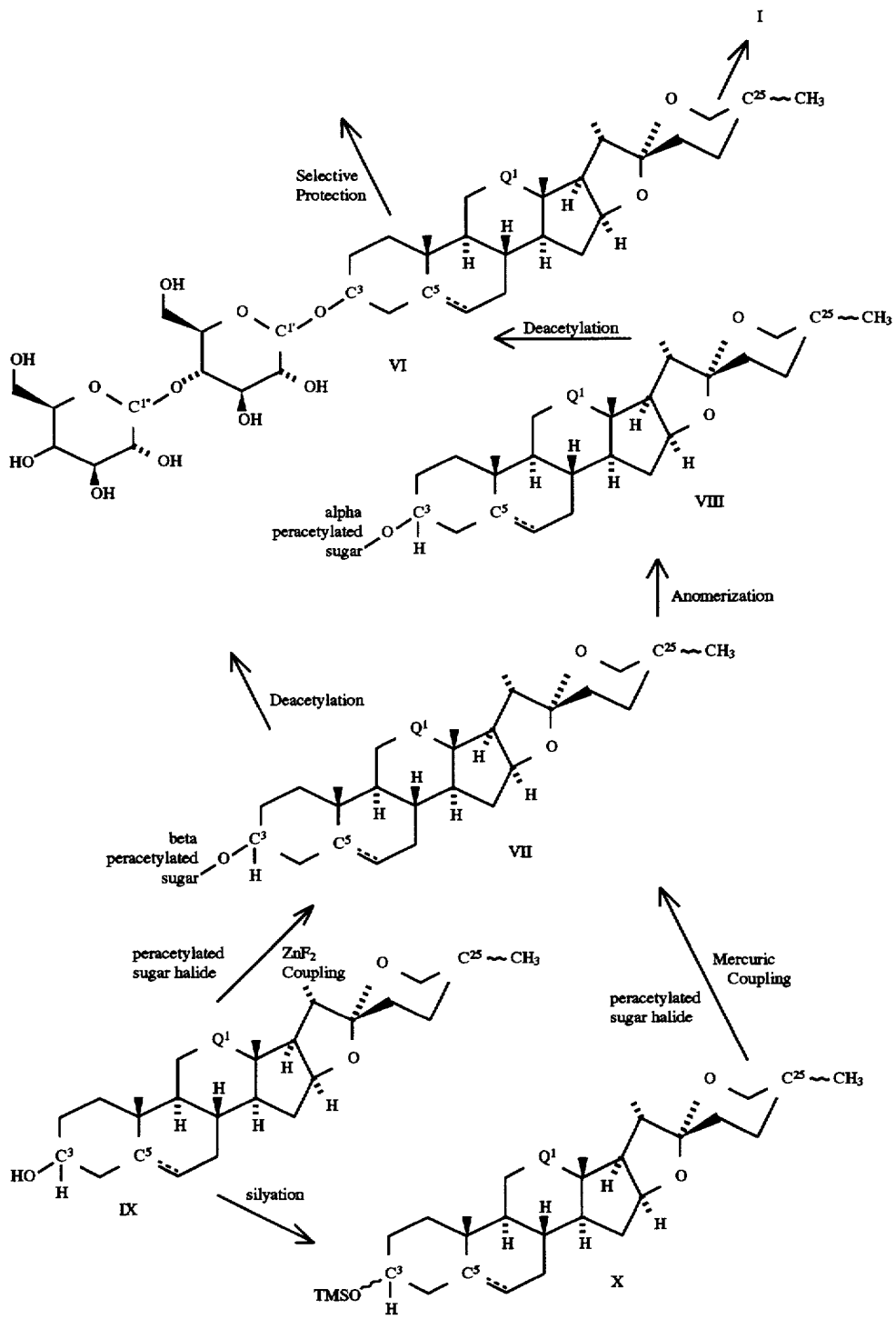

In general the compounds of this invention may be made by coupling the desired protected sugar halide and steroid followed by deprotection. The desired functionality/substituents are attached (following optional selective protection) and a final deprotection is performed. The following text (which is keyed to the above Schemes) provides a more detailed description.

According to reaction Scheme I, the desired Formula I compounds wherein Steroid is the steroidal moiety of the Formula I compound shown above (i.e., wherein $Q^1$, $C^3$, $C^5$, $C^{25}$ are as defined above) and $C^{1'}$, $C^{1''}$, $R_1$, $R_2$ and $R_3$ are as defined above may be prepared by deprotecting (e.g., deacetylating) the appropriate Formula II compound wherein Steroid is the steroidal moiety described above (although hereinafter in the Detailed Description those skilled in the art will realize that in those instances wherein $Q^1$ is hydroxy the hydroxy may exist in a conventionally protected form as a result of protection of the sugar), $C^{1'}$ and $C^{1''}$ are as defined above and $R_1$, $R_2$, and $R_3$ are as defined above or each independently is a conventionally protected hydroxyl group such as —OAc.

Typically the deprotection (preferably the deacetylation), is accomplished by combining the Formula II compound with a nucleophilic base such as sodium methoxide or potassium cyanide in a polar solvent such as methanol, tetrahydrofuran, n-propanol or mixtures thereof at temperatures of about 0° C. to about 100° C. (typically at ambient temperatures) and pressures of about 0.5 psi to about 50 psi (typically ambient) for about 0.25 hour to about 2 hours.

Additionally, the compounds may contain a silyl protecting group which can be removed by treating the deacylated product from above with a quaternary ammonium fluoride such as tetrabutyl ammonium fluoride in an anhydrous solvent such as tetrahydrofuran at temperatures of about 0° C. to about 50° C. (typically at ambient temperatures) for about 0.1 to about 3 hours.

The desired Formula II compounds wherein Steroid is the steroid moiety of Formula I compound shown above (i.e., wherein $Q^1$, $C^3$, $C^5$, $C^{25}$ are as defined above) and $C^{1'}$ and $C^{1''}$ are as defined above and at least one of $R_1$, $R_2$ and $R_3$ is hydrogen can be prepared by reduction of the corresponding halogenated compound. Typically, the reduction can be performed by treating the halogenated compound (Br and I preferred) with a reducing agent such as tri-n-butyl tin hydride and a radical initiator such as azoisobutylnitrile (AIBN) in an anhydrous aprotic solvent such as toluene at reflux temperature for about 1 hour to about 5 hours.

The desired Formula II compounds wherein Steroid is the steroidal moiety described above, $C^{1'}$ and $C^{1''}$ are as described above and at least one of $R_1$, $R_2$ and $R_3$ is halogen may be prepared by halogenation of the appropriately protected Formula V compound wherein Steroid is the steroidal moiety described above, $C^{1'}$ and $C^{1''}$ are as defined above and $R_1$, $R_2$, and $R_3$ are each independently hydroxy or a conventionally protected hydroxyl group such as —OAc.

Generally the halogenation can be performed by first preparing an appropriately activated and protected form of the Formula V compound (e.g., the Formula IV mesylate) followed by treatment with the desired lithium halide. Typically the mesylation can be performed by combining the Formula V compound and mesyl chloride in the presence of a base, preferably an amine base such as triethylamine and a catalytic amount of a catalyst such as dimethylaminopyridine in an aprotic, anhydrous solvent such as anhydrous dichloromethane at a temperature of about −20° C. to about 20° C. for about one hour to about four hours. The resulting mesylate is then treated with the appropriate lithium halide in a polar solvent such as N,N-dimethylformamide at a temperature of about 70° C. to about 100° C. for about one to about three hours.

Alternatively, the iodination can be performed by combining iodine and the appropriate Formula V compound in an anhydrous aprotic solvent such as toluene (in the presence of imidazole and triphenylphosphine) under reflux conditions and ambient pressure for about four to about eight hours.

Alternatively, the fluorination can be performed by combining the appropriate Formula V compounds with a fluorinating agent such as dialkylaminosulfur trifluoride (e.g., DAST) in an anhydrous, aprotic solvent such as dimethoxy ethane or dichloroethane at a temperature of about −10° C. to about 10° C. and then after about twenty minutes to about two hours raising the temperature to about 30° C. to about 60° C. for about one hour to about four hours.

Alternatively, a selective bromination (i.e., $R_2$=Br) can be accomplished by treating the appropriate Formula V compound (wherein $C^{6''}$ and $C^{4''}$ are substituted with OH and $C^{6'}$ is substituted with a conventionally protected hydroxyl group such as —OAc with carbon tetrabromide and triphenyl phosphine and an amine base such as pyridine in an anhydrous aprotic solvent such as dichloromethane at ambient temperature for about 6 hours to about 48 hours.

The desired Formula II compounds wherein Steroid is the steroidal moiety described above, $C^{1'}$ and $C^{1''}$ are as described above and at least one of $R_1$, $R_2$ and $R_3$ is $(C_1-C_6)$alkoxy$(C_1-C_6)$alkoxy may be prepared by alkylating the appropriately protected Formula V compound wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc.

Typically, the appropriate Formula V compound is combined with an excess of the appropriate alkoxyalkyl halide and a trialkyl amine base such as diisopropylethylamine in the presence of an anhydrous, aprotic solvent such as dichloroethane at a temperature of about 15° C. to about 35° C. (typically ambient temperature) for about one to about eight hours followed by mixing for one to four hours at a temperature of about 40° C. to about 70° C.

The desired Formula II compounds wherein Steroid is the steroid moiety described above and $C^{1'}$ and $C^{1''}$ are as defined above and at least one of $R_1$, $R_2$, and $R_3$ is Z—$R_4$ and $R_4$ contains a ketone group can be prepared by oxidation of the corresponding hydroxy substituted Formula II compound. Typically the oxidation is performed by treating the hydroxy compound with an oxidizing agent, such as pyridinium chlorochromate, in an anhydrous halogenated solvent such as dichloromethane at 0° C. to about 30° C., generally at ambient temperatures, for about 2 hours to about 24 hours.

Similarly, Formula II compounds described in the above paragraph wherein $R_4$ contains an alkylsulfinyl group may be prepared by oxidation of the corresponding alkylsulfanyl substituted Formula II compound. Typically the appropriate Formula II compound is treated with one equivalent of a peroxy acid such as meta-chloroperbenzoic acid in an anhydrous halogenated solvent such as dichloromethane at ambient temperature for 1 hour to about 6 hours. The corresponding alkylsulfonyl Formula II compounds can be prepared in an analogous manner using excess peroxy acid.

The desired Formula II compounds wherein Steroid is the steroid moiety described above, and $C^{1'}$ and $C^{1''}$ are as defined above and at least one of $R_1$, $R_2$, and $R_3$ is Z—$R_4$ and $R_4$ is alkylaminocarbonylalkyl can be prepared from the corresponding carboxy alkyl Formula II compounds through an amide forming reaction. Typically the amide is formed by reacting the carboxylic acid with a carboxyl activating agent such as a substituted carbodiimide and hydroxybenzotriazole and a primary or secondary amine chosen to give the desire amide product. The reaction is typically performed in an anhydrous aprotic solvent such as dichloromethane at ambient temperature for about 0.5 hours to about 6 hours. The carboxy alkyl Formula II compounds used in this procedure are typically prepared from the corresponding benzyl ester (the preparation of the benzyl ester being described herein) by a hydrogenolysis reaction. Thus the ester is treated with a hydrogenation catalyst such as palladium on carbon in an alcoholic solvent such as methanol and placed under 1 to 4 atmospheres of hydrogen, typically 2 atmospheres, for about 0.5 to about 8 hours.

The desired Formula I compounds wherein Steroid is the steroidal moiety described above, $C^{1'}$ and $C^{1''}$ are as described above and at least one of $R_1$, $R_2$ and $R_3$ is —O—C(=O)—$R_4$ or —O—C(=O)—N($R^5$)—$R_4$ may be prepared by acylating the appropriate Formula VI compound wherein $Q^1$, $C^{1'}$ and $C^{1''}$ are as defined above (See Scheme II). Alternatively, the desired Formula II compounds wherein at least one of $R_1$, $R_2$ and $R_3$ is —O—C(=O)—$R_4$, —O—C(=O)—N($R^5$)—$R_4$ or —O—C(=S)—N($R^5$)—$R_4$ may be prepared by acylating the appropriately protected Formula V compound wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc (See Scheme I).

A nonselective mixture of ester and carbamoyloxy substitution at $R_1$ and $R_2$ is achieved by treating the appropriately protected perhydroxy sugar Formula VI compound with the appropriate acid chloride or isocyanate and an amine base that also acts as an anhydrous solvent such as pyridine in the presence of a drying agent such as molecular sieves at a temperature of about –60° C. to about 25° C. for about 5 minutes to about 24 hours while the reaction is allowed to warm to ambient temperature. Different products and product mixes result from the variation of the amount of acid chloride or isocyanate used, the length of reaction time and the reactivity of the acid chloride or isocyanate.

Alternatively, a more selective acylation is performed by treating the appropriately protected (e.g., OAc) steroidal glycoside Formula V compound with the appropriate isocyanate or acid chloride in the presence of a base, preferably an amine base such as triethylamine or pyridine and a catalytic amount of an acylation catalyst such as dimethylaminopyridine in an anhydrous, aprotic solvent such as dichloromethane at a temperature of about –20° C. to about 20° C. The reaction mixture is allowed to warm to ambient temperature for about 10 minutes to about two hours. The carbamoylation can also be achieved by treating the appropriately protected Formula V compound with the appropriate isocyanate in the presence of cuprous chloride in a polar aprotic solvent such as dimethyl formamide at ambient temperature for two hours to about 10 hours.

The carbamoylation may also be achieved by treating the appropriately protected Formula V compound with the appropriate isocyanate in the presence of an organotin catalyst such as dibutyl tin dilaurate in an anhydrous aprotic solvent such as dichloromethane at ambient temperature for about 2 hours to about 24 hours.

In addition, the desired Formula II compounds wherein at least one of $R_1$, $R_2$ and $R_3$ is a carbamoyloxy or thiocarbamoyloxy moiety may be prepared by treatment of the appropriately protected (e.g., OAc) steroidal glycoside Formula V compound with a phosgene equivalent such as carbonyl diimidazole or a thiophosgene equivalent such as thiocarbonyl diimidazole in the presence of a base, preferably an amine base such as diisopropylethylamine in an aprotic, anhydrous solvent such as dichloroethane at a temperature of about 15° C. to about 30° C. (typically ambient temperature) for about one to about four hours. The appropriate amine is added and the reaction mixture is stirred at the same temperature for about one hour to about six hours, and heated if necessary to about 40° C. to about 60° C. for about one to about four hours.

The desired Formula II compounds wherein Steroid is the steroidal moiety described above, $C^{1'}$ and $C^{1''}$ are as described above and at least one of $R_1$, $R_2$ and $R_3$ is —NH—C(=O)—$R_4$ or —NH—C(=O)—N($R^5$)—$R_4$ may be prepared by acylating the appropriately protected Formula III compound wherein Steroid is the steroidal moiety described above, $C^{1'}$ and $C^{1''}$ are as defined above and at least one of $R_1$, $R_2$, and $R_3$ is amino.

Typically the amide may be prepared by the treatment of the appropriately protected (e.g., OAc) steroidal glycosidyl amine with the appropriate acid anhydride or acid chloride in the presence of a base, preferable an amine base such as triethylamine in an anhydrous, aprotic solvent such as dichloromethane for about one to about three hours at a temperature of about 0° C. to about 25° C.

Alternatively, the ureas may be prepared by the treatment of the appropriately protected (e.g., OAc) steroidal glycosidyl amine with the appropriate isocyanate in an anhydrous, aprotic solvent such as dichloromethane for about one to about three hours at a temperature of about 0° C. to about 25° C.

The desired Formula III compound (which happens in this case to be a Formula II compound) wherein Steroid is the steroidal moiety described above, $C^{1'}$ and $C^{1''}$ are as defined above and at least one of $R_1$, $R_2$, and $R_3$ is amino or azido may be prepared from the corresponding Formula IV mesylated or halogenated compounds by azide displacement followed if necessary by reduction.

Typically the mesylate compound is exposed to a metal azide such as sodium azide in a polar, aprotic solvent such as N,N,-dimethylformamide (in an inert atmosphere) at a temperature of about 70° C. to about 150° C. for about two to about 10 hours. The preparation of such mesylate compounds are described above for the lithium halide halogenation. Typically the azide compounds are reduced to the corresponding amines by exposure to hydrogen gas in the presence of a noble metal catalyst such as palladium on carbon at ambient temperature for about four to about forty-eight hours, under pressures of about one to about three atmospheres.

The desired Formula V compound (appropriately protected to yield the desired substitution described above) wherein Steroid is the steroidal moiety described above, $C^{1'}$ and $C^{1''}$ are as defined above and $C^{6''}$, $C^{6'}$ and $C^{4''}$ are each independently substituted with hydroxy or a conventionally protected hydroxyl group such as —OAc may be prepared by conventional protecting group methods of organic synthesis known to those skilled in the art from the corresponding Formula VI compounds wherein $Q^1$, $C^3$, $C^5$, $C^{25}$, $C^{1'}$ and $C^{1''}$ are as defined above. For a general description of protecting groups and their use, see T. W. Greene, *Protective Groups in Organic Synthesis*, John Wiley & Sons, New York, 1991. In addition, as an aid to the preparation of the above protected steroidal glycosides, the following paragraphs describe the preparation of various protected steroidal glycosides from their hydroxy analogues using a combination of differentially selective protecting groups and sequential protection reactions.

For example, the desired Formula V compound wherein Steroid is the steroidal moiety described above, $C^{1'}$ and $C^{1''}$ are as defined above, $C^{6''}$ and $C^{6'}$ are substituted with hydroxy and $C^{4''}$ is substituted with OP where P is an acyl protecting group may be conveniently prepared from the corresponding perhydroxy steroidal glycoside by silylation, acylation and desilylation. The appropriate Formula VI compound is reacted with a base, preferably an amine base such as imidazole, a bulky silylating agent selected to afford the desired silyl protecting group defined above, such as a trisubstitutedsilylhalide, preferably t-butyldiphenylsilyl chloride and a catalytic amount of a silylation catalyst such as dimethylaminopyridine in an anhydrous, aprotic solvent such as N,N-dimethyl-formamide at about −20° C. to about 10° C. followed by ambient temperature stirring for about one to about six hours. Upon completion of the silylation, a base, preferably an amine base such as pyridine and an acylating agent selected to afford the desired acyl protecting group defined above such as acetic anhydride are added at ambient temperature and pressure for about three to about twelve hours to achieve acetylation to prepare the desired protected compound (e.g., Formula IIB compound). The resulting product is treated with hydrogen fluoride in an anhydrous, aprotic solvent such as pyridine at about −20° C. to about 10° C. followed by ambient temperature stirring for about two to about six hours to prepare the desired selectively protected compound (e.g., Formula IIA compound). This product contains hydroxyl groups at the $C^6$ and $C^{6''}$ positions which can be further differentiated by reaction with one equivalent of a protecting group such as acetic anhydride in the presence of a base, such as pyridine at ambient temperatures for about 1 to about 4 hours. This procedure gives a mixture of Formula V compounds which contain a single hydroxyl group at either the $C^6$ or the $C^{6''}$ position which can be separated chromatographically.

In addition, the desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is an acyl protecting group may be conveniently prepared from the corresponding perhydroxy steroidal glycoside by ketalization, acylation and deketalization. The appropriate Formula VI compound is reacted with an acetal or ketal selected to afford the desired cyclic protecting group defined above, such as benzaldehyde dimethyl acetal or anisaldehyde dimethyl acetal, in the presence of a catalytic amount of a strong acid such as camphorsulfonic acid in an anhydrous, aprotic solvent such as chloroform or dichloroethane under reflux conditions for about two to about six hours at ambient pressure. Upon completion of the ketalization, a base preferably an amine base such as pyridine, a catalytic amount of an acylation catalyst such as dimethylaminopyridine and an acylating agent selected to afford the desired acyl protecting group defined above such as acetic anhydride or chloroacetic anhydride were added at a temperature of about −20° C. to about 10° C. followed by ambient temperature stirring for about one to about twelve hours to prepare the desired protected compound (e.g., Formula IIC compound). The resulting product is treated with 80% acetic acid in water at about 50° C. to about reflux conditions for about one to about four hours or with trifluoroacetic acid in a mixture of dichloromethane and methanol at ambient temperature for about two hours to about eight hours to prepare the desired protected compound (e.g., Formula IIA compound).

This product can further be converted to the Formula V compound wherein $C^{6'}$ and $C^{6''}$ are substituted with OP where P is an acyl or silyl protecting group and $C^{4''}$ is substituted with OH by a selective silylation reaction. Typically the silylation is performed by treating the appropriate Formula V compound wherein $C^{4''}$ and $C^{6''}$ are substituted with OH and $C^{6'}$ is substituted with OP where P is an acyl protecting group with a silylating agent such as tert-butyldimethylsilyl chloride and a base preferably an amine base such as imidazole in a polar aprotic solvent such as dimethyl formamide at ambient temperature for about 12 hours to about 48 hours.

The desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is an ether protecting group may be conveniently prepared from the corresponding perhydroxy steroidal glycoside by ketalization, etherification and deketalization. The ketalization is performed as described above. Upon completion, the solvent is removed and replaced with a polar aprotic solvent such as dimethylformamide. The appropriate alkyl halide is added such as benzyl bromide, followed by a strong base such as sodium hydride at a temperature of about −20° C. to about 0° C. for about 1 hour to about 12 hours. The deketalization is performed as described above.

The desired Formula VI compounds wherein $Q^1$, $C^3$, $C^5$, $C^{25}$, $C^{1'}$ and $C^{1''}$ are as defined above may be prepared from the corresponding Formula VII or Formula VIII peracetylated steroidal glycoside by the deacetylation process described above. For those Formula VI compounds wherein the $C^{1'}$ anomeric oxy is alpha an anomerization is performed on the corresponding Formula VII compound wherein the $C^{1'}$ anomeric oxy is beta prior to deacetylation. The stereochemical terms alpha and beta refer to the configuration of the attachment carbon of the sugar. Typically the anomedzation is performed by treatment with a mineral acid such as hydrobromic acid in an anhydrous aprotic solvent such as methylene chloride at temperatures of 20° C. to about 40° C. (typically ambient) for at least 24 hours, typically to several days.

The desired Formula VII compounds wherein $Q^1$, $C^3$, $C^5$ and $C^{25}$ are as described above may be prepared by coupling the appropriate acetylated sugar halide (e.g., bromide) and steroid. More specifically, for those Formula VII compounds where the sugar is other than beta-D-maltosyl, a zinc fluoride promoted coupling of the appropriate Formula IX compound (wherein $Q^1$, $C^3$, $C^5$ and $C^{25}$ are as described above) and peracetylated sugar halide is used and for those Formula VII compounds where the sugar is beta-D-maltosyl, a mercuric bromide and mercuric cyanide promoted coupling of the appropriate Formula X compound (e.g., trimethyl silyl ether of the Formula IX compound wherein $Q^1$, $C^3$, $C^5$ and $C^{25}$ are as described above) and peracetylated sugar halide is used.

Generally, the zinc fluoride promoted coupling of the Formula IX compound and the peracetylated sugar bromide occurs in a non-protic, anhydrous reaction-inert solvent (e.g., acetonitrile) at a temperature of about 20° C. to about 100° C. for about 0.5 to about 12 hours. Typically about 0.5 to about 4 equivalents (based on Formula IX compound) zinc fluoride is used and about 0.5 to about 3 equivalents acetylated sugar bromide is used. Preferably the coupling is acid catalyzed and it is especially preferred that hydrohalic acid generated during the reaction is used as the acid catalyst. The desired compounds may be prepared at pressures of 0.5 to 50 psi, although typically ambient pressures are used. In a preferred isolation technique the glycosides may be precipitated from the crude filtered reaction mixture (e.g., acetonitrile product solution) by the addition of about 25% to 75% water and the remainder alcohol (e.g., methanol). Precipitation of the product from aqueous methanol/acetonitrile requires less processing than an extractive isolation, and provides a product of greater purity.

Generally, the mercuric bromide and mercuric cyanide promoted coupling of the Formula X compound and the acetylated beta-D-maltosyl bromide is performed in an aprotic, anhydrous solvent such as methylene chloride at a temperature of about 20° C. to about 100° C. for about 0.5 to about 6 hours. Typically about 0.5 to about 4 equivalents (based on acetylated beta-D-maltosyl bromide) mercuric bromide and mercuric cyanide is used and about 0.5 to about 3 equivalents peracetylated beta-D-maltosyl bromide is used. The desired compounds may be prepared at pressures of 0.5 to 50 psi, although typically ambient pressures are used. Preferably they are isolated as described for the zinc fluoride promoted coupling of the Formula IX compound.

The desired Formula X compounds wherein $Q^1$, $C^3$, $C^5$ and $C^{25}$ are as described above may be prepared by silylating the appropriate Formula IX compound wherein $Q^1$, $C^3$, $C^5$ and $C^{25}$ are as described above. Generally the Formula IX compound, a base such as triethylamine and an activated trialkylsilyl compound (e.g., trimethylsilyl trifluoromethane sulfonate of trimethylsilyl chloride) are reacted in an aprotic, anhydrous solvent such as methylene chloride at a temperature less than about 10° C. for about 0.5 hour to about two hours.

In general, the procedures described above may be combined thus providing Formula I compounds wherein the $R_1$, $R_2$ and/or $R_3$ groups are dissimilar (e.g. halogenation followed by carbamoylation).

The starting materials and/or reagents for the above described reaction schemes (e.g., alkoxyalkyl halide, acid anhydride, peracetylated sugar halides, acid chlorides, isocyanates, steroids, amines, trialkylsilylchlorides, carbonyl diimidazoles, thiocarbonyl diimidazoles, silylating agents, acid derivatives, acetals, ketals, protecting groups) are readily available or can be easily synthesized by those skilled in the art using conventional methods of organic synthesis. For example some of the compounds of this invention require the synthesis of substituted amines and carboxylic acids which eventually will become $R_4$ groups. Such preparations are standard and known to those skilled in the art.

In addition, as an aid to the preparation of the above steroids, the following paragraphs describe the preparation of the various Formula IX compounds. Literature references for the preparation of Formula IX steroid compounds (wherein $Q^1$ and the stereochemistry of the $C^5$ hydrogen (or lack of the $C^5$ hydrogen) and $C^{25}$ carbon are as defined below) are described in Tables I and II.

TABLE I

Formula IX Compounds Where the $C^3$ Hydroxy Group is Beta

| $C^5$ hydrogen | $C^{25}$ | $Q^1$ | Reference |
|---|---|---|---|
| α | R | CH$_2$ | R. E. Marker et. al., J. Am. Chem. Soc. (1943) 65, 1199. |
| α | R | C=O | Marker et. al., J. Am. Chem. Soc. (1947) 69, 2167. |
| α | S | CH$_2$ | Goodson & Noller J. Am. Chem. Soc. (1939) 61, 2420. |
| α | S | C=O | Callow & James J. Chem. Soc. (1955) 1671. |
| β | R | CH$_2$ | Marker et. al., J. Am. Chem. Soc. (1943) 65, 1199. |
| β | R | C=O | Marker et. al., J. Am. Chem. Soc. (1947) 69, 2167. |
| β | S | CH$_2$ | Marker et. al., J. Am. Chem. Soc. (1943) 65, 1199. |
| β | S | C=O | Kenney & Wall J. Org. Chem. (1957) 22, 468. |

TABLE II

Formula IX Compounds Where the $C^3$ Hydroxy Group is Beta and There is a Double Bond Between $C^5$-$C^6$

| $C^{25}$ | $Q^1$ | Reference |
|---|---|---|
| R | CH$_2$ | Marker, et al., J. Am. Chem. Soc. (1943) 65, 1199. |
| R | C=O | Walens, et al., J. Org. Chem. (1957) 22, 182. |
| S | CH$_2$ | Marker, et al., A. Am. Che. Soc. (1947) 69, 2167. |
| S | C=O | Walens, et al., J. Org. Chem. (1957) 22, 182. |

The following paragraphs describe and/or give literature references for the preparation of the various steroids used as starting materials (e.g., the alternative stereochemistry at the $C^3$ position and the oxygenation and different epimers at $C^{12}$) from the above Formula IX compounds described in Tables I and II. In general the preparation of the different oxygenated steroids is independent of the stereochemistry at the $C^3$, $C^5$ (or lack of the $C^5$ hydrogen) and $C^{25}$ positions. Thus, once the appropriate stereochemistry at the $C^3$, $C^5$ (or lack of the $C^5$ hydrogen) and $C^{25}$ positions is achieved where $Q^1$ is carbonyl, the hydroxy derivatives at $Q^1$ may be prepared therefrom.

The Formula IX compounds wherein $Q^1$ is either methylene or carbonyl and the $C^3$ hydroxy is beta may be converted to the corresponding Formula IX compounds where the $C^3$ hydroxy is alpha by the following two procedures. These preparative methods may be used independent of the $C^{25}$ stereochemistry.

If $Q^1$ is carbonyl, the carbonyl is protected as a ketal (e.g., ethylene ketal), by reacting the steroid with ethylene glycol and an acid catalyst according to the procedure of Engel and Rakhit, Can. J. Chem, 1962, 40, 2153. When the $C^5$ hydrogen is alpha, the $C^3$ hydroxy group is oxidized to the ketone using pyridinium chloro chromate (PCC) in methylene chloride at ambient conditions. Then the $C^3$ ketone is reduced with a sterically hindered reducing agent such as K-Selectride® reducing agent, at low temperature in tetrahydrofuran to give the $C^3$ alpha alcohol according to Gondos and Orr, J. Chem. Soc. Chem. Commun. 21, 1239, 1982. If appropriate, the $Q^1$ protecting group is removed with acid, such as hydrochloric acid, in an appropriate solvent such as acetone. For those compounds wherein the $C^5$ hydrogen is beta the same procedures are used as were used when the $C^5$ hydrogen is alpha except the $C^3$ ketone is reduced using sodium borohydride in ethanol to furnish the $C^3$ alpha alcohol.

The Formula IX compounds wherein $Q^1$ is alpha or beta hydroxy may be prepared from the Formula IX compound wherein $Q^1$ is carbonyl. In general, preparation methods for these compounds may be found in L. F. Fieser and M. Fieser, Steroids, Reinhold Pub. Corp., New York, 1959 and references therein, however, the following descriptive text provides specific guidance.

More specifically, the starting material is reduced with lithium aluminum hydride according to the procedure described in J. Am. Chem. Soc., 1954, 76, 4013. The alpha and beta hydroxy analogs are separated chromatographically.

The compounds of Formula I which have been obtained and have asymmetric carbon atoms (e.g., some of the components of the carbamoyl moieties such as substituted amino groups) can be separated into their diastereomers and enantiomers on the basis of their physical chemical differences or optical qualities by methods known per se, for example, by chromatography and/or fractional crystallization. All such isomers, including diastereomers and enantiomers are considered as part of this invention.

The compounds of this invention where $R_4$ contains an amine group are basic and they form acid salts. All such acid salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, many of the compounds of this invention may be isolated as hydrates.

The compounds of this invention are potent inhibitors of cholesterol absorption and thus are all adapted to therapeutic use as hypercholesterolemia controlling agents in mammals, particularly humans. Since hypercholesterolemia is closely related to the development of generalized cardiovascular, cerebral vascular or peripheral vascular disorders, secondarily these compounds prevent the development of atherosclerosis particularly arteriosclerosis.

The hypercholesterolemia controlling activity of these compounds may be demonstrated by methods based on standard procedures. For example, the in vivo activity of these compounds in inhibiting intestinal absorption of cholesterol may be determined by the procedure of Melchoir and Harwell (*J. Lipid Res.*, 1985, 26, 306–315).

Activity can be determined by the amount of hypocholesterolemic agent that reduces the cholesterol absorption, relative to the control, in male golden Syrian hamsters. Male golden Syrian hamsters are administered either a cholesterol-free diet (control animals) or a diet supplemented with 1% cholesterol and 0.5% cholic acid for 4 days. The following day the animals are fasted for 18 hours, then administered a 1.5 ml oral bolus of water containing 0.25% methylcellulose, 0.6% Tween™ 80 and 10% ethanol (control animals) or an oral bolus that contains, in addition, the desired concentration of the compound to be tested. Immediately following bolus administration, the animals receive a second 1.5 ml oral bolus of liquid hamster diet containing 1% [$^3$H] cholesterol (2.0 µCi/animal; 210 dpm/nmol) and 0.5% cholic acid, and are fasted for an additional 24 hours. At the end of this second fasting period animals are sacrificed, livers are excised, saponified and aliquots are decolorized by addition of hydrogen peroxide, and assessed for radioactivity. Total hepatic radioactivity is calculated based on measured liver weights. The degree of cholesterol absorption is expressed as a percentage of the total radioactivity administered as an oral bolus that is present in the liver 24 hours following bolus administration.

Anti-atherosclerosis effects of the compounds can be determined by the amount of agent that reduces the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean±s.d. for total plasma cholesterol concentration. After group assignment, rabbits are dosed daily with compound given as a dietary admix or on a small piece of gelatin based confection. Control rabbits receive only the dosing vehicle be it the food or the gelatin confection. The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the lilac arteries. The aortae are cleaned of adventitia, opened longitudinally and then stained with Sudan IV as described by Holman et al; (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention can be via any method which delivers the compounds to the intestinal lumen. These methods include oral routes, intraduodenal routes etc.

The amount of steroidal glycoside administered will, of course, be dependent on the subject being treated, on the severity of the affliction, on the manner of administration and on the judgement of the prescribing physician. However, an effective dosage is in the range of 0.005 to 20 mg/kg/day, preferably 0.01 to 5 mg/kg/day, most preferably 0.01 to 1 mg/kg/day. For an average 70 kg human, this would amount to 0.00035 to 1.4 g/day, preferably 0.0007 to 0.35 g/day, most preferably 0.0007 to 0.07 g/day. In one mode of administration the compounds of this invention are taken with meals.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an amount effective to alleviate the signs of the subject being treated, i.e., hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those skilled in this art. For examples, see *Remington's Pharmaceutical Sciences*, Mack Publishing Company, Easter, Pa., 15th Edition (1975).

It should be understood that the invention is not limited to the particular embodiments shown and described herein, but that various changes and modifications may be made without departing from the spirit and scope of this novel concept as defined by the following claims.

EXAMPLE 1

(3β,5α,25R)-3-[(4"-[2-fluoro-phenylcarbamoyl]-β-D-cellobiosyl)oxy]-spirostan-12-one

Desilylation

Tetra-n-butyl ammonium fluoride (0.8 mL of a 1M solution in THF, 0.8 mmol) was added to a solution (3β,5α, 25R)-3-[(4"-[2-fluoro-phenylcarbamoyl]-6"-tert-butyl dimethyl silyl-β-D-cellobiosyl)oxy]-spirostan-12-one (268 mg, 0.266 mmol) in THF (10 mL) at room temperature. After 30 minutes, the mixture was concentrated and the residue was purified by recrystallization from 1-propanol:water (1:1). The solid was collected by vacuum filtration, washed with propanol:water and dried to afford 116 mg of the titled product as a colorless solid (70%). m.p. 251° C. dec. FAB MS: 914 (M+Na)$^+$. HRMS calc. for $C_{46}H_{66}FNO_{15}Na$: 914.4314. Found: 914.4390.

EXAMPLE 2

(3β,5α,25R)-3-[(4",6"-Bis[2-isopropoxycarbonyl-ethylcarbamoyl]-β-D-cellobiosyl)oxy]-spirostan-12-one

Trans-Esterification

Sodium hydride (24 mg) was added to a mixture of isopropanol (10 mL) and THF (10 mL). After 20 minutes, (3β, 5α,25R)-3-[(4",6"-bis[2-ethoxycarbonyl-ethyl carbamoyl] 2',2",3',3",6'-pentaacetyl-β-D-cellobiosyl)oxy]-spirostan-12-one (730 mg, 0.583 mmol) was added and the mixture stirred overnight at room temperature. The reaction was concentrated and the residue was purified by flash chromatography (3–6% methanol/methylene chloride) afforded 213 mg of the title compound as a colorless solid. m.p. 184°–186° C. FAB MS: 1091 (M+Na)$^+$. Analysis calc. for $C_{53}H_{84}N_2O_{20}$+0.8H$_2$O: C 58.74; H 7.96; N 2.59. Found: C 58.80; H 8.05; N 2.61.

In an analogous manner, the following compound, Example 3 was prepared from the appropriate starting material using the above general procedure.
3) (3β,5α,25R)-3-[(4",6"-bis[2-n-propoxycarbonyl-ethylcarbamoyl]-β-D-cellobiosyl)oxy]-spirostan-12-one
186°–188° C. 1091 (M+Na)$^+$ $C_{53}H_{84}N_2O_{20}$ calc. C 59.35; H 8.26; N 2.64 found C 59.64; H 7.92; N 2.62

EXAMPLE 4

(3β,5α,25R)-3-[(4",6"-Bis[2-fluoro-phenylcarbamoyl]-β-D-cellobiosyl)oxy]-spirostan-12-one

Deprotection of Chloroacetates

Sodium methoxide (250 mg) was added to a solution of (3β,5α,25R)-3-[(4",6"-bis [2-fluoro-phenylcarbamoyl]-2', 2",3',3",6'-penta-chloroacetyl-β-D-cellobiosyl)oxy]-spirostan-12-one (25 g, 17.7 mmol) in THF (75 mL) and methanol (75 mL). After 20 minutes at room temperature, the reaction was quenched by the addition of acetic acid (0.5 mL). The solvent volume was reduced by one half in vacuo and an additional 75 mL of methanol was added. With vigorous stirring, the product was precipitated by the addition of water (75 mL). The solid was filtered, washed with 1:1 methanol:water and dried to afford 15 g of crude product. The product was purified by recrystallization from THF/cyclohexane/acetic acid (100:33:0.25). m.p. 272°–273° C. FAB MS: 1051 (M+Na)$^+$. Analysis calc. for $C_{53}H_{70}F_2N_2O_{16}$+2H$_2$O: C 59.76; H 7.03; N 2.62. Found: C 59.91; H 7.32; N 2.61.

(3β,5α,25R)-3-[(4",6"-Bis[2-fluoro-phenylcarbamoyl]-β-D-cellobiosyl)oxy]-spirostan-12-one (468 g) was dissolved in 8.4 L of THF at 30° C., filtered and atmospherically distilled (i.e., at ambient pressure) replacing the distillate with ethyl acetate. When a final volume of 12 L had been reached and the distillates had the refractive index of ethyl acetate, the mixture was cooled to 20°–25° C., granulated overnight, filtered and dried to afford 363.3 g of the title compound as a white to off-white solid highly crystalline form that is believed to be thin flake and is believed to be a mixture of rod and doubley terminated blades in habit.

EXAMPLE 5

(3β,5α,25R)-3-[(6',6"-bis-[phenylcarbamoyl]-β-D-cellobiosyl)oxy]-spirostane-12-one

Deacetylation Using Sodium Methylate

To a solution of (3β,5α,25R)-3-[(6',6"-bis-[phenylcarbamoyl]-pentaacetyl-β-D-cellobiosyl)oxy]-spirostane-12-one (0.25 g, 0.21 mmol) in tetrahydrofuran (3 mL) and methanol (3 mL), sodium methylate (20 mg) was added. The reaction was stirred for 45 minutes at room temperature under nitrogen atmosphere. Upon completion, the reaction was quenched with acetic acid (2–3 drops) and concentrated in vacuo. The crude material was purified via flash chromatography (95% chloroform: 5% methanol). The isolated product was concentrated in vacuo to partial dryness and water was added causing a precipitate to form. The precipitated product was filtered, washed with water and oven-dried to afford 185 mg (90% yield) of the title compound.

$^1$HNMR (250 MHz, DMSO-d$_6$) δ9.60 (s, 1H); 9.63 (s, 1H); 6.85–7.55 (m, 10H); 5.4–5.1 (m, 4H); 4.65–2.90 (m, 19H); 2.6–1.0 (m, 25H); 0.9 (d, 3H, J=8 Hz); 0.87 (s, 3H); 0.75 (d, 3H, J=8 Hz); 0.6 (s, 3H). FAB MS: 992 (M+H)$^+$; Analysis: calculated for $C_{53}H_{72}N_2O_{16}$·1.5H$_2$O C 62.40, H 7.41, N 2.75; found C 62.36, H 7.40, N 2.82; m.p. 198°–200° C.

EXAMPLES 6–72

The following compounds were prepared from the appropriate starting material in an analogous manner using the above procedures.

| Example) m.p. | Name M.S. | formula | | elemental analysis |
|---|---|---|---|---|
| 6) (3β,5α,25R)-3-[([6',6"-dideoxy-6',6"-dichloro]-β-D-cellobiosyl)oxy]spirostan-12-one | | | | |
| >250° C. | 813(M + Na)+ | $C_{39}H_{60}Cl_2O_{12}$ | calc. | C 58.59; H 7.69 |
| | | | found | C 58.76; H 7.45 |
| 7) (3β,5α,25R)-3[([6',6"-dideoxy-6',6"-diazido]-β-D-cellobiosyl)oxy]spirostan-12-one | | | | |
| >250° C. | 805(M + H)+ | HRMS | calc. for $C_{39}H_{60}N_6O_{12}Na$ | 826.4167 |
| | | | found | 827.4114 |
| 8) (3(3β,5α,25R)-3-[(6',6"-bis[2,4-difluoro-phenylcarbamoyl]-β-D-cellobiosyl)-oxy]spirostan-12-one | | | | |
| >200° C. | 1065(M + H)+ | $C_{53}H_{68}F_4N_2O_{16}$ | | |
| 9) (3β,5α,25R)-3-[([6',6"-dideoxy-6',6"-dichloro]-β-D-lactosyl)oxy]spirostan-12-one | | | | |
| 243–244° C. (dec.) | 791(M + H)+ | HRMS | calc. for $C_{39}H_{61}C_{12}O_{12}$ found | 791.3540 791.3495 |
| 10) (3β,5α,25R)-3-[([6',6"-dideoxy-6',6"-difluoro]-β-D-cellobiosyl)oxy]spirostane | | | | |
| >270° C. | 745(M + H)+ | $C_{39}H_{62}F_2O_{11}$ + 2 $H_2O$ | calc. found | C 59.99; H 8.51 C 60.13; H 8.26 |
| 11) (3β,5α,25R)-3-[([6',6"dideoxy-6,6"-difluoro]-β-D-cellobiosyl)oxy]spirostan-12-one | | | | |
| >280° C. | 759(M + H)+ | $C_{39}H_{60}F_2O_{12}$ + 1 $H_2O$ | calc. found | C 60.32; H 8.04 C 60.62; H 7.85 |
| 12) (3β,5α,25R)-3-[([6"-deoxy-6"-fluoro]-β-D-cellobiosyl)oxy]spirostan-12-one | | | | |
| >280° C. | 757(M + H)+ | $C_{39}H_{61}FO_{13}$ + $H_2O$ | calc. found | C 60.44; H 8.19 C 60.60; H 7.98 |
| 13) (3β,5α,25R)-3-[([6'-deoxy-6'-fluoro]-β-D-cellobiosyl)oxy]spirostan-12-one | | | | |
| >270° C. | 757(M + H)+ | $C_{39}H_{61}FO_{13}$ | calc. found | C 59.75; H 8.23 C 59.51; H 8.08 |
| 14) (3β,5α,25R)-3-[([6',6"-dideoxy-6'-amino-6"-acetamido]-β-D-cellobiosyl)oxy] spirostane | | | | |
| 225° C. (dec) | 781(M + H)+ | HRMS | calc. for $C_{41}H_{66}N_2O_{12}Na$ found | 803.4670 803.4735 |
| 15) (3β,5α,25R)-3-[([6',6"-dideoxy-6',6"-bis(acetamido)]-β-D-cellobiosyl)oxy]spirostan-12-one | | | | |
| >250° C. | 837(M + H)+ | $C_{43}H_{58}N_2O_{16}$ + 1.5 $H_2O$ | calc. found | C 59.78; H 8.28; N 3.24 C 59.47; H 7.99; N 3.11 |
| 16) (3β,5α,25R)-3-[([6',6"-dideoxy]-β-D-cellobiosyl)oxy]spirostane | | | | |
| >275° C. | 709(M + H)+ | $C_{39}H_{64}O_{11}$ + 0.5 $H_2O$ | calc. found | C 65.25; H 9.00 C 65.16; H 8.60 |
| 17) (3β,5α,25R)-3-[(4",6"-bis[4-acetyl-phenylcarbamoyl]-β-D-cellobiosyl)oxy]-spirostan-12-one | | | | |
| 244–248° C. | 1099 (M + Na)+ | $C_{57}H_{76}N_2O_{18}$ + 3$H_2O$ | calc. found | C 60.52; H 7.31; N 2.48 C 60.25; H 7.36; N 2.17 |
| 18) (3β,5α,25R)-3-[(4",6"-bis[3-acetyl-phenylcarbamoyl]-β-D-cellobiosyl)oxy]-spirostan-12-one | | | | |
| 226–229° C. | 1099 (M + Na)+ | $C_{57}H_{76}N_2O_{18}$ + 2$H_2O$ | calc. found | C 61.50; H 7.24; N 2.52 C 61.70; H 7.31; N 2.52 |
| 19) (3β,5α,25R)-3-[(6"-[3-5-dimethoxy-phenylcarbamoyl]-β-D-cellobiosyl)oxy]-spirostan-12-one | | | | |
| 244–248° C. | 956 (M + Na)+ | $C_{48}H_{71}NO_{17}$ + 2$H_2O$ | calc. found | C 59.43; H 7.79; N 1.44 C 59.54; H 8.12; N 1.15 |
| 20) (3β,5α,25R)-3-[(4",6"-bis[3-dimethylamino-phenylcarbamoyl]-β-D-cellobiosyl)oxy]-spirostan-12-one | | | | |
| 249–254° C. | 1101 (M + Na)+ | $C_{57}H_{82}N_4O_{16}$ + 3$H_2O$ | calc. found | C 60.41; H 7.83; N 4.94 C 60.31; H 8.04; N 4.88 |
| 21) (3β,5α,25R)-3-[(4",6"-bis[4-methyl-piperazin-1-ylcarbonyl]-β-D-cellobiosyl)oxy]-spirostan-12-one | | | | |
| 257–259° C. dec | 1029 (M + Na)+ | $C_{51}H_{82}N_4O_{16}$ + 1.75$H_2O$ | calc. found | C 58.97; H 8.30; N 5.39 C 58.66; H 8.45; N 5.78 |
| 22) (3β,25R)-3-[(4",6"-bis[2-fluoro-phenylcarbamoyl]-β-D-cellobiosyl)oxy]-5-spirostene | | | | |
| 260–261° C. | 1035 (M + Na)+ | $C_{53}H_{70}F_2N_2O_{15}$ + 1$H_2O$ | calc. found | C 61.74; H 7.04; N 2.72 C 61.65; H 7.29; N 2.69 |
| 23) (3β,5α,25R)-3-[(4",6"-bi[pyrrolidin-1-yl-carbonyl]-β-D-cellobiosyl)oxy]-spirostan-12-one | | | | |
| 266–268° C. | 971 (M + Na)+ | $C_{49}H_{76}N_2O_{16}$ + 1.5$H_2O$ | calc. found | C 60.29; H 8.16; N 2.87 C 60.40; H 8.31; N 2.95 |
| 24) (3β,5α,25R)-3-[(6"-[indolin-1-yl-carbonyl]-β-D-cellobiosyl)oxy]-spirostan-12-one | | | | |
| | 922 (M + Na)+ | HRMS | calc for: $C_{48}H_{59}NO_{15}Na$ found: | 922.4565 922.4588 |
| 25) (3β,5α,25R)-3-[(4",6"-bis[pyridin-2-yl-methylcarbamoyl]-β-D-cellobiosyl)oxy]-spirostan-12-one | | | | |
| 234–236° C. | 1045 (M + Na)+ | $C_{53}H_{74}N_4O_{16}$ + 0.5$H_2O$ | calc. found | C 61.69; H 7.33; N 5.42 C 61.81; H 7.56; N 5.14 |
| 26) (3β,5α,25R)-3-[(6"-[pyridin-2-yl-methylcarbamoyl]-β-D-cellobiosyl)oxy]-spirostan-12-one | | | | |
| >270° C. | 897 (M + Na)+ | $C_{45}H_{66}N_2O_{15}$ | calc. found | C 61.77; H 7.60; N 3.20 C 61.41; H 7.95; N 3.16 |
| 27) (3β,5α,25R)-3-[(6',6"-bis[trans-2-hydroxy-cyclohexylcarbamoyl]-β-D-cellobiosyl)oxy9-spirostan-12-one | | | | |

-continued

| Example) m.p. | Name M.S. | formula | | elemental analysis |
|---|---|---|---|---|
| 200–202° C. | 1059 (M + Na)⁺ | $C_{53}H_{84}N_2O_{18}$ + 1H$_2$O | calc. found | C 60.32; H 8.21; N 2.65<br>C 60.39; H 8.40; N 2.48 |
| 28) (3β,5α,25R)-3-[(6',6"-bis[2-oxo-cyclohexylcarbamoyl]-β-D-cellobiosyl)oxy]-spirostan-12-one | | | | |
| 220° C. dec | 1055 (M + Na)⁺ | $C_{53}H_{80}N_2O_{18}$ + 0.5H$_2$O | calc. found | C 61.07; H 7.83; N 2.69<br>C 60.88; H 7.96; N 2.48 |
| 29) (3β,5α,25R)-3-[(4",6"-bis[3-methoxy-phenylcarbamoyl]-β-D-cellobiosyl)oxy]-spirostan-12-one | | | | |
| 168–173° C. | 1075 (M + Na)⁺ | $C_{55}H_{76}N_2O_{18}$ + 0.75H$_2$O | calc. found | C 61.70; H 7.11; N 2.62<br>C 61.70; H 7.33; N 2.57 |
| 30) (3β,5α,25R)-3-[(4",6"-bis[2-fluoro-phenylcarbamoyl]-β-D-lactosyl)oxy]-spirostan-12-one | | | | |
| 171–175° C. | 1051 (M + Na)⁺ | $C_{53}H_{70}F_2N_2O_{16}$ + 1H$_2$O | calc. found | C 60.79; H 6.93; N 2.68<br>C 60.59; H 7.02; N 2.68 |
| 31) (3β,5α,25R)-3-[(6"-[2-fluoro-phenylcarbamoyl]-β-D-lactosyl)oxy]-spirostan-12-one | | | | |
| >260° C. | 914 (M + Na)⁺ | $C_{46}H_{66}FNO_{15}$ + 1H$_2$O | calc. found | C 60.71; H 7.53; N 1.54<br>C 60.58; H 7.59; N 1.67 |
| 32) (3β,5α,25R)-3-[(4",6"-bis[2-ethoxycarbonyl-ethylcarbamoyl]-β-D-cellobiosyl)oxy]-spirostan-12-one | | | | |
| 205–220° C. | 1063 (M + Na)⁺ | $C_{51}H_{80}N_2O_{20}$ + 0.5H$_2$ | calc. found | C 58.33; H 7.77; N 2.67<br>C 58.45; H 8.01; N 2.71 |
| 33) (3β,5α,25R)-3-[(4",6"-bis[2-methoxy-ethylcarbamoyl]-β-D-cellobiosyl)oxy]-spirostan-12-one | | | | |
| 227° C. dec | 979 (M + Na)⁺ | $C_{47}H_{76}N_2O_{18}$ + 0.5H$_2$O | calc. found | C 58.43; H 8.03; N 2.90<br>C 58.27; H 8.29; N 2.83 |
| 34) (3β,5α,25R)-3-[(4",6"-bis[methoxycarbonylmethyl-methyl-carbamoyl]-β-D-cellobiosyl)oxy]-spirostan-12-one | | | | |
| 218–220° C. | 1035 (M + Na)⁺ | $C_{49}H_{76}N_2O_{20}$ + 1.5H$_2$O | calc. found | C 56.58; H 7.66; N 2.69<br>C 56.69; H 7.97; N 2.69 |
| 35) (3β,5α,25R)-3-[(6"-[1-methoxycarbonyl-propylcarbamoyl]-β-D-cellobiosyl)oxy]-spirostan-12-one | | | | |
| 247–250° C. | 920 (M + Na)⁺ | $C_{45}H_{71}NO_{17}$ | calc. found | C 60.32; H 8.29; N 1.56<br>C 60.19; H 7.97; N 1.56 |
| 36) (3β,5α,25R)-3-[(4",6"-bis[1,2-bis(methoxycarbonyl)-ethylcarbamoyl]-β-D-cellobiosyl)oxy]-spirostan-12-one | | | | |
| 222–224° C. | 1151 (M + Na)⁺ | $C_{53}H_{80}N_2O_{24}$ | calc. found | C 56.59; H 7.53; N 2.59<br>C 56.37; H 7.14; N 2.48 |
| 37) (3β,5α,25R)-3-[(4",6"-Bis[2-methoxycarbonyl-ethyl carbamoyl]-β-D-cellobiosyl)oxy]-spirostan-12-one | | | | |
| 198–201° C. | 1035 (M + Na)⁺ | $C_{49}H_{76}N_2O_{20}$ | calc. found | C 58.13; H 7.96; N 2.59<br>C 58.09; H 7.56; N 2.99 |
| 38) (3β,5α,25R)-3-[(4",6"-bis[2-t-butoxycarbonyl-ethylcarbamoyl]-β-D-cellobiosyl)oxy]-spirostan-12-one | | | | |
| 184–186° C. | 1119 (M + Na)⁺ | $C_{55}H_{88}N_2O_{20}$ + 0.6H$_2$O | calc. found | C 59.62; H 8.11; N 2.53<br>C 59.65; H 8.27; N 2.47 |
| 39) (3β,5α,25R)-3-[(4",6"-Bis[methylaminocarbonyl-methylcarbamoyl]-β-D-cellobiosyl)oxy]-spirostan-12-one | | | | |
| >260° C. | 1005 (M + Na)⁺ | $C_{47}H_{74}N_4O_{18}$ + 2.5H$_2$O | calc. found | C 54.91; H 7.74; N 5.45<br>C 54.86; H 7.88; N 5.39 |
| 40) (3β,5α,25R)-3-[(4",6"-Bis[1-(2-thienyl)-ethylcarbamoyl]-β-D-cellobiosyl)oxy]-spirostan-12-one | | | | |
| 188–189° C. | 1083 (M + Na)⁺ | $C_{53}H_{76}N_2O_{16}S_2$ + 1H$_2$O | calc. found | C 58.98; H 7.28; N 2.60<br>C 59.00; H 7.60; N 2.90 |
| 41) (3β,5α,25R)-3-[(4",6"-Bis[3-hydroxy-propylcarbamoyl]-β-D-cellobiosyl)oxy]-spirostan-12-one | | | | |
| >260° C. | 979 (M + Na)⁺ | $C_{47}H_{76}N_2O_{18}$ + 4.5H$_2$O | calc. found | C 54.38; H 8.25; N 2.70<br>C 54.29; H 7.86; N 2.54 |
| 42) (3β,5α,25R)-3-[(4",6"-Bis[2-(methylaminocarbonyl)-ethylcarbamoyl]-β-D-cellobiosyl)oxy]-spirostan-12-one | | | | |
| >260° C. | 1033 (M + Na)⁺ | $C_{49}H_{78}N_4O_{18}$ + 1.5H$_2$O | calc. found | C 56.69; H 7.86; N 5.40<br>C 56.42; H 8.13; N 5.32 |
| 43) (3β,5α,25R)-3-[(4",6"-Bis[2-thienyl-methylcarbamoyl]-β-D-cellobiosyl)oxy]-spirostan-12-one | | | | |
| 202–214° C. | 1055 (M + Na)⁺ | $C_{51}H_{72}N_2O_{16}S_2$ + 1H$_2$O | calc. found | C 58.27; H 7.09; N 2.66<br>C 58.36; H 7.15; N 2.96 |
| 44) (3β,5α,25R)-3-[(4",6"-Bis[2-(dimethylaminocarbonyl)-ethylcarbamoyl]-β-D-cellobiosyl)oxy]-spirostan-12-one | | | | |
| 201–202° C. | 1061 (M + Na)⁺ | $C_{51}H_{82}N_4O_{18}$ + 1H$_2$O | calc. found | C 57.45; H 8.04; N 5.25<br>C 57.49; H 8.39; N 4.96 |
| 45) (3β,5α,25R)-3-[(4",6"-Bis[3-oxo-3-pyrrolidin-1-yl-propylcarbamoyl]-β-D-cellobiosyl)oxy]-spirostan-12-one | | | | |
| 206–208° C. | 1113 (M + Na)⁺ | $C_{55}H_{86}N_4O_{18}$ + 1.5H$_2$O | calc. found | C 59.07; H 8.02; N 5.01<br>C 59.07; H 8.36; N 4.71 |
| 46) (3β,5α,25R)-3-[(4",6"-Bis[2-methoxycarbonyl-propylcarbamoyl]-β-D-cellobiosyl)oxy]-spirostan-12-one | | | | |
| 208–211° C. | 1063 (M + Na)⁺ | $C_{51}H_{80}N_2O_{20}$ + | calc. | C 57.83; H 7.80; N 2.64 |

-continued

| Example) m.p. | Name M.S. | formula | | elemental analysis |
|---|---|---|---|---|
| | | 1H₂O | found | C 57.78; H 8.04; N 2.41 |
| 47) (3β,5α,25R)-3-[(4",6"-Bis[ethoxycarbonyl-methylcarbamoyl]-β-D-cellobiosyl) oxy]-spirostan-12-one | | | | |
| 214–215° C. | 1035 (M + Na)⁺ | C₄₉H₇₆N₂O₂₀ + | calc. | C 57.08; H 7.62; N 2.72 |
| | | 1H₂O | found | C 57.22; H 7.79; N 2.83 |
| 48) (3β,5α,25R)-3-[(4",6"-Bis[2-methylsulfanyl-ethylcarbamoyl]-β-D-cellobiosyl)oxy]-spirostan-12-one | | | | |
| 222–225° C. | 1011 (M + Na)⁺ | C₄₇H₇₆N₂O₁₆S₂ + | calc. | C 56.04; H 7.81; N 2.78 |
| | | 1H₂O | found | C 55.90; H 7.90; N 2.77 |
| 49) (3β,5α,25R)-3-[(4",6"-Bis[4-nitro-benzylcarbamoyl-β-D-cellobiosyl)oxy]-spirostan-12-one | | | | |
| 220–223° C. | 1133 (M + Na)⁺ | C₅₅H₇₄N₄O₂₀ + | calc. | C 57.85; H 6.83; N 4.91 |
| | | 1.7H₂O | found | C 57.86; H 7.01; N 4.97 |
| 50) (3β,5α,25R)-3-[(4",6"-Bis[3-fluoro-benzylcarbamoyl]-β-D-cellobiosyl)oxy]-spirostan-12-one | | | | |
| 238–241° C. | 1079 (M + Na)⁺ | C₅₅H₇₄F₂N₂O₁₆ + | calc. | C 61.23; H 7.14; N 2.60 |
| | | 1.2H₂O | found | C 61.29; H 7.38; N 2.62 |
| 51) (3β,5α,25R)-3-[(4",6"-Bis[2-methanesulfonyl-ethylcarbamoyl]-β-D-cellobiosyl)-oxy]-spirostan-12-one | | | | |
| 260–264° C. | 1075 (M + Na)⁺ | C₄₇H₇₅N₂O₂₀S₂ + | calc. | C 52.96; H 7.32; N 2.63 |
| | | 0.7H₂O | found | C 52.82; H 7.71; N 2.66 |
| 52) (3β,5α,25R)-3-[(4",6"-Bis[2-methanesulfinyl-ethylcarbamoyl]-β-D-cellobiosyl)oxy]-spirostan-12-one | | | | |
| 244–245° C. | 1043 (M + Na)⁺ | C₄₇H₇₆N₂O₁₈S₂ + | calc. | C 53.85; H 7.60; N 2.67 |
| | | 1.5H₂O | found | C 53.86; H 7.98; N 2.59 |
| 53) (3β,5α,25R)-3-[(4",6"-Bis[3-oxo-butylcarbamoyl]-β-D-cellobiosyl)oxy]-spirostan-12-one | | | | |
| 228–230° C. | 1003 (M + Na)⁺ | C₄₉H₇₆N₂O₁₈ + | calc. | C 59.86; H 8.00; N 2.85 |
| | | 0.5H₂O | found | C 59.74; H 8.40; N 2.81 |
| 54) (3β,5α,25R)-3-[(4",6"-Bis[2-methoxycarbonyl-2-methyl-propylcarbamoyl]-β-D-cellobiosyl)oxy]-spirostan-12-one | | | | |
| 227–229° C. | 1091 (M + Na)⁺ | C₅₃H₈₄N₂O₂₀ + | calc. | C 57.70; H 7.86; N 2.54 |
| | | 2H₂O | found | C 57.73; H 8.11; N 2.66 |
| 55) (3β,5α,25R)-3-[(4",6"-Bis[3-oxo-pentylcarbamoyl]-β-D-cellobiosyl)oxy]-spirostan-12-one | | | | |
| 225–231 ° C. | 1031 (M + Na)⁺ | C₅₁H₈₀N₂O₁₈ + | calc. | C 59.63; H 8.05; N 2.73 |
| | | 1H₂O | found | C 59.58; H 8.16; N 2.57 |
| 56) (3β,5α,25R)-3-[(6"-deoxy-β-D-cellobiosyl)oxy]-spirostan-12-one | | | | |
| >260° C. | 761 (M + Na)⁺ | C₃₉H₆₂O₁₃ + | calc. | C 59.75; H 8.61 |
| | | 2.5H₂O | found | C 59.72; H 8.46 |
| 57) (3β,5α,25R)-3-[(4",6"-Bis[3-ethoxycarbonyl-propylcarbamoyl]-β-D-cellobiosyl)oxy]-spirostan-12-one | | | | |
| 194–196° C. | 1091 (M + Na)⁺ | C₅₃H₈₄N₂O₂₀ + | calc. | C 58.07; H 8.00; N 2.56 |
| | | 1.5H₂O | found | C 58.00; H 8.05; N 2.57 |
| 58) (3β,5α,25R)-3-[(4",6"-Bis[2-oxo-cyclopentyl-methylcarbamoyl]-β-D-cellobiosyl) oxy]-spirostan-12-one | | | | |
| 248–251 ° C. | 1055 (M + Na)⁺ | C₅₃H₈₀N₂O₁₈ + | calc. | C 59.54; H 7.92; N 2.62 |
| | | 1H₂O | found | C 59.65; H 7.90; N 2.65 |
| 59) (3β,5α,25R)-3-[(4",6"-Bis[trans-2-hydroxy-cyclopentyl-methylcarbamoyl]-β-D-cellobiosyl)oxy]-spirostan-12-one | | | | |
| 249–252° C. | 1059 (M + Na)⁺ | C₅₃H₈₄N₂O₁₈ + | calc. | C 58.82; H 8.29; N 2.59 |
| | | 2.5H₂O | found | C 58.82; H 8.25; N 2.43 |
| 60) (3β,5α,25R)-3-[(4",6"-Bis[2-methoxycarbonyl-butylcarbamoyl]-β-D-cellobiosyl) oxy]-spirostan-12-one | | | | |
| 200–201° C. | 1091 (M + Na)⁺ | C₅₃H₈₄N₂O₂₀ + | calc. | C 57.88; H 8.01; N 2.55 |
| | | 1.7H₂O | found | C 57.95; H 8.07; N 2.62 |
| 61) (3β,5α,25R)-3[(4",6"-Bis[1-methoxycarbonyl-cyclopropyl-methylcarbamoyl]-β-D-cellobiosyl)oxyl]-spirostan-12-one | | | | |
| 224–228° C. | 1087 (M + Na)⁺ | C₅₃H₈₀N₂O₂₀ + | calc. | C 58.28; H 7.66; N 2.56 |
| | | 1.5H₂O | found | C 58.17; H 7.73; N 2.62 |
| 62) (3β,5α,25R)-3-[(4",6"-Bis[2-methoxycarbonyl-1-methyl-ethylcarbamoyl]-β-D-cellobiosyl)oxy]-spirostan-12-one | | | | |
| 214–218° C. | 1124 (M + Na)⁺ | C₅₁H₈₀N₂O₂₀ + | calc. | C 56.86; H 7.86; N 2.60 |
| | | 2H₂O | found | C 56.64; H 8.12; N 2.43 |
| 63) (3β,5α,25R)-3-[(4",6"-Bis[thiazol-2-yl-methylcarbamoyl]-β-D-cellobiosyl)oxy]-spirostan-12-one | | | | |
| 242–242° C. | 1057 (M + Na)⁺ | C₄₉H₇₀N₄O₁₆S₂ + | calc. | C 53.67; H 7.06; N 5.11 |
| | | 3.4H₂O | found | C 53.59; H 6.90; N 5.18 |
| 64) (3β,5α,25R)-3-[(4",6"-Bis[4,5-dimethyl-thiazol-2-yl-methylcarbamoyl]-β-D-cellobiosyl)oxy]-spirostan-12-one | | | | |
| 219–222° C. | 1057 (M + Na)⁺ | C₅₃H₇₈N₄O₁₆S₂ + | calc. | C 56.29; H 7.34; N 4.95 |
| | | 2.2H₂O | found | C 56.10; H 7.46; N 4.80 |
| 65) (3β,5α,25R)-3-[(4",6"-Bis[3-ethoxycarbonyl-piperidin-1-yl-carbonyl]-β-D-cellobiosyl)oxy]-spirostan-12-one | | | | |
| 188–193° C. | 1143 (M + Na)⁺ | C₅₇H₈₈N₂O₂₀ + | calc. | C 59.15; H 8.01; N 2.42 |
| | | 2H₂O | found | C 59.17; H 8.01; N 2.43 |
| 66) (3β,5α,25R)-3-[(4",6"-Bis[trans-2-ethoxycarbonyl-cyclopropylcarbamoyl]-β-D- | | | | |

-continued

| Example) m.p. | Name M.S. | formula | | elemental analysis |
|---|---|---|---|---|
| cellobiosyl)oxy]-spirostan-12-one | | | | |
| 197–205° C. | 1087 (M + Na)⁺ | $C_{53}H_{80}N_2O_{20}$ + 1.7$H_2O$ | calc. found | C 58.09; H 7.67; N 2.56<br>C 58.13; H 7.92; N 2.87 |
| 67) (3β,5α,25R)-3-[(4",6"-bis[trans-2-methoxycarbonyl-cyclopentylcarbamoyl]-β-D-cellobiosyl)oxy]-spirostan-12-one | | | | |
| 218.5–221° C. | 1115 (M + Na)⁺ | $C_{55}H_{84}N_2O_{20}$ + 1.7$H_2O$ | calc. found | C 58.78; H 7.84; N 2.49<br>C 58.69; H 7.94; N 2.74 |
| 68) (3β,5α,25R)-3-[(4",6"-bis[2-methoxycarbonyl-2-phenyl-ethylcarbamoyl]-β-D-cellobiosyl)oxy]-spirostan-12-one | | | | |
| 200.5–202° C. | 1187 (M + Na)⁺ | $C_{61}H_{84}N_2O_{20}$ | calc. found | C 60.99; H 7.38; N 2.33<br>C 60.87; H 7.73; N 2.51 |
| 69) (3β,5α,25R)-3-[(4",6"-bis[thiophen-2-yl-methyl-thiocarbamoyl]-β-D-cellobiosyl)oxy]-spirostan-12-one | | | | |
| 181° C. (dec) | 1087 (M + Na)⁺ | HRMS | calc. for $C_{51}H_{72}N_2O_{14}S_4Na$ found | 1087.3764<br>1087.38071 |
| 70) (3β,5α,25R)-3-[(6"-benzamido-6"-deoxy-β-D-cellobiosyl)oxy]-spirostan-12-one | | | | |
| 244–251° C. | 880(M + Na)⁺ | HRMS | calc. for $C_{46}H_{67}NO_{14}Na$ found | 880.4459<br>880.44386 |
| 71) (3β,5α,12β,25R)-3-[(4",6"-bis[2-fluoro-phenylcarbamoyl]-β-D-cellobiosyl)oxy]-12-hydroxy-spirostane | | | | |
| 233–238° C. | 1053 (M + Na)⁺ | $C_{53}H_{72}F_2N_2O_{16}$ + 2.5$H_2O$ | calc. found | C 59.15; H 7.21; N 2.60<br>C 59.00; H 7.48; N 2.74 |
| 72) (3β,5α,25R)-3-[(6"-deoxy-6"-[3-(2-fluoro-phenyl)-ureido]-β-D-cellobiosyl)oxy]-spirostan-12-one | | | | |
| >260° C. | 913 (M + Na)⁺ | $C_{46}H_{67}FN_2O_{14}$ + 1$H_2O$ | calc. found | C 60.78; H 7.65; N 3.08<br>C 60.71; H 7.48; N 3.04 |

EXAMPLE 73

(3β,5α,25R)-3-[(6',6"-bis[2-trifluoromethyl-phenylcarbamoyl]-β-D-cellobiosyl)oxy]spirostan-12-one

Deacylation Using Potassium Cyanide

Potassium cyanide (50 mg) was added to a solution of (3β,5α,25R)-3-[(6',6"-bis[2-trifluoromethyl-phenylcarbamoyl]pentaacetyl-β-D-cellobiosyl)oxy] spirostan-12-one (550 mg, 0.41 mmol) in THF (5 mL) and methanol (5 mL) at ambient temperature. After two hours, 10 mL of methanol was added and the mixture concentrated to approx. 5 mL. Water (50 mL) was added and the precipitate was collected by vacuum filtration and dried in a vacuum oven at 80° C. The product was purified by flash chromatography (5% methanol/dichloromethane) to give 130 mg (28%) product as a colorless solid.

$^1$H NMR (250 MHz, $d_6$ DMSO) δ9.02 (s, 1H); 9.0 (s, 1H), 7.5 (m, 8H); 5.35 (d, 1H, J=5 Hz); 5.25 (d, 1H, J=5 Hz); 5.15 (d, 1H, J=5 Hz); 5.1 (d, 1H, J=5 Hz); 4.5 (s, 1H); 4.3 (m, 8H); 3.5–3.0 (m, 12H); 2.4(d, 1H, J=14 Hz); 2.3 (dd, 1H, J=14, 8 Hz); 2.0–1.0 (m, 21H); 0.95 (s, 3H); 0.9 (d, 3H, J=7 Hz); 0.8 (s, 3H); 0.7 (s, 3H). FAB MS: 1151 (M+Na)⁺. m.p. 173°–174° C. Analysis, calculated for $C_{55}H_{70}F_6N_2O_{16}$+ 1.5$H_2O$ C 57.14 H 6.36 N 2.42; Found C 57.18 H 6.08 N 2.34.

EXAMPLES 74–89

The following compounds were prepared from the appropriate starting material in an analogous manner using the above procedures.

| Example) m.p. | Name M.S. | formula | | elemental analysis | | | |
|---|---|---|---|---|---|---|---|
| 74) (3β,5α,25R)-3-[(6',6"-bis[pivaloyl]-β-D-cellobiosyl)oxy]spirostan-12-one | | | | | | | |
| >200° C. | 923(M + H)⁺ | $C_{49}H_{78}O_{16}$ +0.75 $H_2O$ | calc. C found C | 62.78;<br>62.72; | H<br>H | 8.49<br>8.09 | |
| 75) (3β,5α,25R)-3-[(6',6"-bis[ethoxycarbonyl-methylcarbamoyl]-β-D-cellobiosyl)oxy]-spirostan-12-one | | | | | | | |
| 192–193.2° C. | 1012(M + H)⁺<br>1034(M + Na)⁺ | $C_{49}H_{76}N_2O_{20}$ | calc. C found C | 58.12;<br>58.01; | H<br>H | 7.51<br>7.15 | |
| 76) (3β,5α,25R)-3-[(6',6"-bis[4-nitro-phenylcarbamoyl]-β-D-cellobiosyl)oxy]spirostan-12-one | | | | | | | |
| 210° C. | 1082(M + H)⁺ | $C_{53}H_{70}N_4O_{20}$ +2.5 $H_2O$ | calc. C found C | 56.43;<br>56.21; | H<br>H | 6.70;<br>6.39; | N 4.96<br>N 4.88 |
| 77) (3β,5α,25R)-3-[(6',6"-bis[morpholin-1-yl-carbonyl]-β-D-cellobiosyl)oxy]-spirostan-12-one | | | | | | | |
| >250° C. | 1019(M + K)⁺ | $C_{49}H_{76}N_2O_{18}$ +1 $H_2O$ | calc. C found C | 58.90;<br>59.00; | H<br>H | 7.87;<br>7.93; | N 2.80<br>N 2.74 |
| 78) (3β,5α,25R)-3-[(6',6"-bis[5-methyl-isoxazol-3-ylcarbamoyl]-β-D-cellobiosyl)oxy]-spirostan-12-one | | | | | | | |
| >200° C. | 1024(M + Na)⁺ | $C_{49}H_{70}N_4O_{18}$ +1.5 $H_2O$ | calc. C found C | 56.16;<br>57.17; | H<br>H | 7.09;<br>6.96; | N 5.44<br>N 5.52 |

-continued

| Example) m.p. | Name M.S. | formula | elemental analysis | | | | | |
|---|---|---|---|---|---|---|---|---|
| 79) (3β,5α,25R)-3-[(6',6"-bis[2-methoxy-phenylcarbamoyl]-β-D-cellobiosyl)-oxy]spirostan-12-one | | | | | | | | |
| 194° C. | 1075(M + Na)⁺ +1.0 H₂O | $C_{55}H_{76}N_2O_{18}$ | calc. C found C | 61.70; 61.40; | H H | 7.28; 7.09; | N N | 2.62 2.77 |
| 80) (3β,5α,25R)-3-[(4",6"-bis[2,4-difluoro-phenylcarbamoyl]-β-D-cellobiosyl)-oxy]spirostan-12-one | | | | | | | | |
| 228.6–231.2° C. | 1087(M + Na)⁺ +1.5 H₂O | $C_{53}H_{68}F_4N_2O_{16}$ | calc. C found C | 58.32; 58.36; | H H | 6.56; 6.49; | N N | 2.57 2.55 |
| 81) (3β,5α,25R)-3-[(6"-[2,4-difluoro-phenylcarbamoyl]-β-D-cellobiosyl)oxy]-spirostan-12-one | | | | | | | | |
| 220.9° C. | 910(M + H)⁺ 932(M + Na)⁺ | HRMS calc. for $C_{46}H_{65}F_2NO_{15}Na$: | | 932.4220 found 932.4263 | | | | |
| 82) (3β,5α,25R)-3-[(4",6"-bis[phenylcarbamoyl]-β-D-cellobiosyl)oxy]-spirostan-12-one | | | | | | | | |
| >250° C. | 1015(M + Na)⁺ | $C_{53}H_{72}N_2O_{16}$ | | | | | | |
| 83) (3β,5α,25R)-3-[(4",6"-bis[benzylcarbamoyl]-β-D-cellobiosyl)oxy]spirostan-12-one | | | | | | | | |
| >220° C. | 1043(M + Na)⁺ (+1.5 H₂O) | $C_{55}H_{76}N_2O_{16}$ | calc. C found C | 63.05; 63.12; | H H | 7.54; 7.50; | N N | 2.67 2.73 |
| 84) (3β,5α,25R)-3-[(4",6"-bis[2-methyl-phenylcarbamoyl]-β-D-cellobiosyl)oxy]-spirostan-12-one | | | | | | | | |
| >220° C. | 1043(M + Na)⁺ (+3 H₂O) | $C_{55}H_{76}N_2O_{16}$ | calc. C found C | 61.47; 61.24; | H H | 7.63; 7.43; | N N | 2.61 2.58 |
| 85) (3β,5α,25R)-3-[(4",6"-bis[furan-2-yl-methylcarbamoyl]-β-D-cellobiosyl)oxy]spirostan-12-one | | | | | | | | |
| 226–230° C. (dec) | 1023(M + Na)⁺ | HRMS calc. for $C_{51}H_{72}N_2O_{18}Na$: | | 1023.4678 found 1023.4643 | | | | |
| 86) (3β,5α,25R)-3-[(4",6"-bis[methoxycarbonyl-methylcarbamoyl]-β-D-cellobiosyl)oxy]-spirostan-12 one | | | | | | | | |
| 205–210° C. (dec) | 1007(M + Na)⁺ | HRMS calc. for $C_{47}H_{72}N_2O_{20}Na$: | | 1007.4576 found 1007.4620 | | | | |
| 87) (3β,5α,25R)-3-[(4",6"-bis[2-fluoro-phenylcarbamoyl]-β-D-cellobiosyl)oxy]spirostane | | | | | | | | |
| 283–285° C. | 1037(M + Na)⁺ (+2.5 H₂O) | $C_{53}H_{72}F_2N_2O_{15}$ | Calc. C found C | 60.00 60.10; | H H | 7.27, 7.35; | N N | 2.64 2.88 |
| 88) (3β,5α,25R)-3-[([6'-dioxy-6'-fluoro-6"-(2,6-dichlorobenzoyl)]-β-D-cellobiosyl)oxy]-spirostan-12-one | | | | | | | | |
| 247° C. (dec.) | 929(M + H)⁺ (+0.5 H₂O) | $C_{46}H_{63}Cl_2FO_{14}$ | calc. C found C | 58.85; 58.91; | H H | 6.87 7.02 | | |
| 89) (3β,5α,25R)-3-[(6"-deoxy-4"-[2-fluoro-phenylcarbamoyl]-β-D-cellobiosyl)oxy]-spirostan-12-one | | | | | | | | |
| 261–266° C. | 1087(M + Na)⁺ +0.75 H₂O | $C_{48}H_{66}FNO_{14}$ | calc. C found C | 62.11; 62.03; | H H | 7.65; 7.95; | N N | 1.57 1.67 |

EXAMPLE 90

(3β,5α, 25R)-3-[(6',6"-bis[2,6-dichloro-phenylcarbamoyl]-β-D-cellobiosyl)oxy]spirostan-12-one A mixture of (3β,5α,25R)-3-[(β-D-cellobiosyl)oxy]spirostan-12-one (0.5 g, 0.663 mmol), pyridine (2 mL) and 4A molecular sieves (200 mg) were stirred at ambient temperature for 10 minutes. The mixture was cooled to 0° C. and 2,6-dichlorophenyl isocyanate was added. Dimethyl aminopyridine was added (100 mg) and the reaction was warmed to room temperature and stirred overnight. The mixture was filtered to remove the sieves and diluted with toluene (50 mL). The solution was concentrated and the residue was purified by flash chromatography (2–4% methanol/dichloromethane) to afford 130 mg (17%) of the title compound. FAB MS: 1131 (M+H)⁺; m.p. 205°–206° C.; Analysis calc. for $C_{53}H_{68}Cl_4N_2O_{16}$: C 56.29 H 6.06 N 2.48. Found: C 56.33 H 5.92 N 2.30.

EXAMPLE 91

(3β,5α,25R)-3-[(6"-[2,6-dichloro-phenylcarbamoyl]-β-D-cellobiosyl)oxy]spirostan-12-one Further eluting the column of Example 90 with 6% methanol/dichloromethane afforded a second product, 100 mg (16%) of the title compound. FAB MS 943 (M+H)⁺; m.p. 209°–210° C.; Analysis calc. for $C_{46}H_{65}Cl_2NO_{15}$: C 58.59 H 6.95 N 1.49. Found: C 58.36 H 6.86 N 1.3.

EXAMPLES 92–110

The following compounds were prepared from the appropriate starting material and isocyanate or acid chloride in an analogous manner using the above procedures.

| Example) m.p. | Name M.S. | formula | elemental analysis | | | | | |
|---|---|---|---|---|---|---|---|---|
| 92) (3β,5α,25R)-3-[(6"-[2,6-difluoro-phenylcarbamoyl]-β-D-cellobiosyl)oxy]spirostan-12-one | | | | | | | | |
| 225–226° C. | 910(M + H)⁺ | $C_{46}H_{65}F_2NO_{15}$ | calc. C | 58.40; | H | 7.35; | N | 1.48 |

-continued

| Example) m.p. | Name M.S. | formula | elemental analysis | | | | | |
|---|---|---|---|---|---|---|---|---|
| | | +2 H$_2$O | found | C | 58.73; | H | 7.23; N | 1.64 |
| 93) (3β,5α,25R)-3-[(6',6"-bis[2,6-difluoro-phenylcarbamoyl]-β-D-cellobiosyl)oxy]-spirostan-12-one | | | | | | | | |
| >250° C. | 1065(M + H)$^+$ | C$_{53}$H$_{68}$F$_4$N$_2$O$_{16}$ | calc. | C | 59.26; | H | 6.5; N | 2.61 |
| | | | found | C | 58.99; | H | 6.1; N | 2.66 |
| 94) (3β,5α,25R)-3-[(6',6"-bis[2,2,2-trifluoro-ethylcarbamoyl]-β-D-cellobiosyl)oxy]-spirostan-12-one | | | | | | | | |
| 199.9–202.9° C. | 1005(M + H)$^+$ | HRMS calc. for C$_{45}$H$_{65}$N$_2$F$_6$O$_{16}$Na: | | | | | 1027.4214 | |
| | | | found | | | | 1027.4187 | |
| 95) (3β,5α,25R)-3-[(6"-[ethoxycarbonyl-methylcarbamoyl]-β-D-cellobiosyl)-oxy]-spirostan-12-one | | | | | | | | |
| 223–224° C. | 884(M + H)$^+$ | C$_{44}$H$_{69}$NO$_{17}$ | calc. | C | 58.00; | H | 7.41; N | 2.75 |
| | | +1.5 H$_2$O | found | C | 57.62; | H | 7.40; N | 2.82 |
| 96) (3β,5α,25R)-3-[(6',6"-bis[2,6-difluoro-benzoyl]-β-D-cellobiosyl)oxy]spirostan-12-one | | | | | | | | |
| 207° C. | 1035(M + H)$^+$ | C$_{53}$H$_{66}$F$_4$O$_{16}$ | calc. | C | 60.99; | H | 6.42 | |
| | | +0.5 H$_2$O | found | C | 60.97; | H | 6.18 | |
| 97) (3β,5α,25R)-3-[(6',6"-bis[benzoyl]-β-D-cellobiosyl)oxy]spirostan-12-one | | | | | | | | |
| 205–210° C. | 963(M + H)$^+$ | C$_{53}$H$_{70}$O$_{16}$ | calc. | C | 65.48; | H | 7.36 | |
| | | +0.5 H$_2$O | found | C | 65.42; | H | 7.39 | |
| 98 (3β,5α,25R)-3-[(6"-[benzoyl]-β-D-cellobiosyl)oxy]spirostan-12-one | | | | | | | | |
| 250–251° C. | 859(M + H)$^+$ | HRMS calc. C$_{46}$H$_{66}$O$_{15}$Na: | | | | | 881.4299 | |
| | | | found | | | | 881.4387 | |
| 99) (3β,5α,25R)-3-[(6',6"-bis[2,6-dichloro-benzoyl]-β-D-cellobiosyl)oxy]-spirostan-12-one | | | | | | | | |
| 186° C. | 1101(M + H)$^+$ | C$_{53}$H$_{66}$Cl$_4$O$_{16}$ | calc. | C | 56.83; | H | 6.00 | |
| | | | found | C | 57.53; | H | 6.07 | |
| 100) (3β,5α,25R)-3-[(6"-[2,6-dichloro-benzoyl]-β-D-cellobiosyl)oxy]-spirostan-12-one | | | | | | | | |
| >230° C. | 928(M + H)$^+$ | C$_{46}$H$_{64}$Cl$_2$O$_{15}$ | calc. | C | 56.85; | H | 7.07 | |
| | | +1.5 H$_2$O | found | C | 58.01; | H | 6.95 | |
| 101) (3β,5α,25R)-3-[(6"-[4-methoxy-benzoyl]-β-D-cellobiosyl)oxy]spirostan-12-one | | | | | | | | |
| >200° C. | 888(M + H)$^+$ | C$_{47}$H$_{68}$O$_{16}$ | calc. | C | 63.53; | H | 7.65 | |
| | | | found | C | 63.34; | H | 7.66 | |
| 102) (3β,5α,25R)-3-[(6"-[2,4,6-trichloro-benzoyl]-β-D-cellobiosyl)oxy]spirostan-12-one | | | | | | | | |
| >200° C. | 962(M + H)$^+$ | C$_{46}$H$_{63}$Cl$_3$O$_{15}$ | calc. | C | 55.86; | H | 6.72 | |
| | | +1.5 H$_2$O | found | C | 55.81; | H | 6.61 | |
| 103) (3β,5α,25R)-3-[(6',6"-bis[4-methoyx-benzoyl]-β-D-cellobiosyl)oxy]spirostan-12-one | | | | | | | | |
| >200° C. | 1022(M + H)$^+$ | C$_{55}$H$_{74}$O$_{18}$ | calc. | C | 63.33; | H | 7.3 | |
| | | +1 H$_2$O | found | C | 63.50; | H | 6.92 | |
| 104) (3β,5α,25R)-3-[(6',6"-bis[4-fluoro-benzoyl]-β-D-cellobisoyl)oxy]-spirostan-12-one | | | | | | | | |
| 172–174° C. | 999(M + H)$^+$ | C$_{53}$H$_{68}$F$_2$O$_{16}$ | calc. | C | 62.62; | H | 6.89 | |
| | | +1.0 H$_2$O | found | C | 62.81; | H | 6.57 | |
| 105) (3β,5α,25R)-3-[(6"-[2-fluoro-phenylcarbamoyl]-β-D-cellobiosyl)oxy]-spirostan-12-one | | | | | | | | |
| 228–234° C. | 914(M + Na)$^+$ | HRMS calc. for C$_{46}$H$_{66}$FNO$_{15}$Na: | | | | | 914.4314 | |
| | | | found: | | | | 914.4350 | |
| 106) (3β,5α,25R)-3-[(6',6"-Bis[2-fluoro-phenylcarbamoyl]-β-D-cellobiosyl)oxy]-spirostan-12-one | | | | | | | | |
| 145–150° C. | 1051(M + N)$^+$ | C$_{53}$H$_{70}$F$_2$N$_2$O$_{16}$ | calc. | C | 60.79; | H | 6.93; N | 2.68 |
| | | +1 H$_2$O | found | C | 60.95; | H | 7.07; H | 3.04 |
| 107) (3β,5β,25S)-3-[(6"-[2-fluoro-phenylcarbamoyl]-β-D-cellobiosyl)oxy]-spirostane | | | | | | | | |
| 226–229° C. | 900(M + Na)$^+$ | C$_{45}$H$_{68}$FNO$_{14}$ | calc. | C | 60.80; | H | 7.92; N | 1.54 |
| | | +1.7 H$_2$O | found | C | 60.83; | H | 7.53; N | 1.72 |
| 108) (3β,5β,25R)-3-[(6"-[2-fluoro-phenylcarbamoyl]-β-D-cellobiosyl)oxy]-spirostane | | | | | | | | |
| 209–215° C. | 900(M + Na)$^+$ | C$_{46}$H$_{68}$FNO$_{14}$ | calc. | C | 59.85; | H | 7.97; N | 1.52 |
| | | +2.5 H$_2$O | found | C | 59.65; | H | 7.80; N | 1.88 |
| 109) (3β,5α,25R)-3-[(6"-[2-nitro-phenylcarbamoyl]-β-D-cellobiosyl)oxy]-spirostan-12-one | | | | | | | | |
| 230–231° C. | 941(M + Na)$^+$ | C$_{46}$H$_{66}$N$_2$O$_{17}$ | calc. | C | 57.85; | H | 7.39; N | 2.93 |
| | | +2 H$_2$O | found | C | 57.72; | H | 7.56; N | 3.10 |
| 110) (3β,5α,25R)-3-[(6"-[2-bromo-phenylcarbamoyl]-β-D-cellobiosyl)oxy]-spirostan-12-one | | | | | | | | |
| 179–186° C. | 975(M + Na)$^+$ | C$_{46}$H$_{66}$BrNO$_{157}$ | calc. | C | 54.87; | H | 7.21; N | 1.39 |
| | | +3 H$_2$O | found | C | 54.95; | H | 7.14; N | 1.44 |

Preparation A1

(3β,5α,25R)-3-[(4",6"-[3-oxo-pentylcarbamoyl]-2', 2",3',3",6'-penta-acetyl-β-D-cellobiosyl)oxy]-spirostan-12-one

PCC Oxidation

Pyridinium chlorochromate (577 mg, 2.68 mmol) was added to a solution of (3β,5α,25R)-3-[(4",6"-[3-hydroxy-pentylcarbamoyl]-2',2",3',3",6'-penta-acetyl-β-D-cellobiosyl)oxy]-spirostan-12-one (328 mg, 0.268 mmol) in methylene chloride (10 mL) containing dry Celite filter aid (2 g). After 18 hours at room temperature, the mixture was diluted with ether (20 mL) and the mixture was filtered through silica gel (eluting with ethyl acetate). The filtrate was concentrated and the residue was purified by flash chromatography (50% ethyl acetate/methylene chloride) to give 184 mg of the title compound as a colorless foam. FAB MS: 1241 (M+Na)$^+$.

In an analogous manner, the following compounds, Preparations A2–A3 were prepared from the appropriate starting material using the above general procedure.

Preparation A2

(3β,5α,25R)-3-[(4",6"-[2-oxo-cyclopentyl-methylcarbamoyl]-2',2",3',3",6'-penta-acetyl-β-D-cellobiosyl)oxy]-spirostan-12-one

Preparation A3

(3β,5α,25R)-3-[(6',6"-bis[2-oxo-cyclohexylcarbamoyl]-2',2",3',3",6'-penta-acetyl-β-D-cellobiosyl)oxy]-spirostan-12-one

Preparation B1

(3β,5α,25R)-3-[(4"-[2-fluoro-phenylcarbamoyl]-6"-t-butyl-dimethylsilyl-β-D-cellobiosyl)oxy]-spirostan-12-one

Deactylation of Silyl Substituted Compounds

Potassium cyanide (11 mg) was added to a solution of (3β,5α,25R)-3-[(4"-[2-fluoro-phenylcarbamoyl]-6"-t-butyl-dimethylsilyl-2',2",3',3",6' penta acetyl-β-D-cellobiosyl)oxy]-spirostan-12-one (416 mg, 0.342 mmol) in THF (5 mL) and methanol (5 mL). After 2.5 hours, the reaction was quenched by the addition of acetic acid (3 drops). The solution was purged with nitrogen and then concentrated and the residue was purified by flash chromatography (2–6% methanol/methylene chloride) to afford 96 mg product as a colorless foam. FAB MS: 1028 (M+Na)$^+$.

Preparation C1

(3β,5α,25R)-3-[(4",6"-Bis[2-methanesulfinyl-ethylcarbamoyl]-2',2",3',3",6' penta acetyl-β-D-cellobiosyl)oxy]spirostan-12-one

Preparations of Sulfoxide (3β,5α,25R)-3-[(4",6"-Bis[2-methylsulfanyl-ethylcarbamoyl]-2',2",3',3",6' penta acetyl-β-D-cellobiosyl)oxy]-spirostan-12-one (522 mg, 0.435 mmol) was dissolved in methylene chloride (9 mL). 80% 3-chloroperoxy benzoic acid was added in portions at room temperature until the starting material had been consumed (375 mg total). The mixture was diluted with ethyl acetate (30 mL) and washed with sat NaHSO$_3$ sol (1×) NaHCO$_3$ (2×) and brine (1×), dried (Na$_2$SO$_4$), filtered and concentrated in vacuo. The residue was purified by flash chromatography (5–8% methanol/methylene chloride) to afford 397 mg product as a colorless foam (75%). FAB MS: 1253 (M+Na)$^+$. $^1$H NMR (300 MHz, CDCl$_3$) δ5.15 (m,2H); 4.9 (m, 3H); 4.55 (d, 1H, J=11.0 Hz); 4.45 (d, 1H, J=14.0 Hz); 4.35 (m, 2H); 4.05 (m, 2H); 3.8–3.45 (m, 14H); 3.4 (dd, 1H, J=9.0, 8.0 Hz); 3.1–2.9 (m, 2H); 2.65 (s, 6H); 2.5 (dd, 1H, J=8.0, 7.0 Hz); 2.35 (dd, 1H, J=13.0, 12.0 Hz); 2.1 (m, 1H); 2.1 (s, 3H); 2.05 (s, 9H); 2.0 (s, 3H); 1.9–1.15 (m, 22H); 1.05 (d, 3H, J=7.0 Hz); 1.02 (s, 3H); 0.85 (s, 3H); 0.77 (d, 3H, J=7.0 Hz).

Preparation D1

(3β,5α,25R)-3-[4",6"-Bis[2-methanesulfonyl-ethylcarbamoyl]-2',2",3',3",6' penta acetyl-β-D-cellobiosyl)oxy]-spirostan-12-one

Preparation of Sulfone (3β,5α,25R)-3-[(4",6"-Bis[2-methyisulfanyl-ethylcarbamoyl]-2',2",3',3",6' penta acetyl-β-D-cellobiosyl)oxy]-spirostan-12-one (450 mg, 0.375 mmol) was dissolved in methylene chloride (8 mL). 80% 3-chloroperoxy benzoic acid was added in portions at room temperature until all of the starting material had been converted to the bis-sulfone (360 mg total over 4 hours). The mixture was diluted with ethyl acetate (30 mL) and washed with sat NaHSO$_3$ sol (1×) NaHCO$_3$ (2×) and brine (1×), dried (Na$_2$SO$_4$), filtered and concentrated in vacuo. The residue was slurried in 1:1 methanol:water and the solid was filtered, washed with water and dried to afford 436 mg product as a colorless solid (92%). FAB MS: 1285 (M+Na)$^+$. $^1$H NMR (300 MHz, CDCl$_3$) δ5.8 (m, 1H); 5.5 (m, 1H); 5.13 (m, 2H); 4.9 (m, 3H); 4.5 (d, 1H, J=11.0 Hz); 4.4 (m, 3H); 4.05 (m, 2H); 3.8–3.1 (m, 15H); 3.0 (s, 6H); 2.5 (dd, 1H, J=8.0, 7.0 Hz); 2.35 (dd, 1H, J=13.0, 12.0 Hz); 2.1 (m, 1H); 2.1 (s, 3H); 2.05 (s, 9H); 2.0 (s, 3H); 1.9–1.15 (m, 22H); 1.05 (d, 3H, J=7.0 Hz); 1.02 (s, 3H); 0.85 (s, 3H); 0.77 (d, 3H, J=7.0 Hz).

Preparation E1

(3β,5α,25R)-3-[(4",6"-Bis[2-oxo-2-pyrrolidin-1-yl-ethylcarbamoyl]-2',2",3',3",6' penta acetyl-β-D-cellobiosyl)oxy]-spirostan-12-one

Amide Formation

Dimethylaminopropyl 3-ethyl carbodiimide hydrochloride (65 mg, 0.34 mmol) and hydroxybenzotriazole (42 mg, 0.31 mmol) and pyrrolidine (64 μL, 0.77 mmol) were added to a solution of (3β,5α,25R)-3-[(4",6"-bis[carboxy-methylcarbamoyl]- 2',2",3',3",6' penta acetyl-β-D-cellobiosyl)oxy]-spirostan-12-one (180 mg, 0.154 mmol) in methylene chloride (2 mL) at room temperature. After 4 hours, the mixture was diluted with ethyl acetate (30 mL), washed with 1N HCl (2×), brine (1×), dried (Na$_2$SO$_4$), filtered and concentrated. The residue was purified by flash chromatography (4% methanol:methylene chloride) to afford 155 mg of the title compound as a colorless solid (78%). FAB MS: 1295 (M+Na)$^+$. $^1$H NMR (250 MHz, CDCl$_3$) δ5.1 (dd, 1H, J=9.0, 8.0 Hz); 5.07 (dd, 1H, J=8.0, 7.0 Hz); 4.98 (dd, 1H, J=9.0, 9.0 Hz); 4.82 (m, 2H); 4.6–3.3 (m, 27H); 2.5 (dd, 1H, J=8.0, 7.0 Hz); 2.35 (dd, 1H, J=13.0, 12.0 Hz); 2.1 (m, 1H); 2.09 (s, 3H); 2.06 (s, 3H); 2.4 (s, 3H); 2.3 (s, 3H); 2.1 (s, 3H); 1.9–1.15 (m, 30H); 1.05 (d, 3H, J=7.0 Hz); 1.02 (s, 3H); 0.85 (s, 3H); 0.77 (d, 3H, J=7.0 Hz).

In an analogous manner, the following compounds, Preparations E2–E5 were prepared from the appropriate starting material using the above general procedure.

Preparation E2

(3β,5α,25R)-3-[(4",6"-Bis[methylaminocarbonyl-methylcarbamoyl]-2',2",3',3",6' penta acetyl-β-D-cellobiosyl)oxy]-spirostan-12-one

Preparation E3

(3β,5α,25R)-3-[(4",6"-Bis[3-oxo-3-pyrrolidin-1-yl-propylcarbamoyl]-2',2",3',3",6' penta acetyl-β-D-cellobiosyl)oxy]-spirostan-12-one

Preparation E4

(3β,5α,25R)-3-[(4",6"-Bis[2-(methylaminocarbonyl)-ethylcarbamoyl]-2',2",3',3",6' penta acetyl-β-D-cellobiosyl)oxy]-spirostan-12-one

Preparation E5

(3β,5α,25R)-3-[(4",6"-Bis[2-(dimethylaminocarbonyl)-ethylcarbamoyl]-2',2",3',3",6' penta acetyl-β-D-cellobiosyl)oxy]-spirostan-12-one

Preparation F1

(3β,5α,25R)-3-[(4",6"-Bis[carboxy-methylcarbamoyl]-2',2",3',3",6' penta acetyl-β-D-cellobiosyl)oxy]-spirostan-12-one

Benzyl Ester Hydrogenolysis

10% Pd on carbon (100 mg) was added to a solution of (3β,5α,25R)-3-[(4",6"-bis[benzyloxycarbonyl-methylcarbamoyl]-2',2",3',3",6' penta acetyl-β-D-cellobiosyl)oxy]-spirostan-12-one (500 mg, 0.37 mmol) in ethyl acetate (20 mL) and methanol (5 mL). The reaction was placed under 40 psi of hydrogen and shaken in a Parr apparatus. After 3 hours, the mixture was purged with nitrogen, the catalyst removed by filtration and the filtrate concentrated to give the product as a colorless solid (400 mg, 93%). FAB MS: 1189 (M+Na)$^+$. $^1$H NMR (250 MHz, CDCl$_3$) δ7.1 (bs, 2H); 6.25 (bs, 1H); 5.9 (bs, 1H); 5.15 (m, 3H); 4.85 (m, 3H); 4.6 (m, 3H); 4.4–3.4 (m, H); 3.35 (dd, 1H, J=9.0, 8.0 Hz); 2.5 (dd, 1H, J=8.0, 7.0 Hz); 2.35 (dd, 1H, J=13.0, 12.0 Hz); 2.1 (m, 1H); 2.09 (s, 3H); 2.06 (s, 3H); 2.4 (s, 3H); 2.3 (s, 3H); 2.1 (s, 3H); 1.9–1.15 (m, 30H); 1.05 (d, 3H, J=7.0 Hz); 1.02 (s, 3H); 0.85 (s, 3H); 0.77 (d, 3H, J=7.0 Hz).

In an analogous manner, the following compound, Preparation F2 was prepared from the appropriate starting material using the above general procedure.

Preparation F2

(3β,5α,25R)-3-[(4",6"-Bis[2-carboxy-ethylcarbamoyl]-2',2",3',3",6' penta acetyl-β-D-cellobiosyl)oxy]-spirostan-12-one

Preparation G1

(3β,5α,25R)-3-[(6',6"-bis-[2-methoxy-phenylcarbamoyl]-pentaacetyl-β-D-cellobiosyl)oxy]spirostan-12-one

Carbamoylation or Acylation

A mixture of (3β,5α,25R)-3-[(2',2",3',3",4"-pentaacetyl-β-D-cellobiosyl)oxy]-spirostan-12-one (0.50 g, 0.52 mmol), methylene chloride (5 mL), triethylamine (0.51 mL, 3.63 mmol) and dimethylaminopyridine (0.10 g) was cooled to 0° C. under nitrogen atmosphere. 2-methylphenyl isocyanate (0.42 mL, 3.11 mmol) was added and the reaction was stirred at 0° C. for 15 minutes, then at room temperature for 2 hours. Upon completion, the reaction was quenched with methanol. The quenched mixture was diluted with ethyl acetate, washed 1N hydrochloric acid solution (2×), saturated sodium bicarbonate solution (1×) and brine (1×), dried over sodium sulfate, filtered and concentrated in vacuo. The residual material was flash chromatographed (50% ethyl acetate/hexanes) to afford 0.64 g (97% yield) of the titled compound.

$^1$HNMR (250 MHz, CDCl$_3$) δ7.4 (s, 1H); 7.3 (s, 1H); 7.1–6.8 (m, 8H); 5.25–3.3 (m, 24H); 2.6–1.1 (m, 40H); 1.05 (d, 3H, J=7); 1.0 (s, 3H); 0.8 (s, 3H); 0.75 (d, 3H, J=7).

In an analogous manner the following compounds, Preparations G2–G25, were prepared from the appropriate starting material using the above general procedure.

Preparation G2

(3β,5α,25R)-3-[(6',6"-bis[phenylcarbamoyl]-pentaacetyl-β-D-cellobiosyl)oxy]spirostan-12-one

Preparation G3

(3β,5α,25R)-3-[(6',6"-bis[2,4-difluoro-phenylcarbamoyl]-pentaacetyl-β-D-cellobiosyl)oxy]spirostan-12-one

Preparation G4

(3β,5α,25R)-3-[(6',6"-bis[pivaloyl]-pentaacetyl-β-D-cellobiosyl)oxy]spirostan-12-one

Preparation G5

(3β,5α,25R)-3-[(6',6"-bis[ethoxycarbonyl-methylcarbamoyl]-pentaacetyl-β-D-cellobiosyl)oxy)]spirostan-12-one

Preparation G6

(3β,5α,25R)-3-[(6',6"-bis[4-nitro-phenylcarbamoyl]-pentaacetyl-β-D-cellobiosyl)oxy]spirostan-12-one

Preparation G7

(3β,5α,25R)-3-[(6',6"-bis[2-trifluoromethyl-phenylcarbamoyl]-pentaacetyl-β-D-cellobiosyl)oxy]spirostan-12-one

Preparation G8

(3β,5α,25R)-3-[(6',6"-bis[5-methyl-isoxazol-3-ylcarbamoyl]-pentaacetyl-β-D-cellobiosyl)oxy]spirostan-12-one

Preparation G9

(3β,5α,25R)-3-[(4",6"-bis[2,4-difluoro-phenylcarbamoyl]-pentaacetyl-β-D-cellobiosyl)oxy]spirostan-12-one

Preparation G10

(3β,5α,25R)-3-[(6"-[2,4-difluoro-phenylcarbamoyl]-hexaacetyl-β-D-cellobiosyl)oxy]spirostan-12-one

Preparation G11

(3β,5α,25R)-3-[(4",6"-bis[4-nitro-phenylcarbamoyl]-pentaacetyl-β-D-cellobiosyl)oxy]spirostan-12-one

Preparation G12

(3β,5α,25R)-3-[(4",6"-bis[phenylcarbamoyl]-pentaacetyl-β-D-cellobiosyl)oxy]spirostan-12-one

Preparation G13

(3β,5α,25R)-3-[(4",6"-bis[benzylcarbamoyl]-pentaacetyl-β-D-cellobiosyl)oxy]spirostan-12-one

Preparation G14

(3β,5α,25R)-3-[(4",6"-bis[2-methyl-phenylcarbamoyl]-pentaacetyl-β-D-cellobiosyl)oxy]spirostan-12-one

Preparation G15

(3β,5α,25R)-3-[(4",6"-bis[4-acetyl-phenylcarbamoyl]-2',2",3',3",6'-penta-acetyl-β-D-cellobiosyl)oxy]spirostan-12-one

Preparation G16

(3β,5α,25R)-3-[(4",6"-bis[3-acetyl-phenylcarbamoyl]-2',2",3',3",6'-penta-acetyl-β-D-cellobiosyl)oxy]spirostan-12-one

Preparation G17

(3β,5α,25R)-3-[(6"-[3,5-dimethoxy-phenylcarbamoyl]-2',2",3',3",6'-penta-acetyl-β-D-cellobiosyl)oxy]spirostan-12-one

Preparation G18

(3β,5α,25R)-3-[(4"-[2-fluorphenyl carbamoyl]-2',2",3',3",6'-penta-acetyl-6"-tert-butyl dimethyl silyl-β-D-cellobiosyl)oxy]spirostan-12-one

Preparation G19

(3β,25R)-3-[(4",6"-bis[2-fluoro-phenylcarbamoyl]-2',2",3',3",6'-penta-acetyl-β-D-cellobiosyl)oxy]-5-spirostene

Preparation G20

(3β,5α,25R)-3-[(4",6"-bis[3-methoxy-phenylcarbamoyl]-2',2",3',3",6'-penta-acetyl-β-D-cellobiosyl)oxy]spirostan-12-one

Preparation G21

(3β,5α,25R)-3-[(4",6"-bis[2-fluoro-phenylcarbamoyl]-2',2",3',3",6'-penta-acetyl-β-D-cellobiosyl)oxy]spirostan-12-one

Preparation G22

(3β,5α,25R)-3-[(6"-[2-fluoro-phenylcarbamoyl]-2',2",3',3",6'-penta-acetyl-β-D-cellobiosyl)oxy]spirostan-12-one

Preparation G23

(3β,5α,25R)-3-[(6"-deoxy-4"-[2-fluorophenylcarbamoyl]-2',2",3',3",6'-penta-acetyl-β-D-cellobiosyl)oxy]spirostan-12-one

Preparation G24

(3β,5α,25R)-3-[(6"-benzamido-6"-deoxy-2',2",3',3",6'-penta-acetyl-β-D-cellobiosyl)oxy]spirostan-12-one

Preparation G25

(3β,5α,25R)-3-[(6"-deoxy-6"-[3(2-fluorophenyl)ureido]-2',2",3',3",6'-penta-acetyl-β-D-cellobiosyl)oxy]spirostan-12-one

Preparation H1

(3β,5α,25R)-3-[(4",6"-bis-[furan-2-yl-methylcarbamoyl]-pentaacetyl-β-D-cellobiosyl)oxy]spirostan-12-one Carbamoylation Using Carbonyl Diimidazole A mixture of (3β,5α,25R)-3-[(2',2",3',3",6"-pentaacetyl-β-D-cellobiosyl)oxy]spirostan-12-one (0.50 g, 0.52 mmol), carbonyl diimidazole (0.21 g, 1.30 mmol) and diisopropylethylamine (0.45 mL, 2.59 mmol) in dichloromethane (5 mL) was stirred at room temperature for 2 hours. Furfurylamine (0.23 mL, 2.59 mmol) was added and the reaction mixture was stirred for 3 hours at room temperature. Upon completion, the reaction was diluted with ethyl acetate, washed with 1N hydrochloric acid (2×), saturated sodium bicarbonate solution (1×) and brine (1×), dried over anhydrous sodium sulfate, filtered and concentrated in vacuo.

The crude product was flash chromatographed (60% ethyl acetate/hexanes) to afford 0.40 g (64%) of the titled compound. $^1$HNMR (250 MHz, CDCl$_3$) δ7.4–7.3 (m, 4H); 6.35–6.15 (m, 8H); 5.5–3.4 (m, 17H); 3.3 (t, 1H, J=10); 2.6–1.1 (m, 40H); 1.05 (d, 3H, J=7); 1.0 (s, 3H); 0.9 (s, 3H); 0.8 (d, 3H, J=7). In an analogous manner the following compounds, Preparations H2–H40, were prepared from the appropriate starting material using the above general procedure.

Preparation H2

(3β,5α,25R)-3-[(4",6"-bis[methoxycarbonyl-methylcarbamoyl]-pentaacetyl-β-D-cellobiosyl)oxy]spirostan-12-one

Preparation H3

(3β,5α,25R)-3-[(6',6"-bis[morpholin-1-yl-carbonyl]-pentaacetyl-β-D-cellobiosyl)oxy]spirostan-12-one

Preparation H4

(3β,5α,25R)-3-[(4",6"-bis[3-dimethylamino-phenylcarbamoyl]-2',2",3',3",6'-penta-acetyl-β-D-cellobiosyl)oxy]spirostan-12-one

Preparation H5

(3β,5α,25R)-3-[(4",6"-bis[4-methyl-piperidin-2-yl-carbonyl]-2',2",3',3",6'-penta-acetyl-β-D-cellobiosyl)oxy]spirostan-12-one preparation H6

(3β,5α,25R)-3-[(4",6"-bis[pyrrolidin-1-yl carbonyl]-2',2",3',3",6'-penta-acetyl-β-D-cellobiosyl)oxy]spirostan-12-one

Preparation H7

(3β,5α,25R)-3-[(6"-[indolin-1-yl carbonyl]-2',2",3',3",6'-penta-acetyl-β-D-cellobiosyl)oxy]spirostan-12-one

Preparation H8

(3β,5α,25R)-3-[(4",6"-bis[pyridin-2-yl-methylcarbamoyl]-2',2",3',3",6'-penta-acetyl-β-D-cellobiosyl)oxy]spirostan-12-one

Preparation H9

(3β,5α,25R)-3-[(6"-bis[pyridin-2-yl-methylcarbamoyl]-2',2",3',3",6'-penta-acetyl-β-D-cellobiosyl)oxy]spirostan-12-one

Preparation H10

(3β,5α,25R)-3-[(6',6"-bis[trans-2-hydroxy-cyclohexylcarbamoyl]-2',2",3',3",6'-penta-acetyl-β-D-cellobiosyl)oxy]spirostan-12-one

Preparation H11

(3β,5α,25R)-3-[(4",6"-bis[2-ethoxycarbonyl-ethylcarbamoyl]-2',2",3',3",6'-penta-acetyl-β-D-cellobiosyl)oxy]spirostan-12-one

Preparation H12

(3β,5α,25R)-3-[(4",6"-bis[2-methoxy-ethylcarbamoyl]-2',2",3',3",6'-penta-acetyl-β-D-cellobiosyl)oxy]spirostan-12-one

Preparation H13

(3β,5α,25R)-3-[(4",6"-bis[ethoxycarbonylmethyl-methyl-carbamoyl]-2',2",3',3",6'-penta-acetyl-β-D-cellobiosyl)oxy]spirostan-12-one

Preparation H14

(3β,5α,25R)-3-[(6"-[methoxycarbonyl-propylcarbamoyl]-2',2",3',3",6'-penta-acetyl-β-D-cellobiosyl)oxy]spirostan-12-one

Preparation H15

(3β,5α,25R)-3-[(4",6"-bis[1,2-bis(methoxycarbonyl)-ethylcarbamoyl]-2',2",3',3",6'-penta-acetyl-β-D-cellobiosyl)oxy]spirostan-12-one

Preparation H16

(3β,5α,25R)-3-[(4",6"-bis[2-methoxycarbonyl-ethylcarbamoyl]-2',2",3',3",6'-penta-acetyl-β-D-cellobiosyl)oxy]spirostan-12-one

Preparation H17

(3β,5α,25R)-3-[(4",6"-bis[t-butoxycarbonyl-ethylcarbamoyl]-2',2",3',3",6'-penta-acetyl-β-D-cellobiosyl)oxy]spirostan-12-one

Preparation H18

(3β,5α,25R)-3-[(4",6"-bis[1-thiophen-2-yl-ethylcarbamoyl]-2',2",3',3",6'-penta-acetyl-β-D-cellobiosyl)oxy]spirostan-12-one

Preparation H19

(3β,5α,25R)-3-[(4",6"-bis[3-hydroxy-propylcarbamoyl]-2',2",3',3",6'-penta-acetyl-β-D-cellobiosyl)oxy]spirostan-12-one

Preparation H20
(3β,5α,25R)-3-[(4",6"-bis[thiphen-2-yl-methylcarbamoyl]-2',2",3',3",6'-penta-acetyl-β-D-cellobiosyl)oxy]spirostan-12-one

Preparation H21
(3β,5α,25R)-3-[(4",6"-bis[2-methoxycarbonyl-propylcarbamoyl]-2',2",3',3",6'-penta-acetyl-β-D-cellobiosyl)oxy]spirostan-12-one

Preparation H22
(3β,5α,25R)-3-[(4",6"-bis[ethoxycarbonyl-methylcarbamoyl]-2',2",3',3",6'-penta-acetyl-β-D-cellobiosyl)oxy]spirostan-12-one

Preparation H23
(3β,5α,25R)-3-[(4",6"-bis[2-methylsulfanyl-ethylcarbamoyl]-2',2",3',3",6'-penta-acetyl-β-D-cellobiosyl)oxy]spirostan-12-one

Preparation H24
(3β,5α,25R)-3-[(4",6"-bis[4-nitro-benzylcarbamoyl]-2',2",3',3",6'-penta-acetyl-β-D-cellobiosyl)oxy]spirostan-12-one

Preparation H25
(3β,5α,25R)-3-[(4",6"-bis[3-fluoro-benzylcarbamoyl]-2',2",3',3",6'-penta-acetyl-β-D-cellobiosyl)oxy]spirostan-12-one

Preparation H26
(3β,5α,25R)-3-[(4",6"-bis[2-methoxycarbonyl-2-methyl-propylcarbamoyl]-2',2",3',3",6'-penta-acetyl-β-D-cellobiosyl)oxy]spirostan-12-one

Preparation H27
(3β,5α,25R)-3-[(4",6"-bis[3-ethoxycarbonyl-propylcarbamoyl]-2',2",3',3",6'-penta-acetyl-β-D-cellobiosyl)oxy]spirostan-12-one

Preparation H28
(3β,5α,25R)-3-[(4",6"-bis[trans-2-hydroxy-cyclopentyl methylcarbamoyl]-2',2",3',3",6'-penta-acetyl-β-D-cellobiosyl)oxy]spirostan-12-one

Preparation H29
(3β,5α,25R)-3-[(4",6"-bis[2-methoxycarbonyl-butylcarbamoyl]-2',2",3',3",6'-penta-acetyl-β-D-cellobiosyl)oxy]spirostan-12-one

Preparation H30
(3β,5α,25R)-3-[(4",6"-bis[1-methoxycarbonyl-cyclopropyl-methylcarbamoyl]-2',2",3',3",6'-penta-acetyl-β-D-cellobiosyl)oxy]spirostan-12-one

Preparation H31
(3β,5α,25R)-3-[(4",6"-bis[2-methoxycarbonyl-1-methyl-ethylcarbamoyl]-2',2",3',3",6'-penta-acetyl-β-D-cellobiosyl)oxy]spirostan-12-one

Preparation H32
(3β,5α,25R)-3-[(4",6"-bis[thiazol-2-yl-methylcarbamoyl]-2',2",3',3",6'-penta-acetyl-β-D-cellobiosyl)oxy]spirostan-12-one

Preparation H33
(3β,5α,25R)-3-[(4",6"-bis[4,5-dimethyl-thiazol-2-yl-methylcarbamoyl]-2',2",3',3",6'-penta-acetyl-β-D-cellobiosyl)oxy]spirostan-12-one

Preparation H34
(3β,5α,25R)-3-[(4",6"-bis[3-ethoxycarbonylpiperidin-1-yl-carbonyl]-2',2",3',3",6'-penta-acetyl-β-D-cellobiosyl)oxy]spirostan-12-one

Preparation H35
(3β,5α,25R)-3-[(4",6"-bis[benzyloxycarbonyl-methylcarbamoyl]-2',2",3',3",6'-penta-acetyl-β-D-cellobiosyl)oxy]spirostan-12-one

Preparation H36
(3β,5α,25R)-3-[(4",6"-bis[2-benzyloxycarbonyl-ethylcarbamoyl]-2',2",3',3",6'-penta-acetyl-β-D-cellobiosyl)oxy]spirostan-12-one

Preparation H37
(3β,5α,25R)-3-[(4",6"-bis[3-hydroxy-pentylcarbamoyl]-2',2",3',3",6'-penta-acetyl-β-D-cellobiosyl)oxy]spirostan-12-one

Preparation H38
(3β,5α,25R)-3-[(4",6"-bis[2-methoxycarbonyl-2-phenyl-ethylcarbamoyl]-2',2",3',3",6'-penta-acetyl-β-D-cellobiosyl)oxy]spirostan-12-one

Preparation H39
(3β,5α,25R)-3-[(4",6"-bis[thiophen-2-yl-methyl-thiocarbamoyl]-2',2",3',3",6'-penta-acetyl-β-D-cellobiosyl)oxy]spirostan-12-one

Preparation H40

(3β,5α,25R)-3-[(4",6"-bis[2-fluoro-phenylcarbamoyl]-2',2",3',3",6',-penta-acetyl-β-D-cellobiosyl)oxy]spirostan-12-acetaoxy-spirostane

Preparation I1

(3β,5α,25R)-3-[(4",6"-Bis[2-fluoro-phenylcarbamoyl]-2',2",3',3",6'-penta-acetyl-β-D-cellobiosyl)oxy]spirostan-12-one

Carbamoylation Using Cuprous Chloride Catalysis

Cuprous chloride (3.48 g, 36 mmol) was added to a solution of (3β,5α,25R)-3-[(2',2",3',3",6"-penta-chloroacetyl-β-D-cellobiosyl)oxy]-spirostan-12-one (10.0 g, 8.8 mmol) and 2-fluorophenylisocyanate (4 mL, 36 mmol) in dry dimethyl formamide (60 mL) at room temperature. After 3 hours, the mixture was diluted with ethyl acetate (100 mL) and washed with 1N HCl (2×) and brine (1×), dried (Na$_2$SO$_4$) filtered and concentrated in vacuo. The residue was dissolved in methylene chloride (50 mL) and methanol (75 mL) was added. The methylene chloride was removed in vacuo and a solid precipitated from the methanol. The solid was filtered, washed with methanol and dried to afford 10.6 g product as a colorless solid (86%). m.p. 212°–214° C. FAB MS: 1433 (M+Na)$^+$. $^1$H NMR (250 MHz, CDCl$_3$) δ7.9 (m, 2H); 7.05 (m, 8H); 5.35 (dd, 1H, J=8.0, 7.0 Hz); 5.28 (dd, 1H, J=9.0, 8.0 Hz); 5.15 (dd, 1H, J=9.0, 9.0 Hz); 5.05 (dd, 1H, J=9.0, 8.0 Hz); 4.98 (dd, 1H, J=8.0, 7.0 Hz); 4.72 (d, 1H, J=9.0 Hz); 4.6 (m, 3H); 4.4–3.4 (m, 18H); 3.35 (dd, 1H, J=10.0, 9.0 Hz); 2.5 (dd, 1H, J=8.0, 7.0 Hz); 2.35 (dd, 1H, J=13.0, 12.0 Hz); 2.1 (m, 1H); 2.1–1.1 (m, 22H); 1.05 (d, 3H, J=7.0 Hz); 1.02 (s, 3H); 0.85 (s, 3H); 0.77 (d, 3H, J=7.0 Hz).

Preparation J1

(3β,5α,25R)-3-[(4",6"-Bis[trans-2-ethoxycarbonyl-cyclopropylcarbamoyl]-2',2",3',3",6'-penta-acetyl-β-D-cellobiosyl)oxy]spirostan-12-one

Carbamoylation Using Dibutyl Tin Dilaurate Catalysis (3β,5α,25R)-3-[(6"-2',2",3',3",6"-pentaacetyl-β-D-cellobiosyl)oxy]-spirostan-12-one (244 mg, 0.253 mmol) was added to a solution of freshly prepared trans-2-carboethoxy-cyclopropyl isocyanate (~2.53 mmol) in toluene (10 mL). Dibutyl tin dilaurate (0.11 mL, 0.19 mmol) was added and the reaction stirred for 48 hours. The solvent volume was reduced in vacuo to 2 mL and the product precipitated with hexanes. The solid was filtered and purified by flash chromatography (50% ethyl acetate:methylene chloride) to afford 154 mg product as an off-white solid. FAB MS: 1297 (M+Na)$^+$.

In an analogous manner, the following compounds, Preparation J2 and J3 were prepared from the appropriate starting material using the above general procedure.

Preparation J2

(3β,5α,25R)-3-[(4",6"-Bis[3-oxo-butylcarbamoyl]-2',2",3',3",6'-penta-acetyl-β-D-cellobiosyl)oxy]spirostan-12-one

Preparation J3

(3β,5α,25R)-3-[(4",6"-bis[trans-2-methoxycarbonyl-cyclopentylcarbamoyl]-2',2",3',3",6'-penta-acetyl-β-D-cellobiosyl)oxy]spirostan-12-one

Preparation K1

(3β,5α,25R)-3-[(6',6"-dideoxy]-pentaacetyl-β-D-cellobiosyl)oxy]spirostan

Deiodization

To a solution of (3β,5α,25R)-3-[(6',6"-dideoxy-6',6"-diiodo-pentaacetyl-β-D-cellobiosyl)oxy]spirostane (150 mg, 0.128 mmol) and tri-n-butyl tin hydride (0.105 mL, 0.39 mmol) in anhydrous toluene (5 mL), azoisobutyrylnitrile (10 mg) was added at room temperature. The reaction mixture was gently refluxed under nitrogen atmosphere for 3 hours, cooled and concentrated in vacuo. The residual material was triturated with hexanes, filtered and dried to afford 75 mg (64% yield) of a colorless solid. $^1$HNMR (250 MHz, CDCl$_3$) δ5.2–4.3 (m, 13H); 3.6–3.3 (m, 7H); 2.2–1.0 (m, 42H); 0.95 (d, 3H, J=7); 0.82–0.70 (m, 9H). FAB MS: 919 (M+H)$^+$.

Preparation L1

(3β,5α,25R)-3-[(6',6"-dideoxy-6',6"-difluoro-pentaacetyl-β-D-cellobiosyl)oxy]spirostan

Fluorination

To a solution of (3β,5α,25R)-3-[(2',2",3',3",4"-pentaacetyl-β-D-celiobiosyl)oxy]-spirostane (750 mg, 0.79 mmol) in anhydrous dimethoxyethane (3 mL), diethylamino sulfur trifluoride (0.833 mL, 6.30 mmol) was added at 0° C. After 15 minutes, the reaction was warmed to room temperature, then heated to a gentle reflux for 3 hours. Upon completion, the reaction was cooled and poured into ice water. The product was extracted with ethyl acetate (50 mL) and washed with 0.1N hydrochloric acid solution (1×), sodium bicarbonate solution (1×) and brine (1×), dried over sodium sulfate, filtered and concentrated in vacuo. The crude product was purified via flash chromatography (35% ethyl acetate/hexanes) to afford 350 mg (45%) of a colorless solid. $^1$HNMR (250 MHz, CDCl$_3$) δ5.25–3.3 (m, 18H); 2.1–1.0 (m, 42H); 0.95 (d, 3H, J=7); 0.8 (s, 3H); 0.8 (d, 3H, J=7); 0.75 (s, 3H).

In an analogous manner the following compounds, Preparations L2–L4, were prepared from the appropriate starting material using the above general procedure.

Preparation L2

(3β,5α,25R)-3-[(6',6"-dideoxy-6',6"-difluoro-pentaacetyl-β-D-cellobiosyl)oxy]spirostan-12-one

Preparation L3

(3β,5α,25R)-3-[(6"-deoxy-6"-fluoro-hexaacetyl-β-D-cellobiosyl)oxy]spirostan-12-one

Preparation L4

(3β,5α,25R)-3-[(6'-deoxy-6'-fluoro-hexaacetyl-β-D-cellobiosyl)oxy]spirostan-12-one

Preparation M1

(3β,5α,25R)-3-[(6',6"-dideoxy-6',6"-dichloro-
pentaacetyl-β-D-cellobiosyl)oxy]spirostan-12-one

Chlorination

A mixture of (3β,5α,25R)-3-[(6',6"-dimesyl-pentaacetyl-β-D-cellobiosyl)oxy]-spirostan-12-one (3.00g, 2.68 mmol), lithium chloride (3.25 g) and N,N-dimethylformamide (40 mL) was heated to 85° C. and stirred for 1 hour. The reaction was then cooled, diluted with ethyl acetate, washed with water (2×) and brine (1×), dried over sodium sulfate, filtered and concentrated in vacuo. The residual material was triturated with hexanes, filtered and dried to afford 2.28 g (82.3%) of a colorless solid.

$^1$HNMR (250 MHz, CDCl$_3$) δ5.2–3.45 (m, 17H); 3.35 (t, 1H, J=10); 2.6–1.15 (m, 40H); 1.05 (d, 3H, J=7 Hz); 1.0 (s, 3H); 0.9 (s, 3H); 0.8 (d, 3H, J=7 Hz).

In an analogous manner the following compound, Preparation M2, was prepared from the appropriate starting material using the above general procedure.

Preparation M2

(3β,5α,25R)-3-[(6',6"-dideoxy-6',6"-dichloro-
pentaacetyl-β-D-lactosyl)oxy]spirostan-12-one

Preparation N1

(3β,5α,25R)-3-[(6',6"-dideoxy-6',6"-diiodo-
pentaacetyl-β-D-cellobiosyl)oxy]spirostan

Iodization

A mixture of (3β,5α,25R)-3-[(2',2",3',3",4"-pentaacetyl-β-D-cellobiosyl)oxy]spirostane (1.00 g, 1.05 mmol), imidazole (0.43 g, 6.38 mmol),and triphenylphosphine (1.65 g, 6.38 mmol) was dissolved in toluene (20 mL). Iodine (1.06 g, 4.20 mmol) was added and the reaction was gently refluxed for 3 hours. Upon completion, the reaction was cooled, diluted with ethyl acetate, washed with 1N hydrochloric acid (1×), sodium bicarbonate solution (1×) and brine (1×), dried over sodium sulfate, filtered and concentrated in vacuo. The crude product was purified via flash chromatography (30% ethyl acetate/methylene chloride) to afford 0.53 g (43%) of a colorless solid.

$^1$HNMR (250 MHz, CDCl$_3$) δ5.3–3.0 (m, 18H); 2.2–1.0 (m, 42H); 0.95 (d, 3H, J=7 Hz); 0.80 (s, 3H); 0.75 (d, 3H, J=7 Hz); 0.70 (s, 3H). FAB MS: 1171 (M+H)$^+$.

Preparation O1

(3β,5α,25R)-3-[(6',6"-dideoxy-6',6"-diamino-
pentaacetyl-β-D-cellobiosyl)oxy]spirostan

Pd/C Catalyzed Reduction

A solution of (3β,5α,25R)-3-[([6',6"-diazidopentaacetyl-β-D-cellobiosyl)oxy]-spirostane (1.6 g, 1.6 mmol) in ethyl acetate (15 mL) and ethanol (20 mL) was added to a Parr flask. Nitrogen was bubbled through the system for 2 minutes. 10% Pd/C (100 mg) was added and the flask was put on the Parr shaker at 30 psi for 6 hours. TLC, at this point showed very little reaction, so more catalyst (100 mg) and acetic acid (1 mL) were added to the system. The reaction was shaken for an additional 24 hours at 30 psi. Though not complete, the reaction was purged with nitrogen and filtered through a millipore filtration system. The filtrate was concentrated in vacuo, then purified via flash chromatography (2 to 6% methanol/methylene chloride) to afford 600 mg (40%) of product as an off-white solid.

In an analogous manner the following compound, Preparation O2, was prepared from the appropriate starting material using the above general procedure.

Preparation O2

(3β,5α,25R)-3-[([6',6"-dideoxy-6',6"-
diaminopentaacetyl]-β-D-cellobiosyl)oxy]spirostan-
12-one

Preparation P1

(3β,5α,25R)-3-[(6',6"-dideoxy-6',6"-diazido-
pentaacetyl-β-D-cellobiosyl)oxy]spirostan-12-one

Azide Displacement (3β,5α,25R)-3-[(6',6"-dimesyl-pentaacetyl-β-D-cellobiosyl)oxy]spirostan-12-one (0.60 g; 0.54 mmol) was dissolved in N,N,-dimethylformamide (8 mL). To this solution, sodium azide (0.19 mL; 5.35 mmol) was added. The reaction was heated to 100° C. and was stirred for 5 hours under nitrogen atmosphere. The reaction was then cooled, diluted with ethyl acetate, washed with water (2×) and brine (1×), dried over sodium sulfate, filtered and concentrated in vacuo. The crude product was purified via flash chromatography (40% ethyl acetate/hexanes) to afford 0.38 g (70%) of white solid. $^1$HNMR (250 MHz, CDCl$_3$) δ5.26–3.25 (m, 18H); 2.6–1.15 (m, 40H); 1.05 (d, 3H, J=7); 1.02 (s, 3H); 0.85 (s, 3H); 0.8 (d, 3H, J=7).

In an analogous manner the following compound, Preparation P2, was prepared from the appropriate starting material using the above general procedure.

Preparation P2

(3β,5α,25R)-3-[(6',6"-dideoxy-6',6"-diazido-
pentaacetyl-β-D-cellobiosyl)oxy]spirostane

Preparation Q1

(3β,5α,25R)-3-[(6',6"-dimesyl-pentaacetyl-β-D-
cellobiosyl)oxy]spirostan-12-one

Mesylation

A solution of (3β,5α,25R)-3-[(2',2",3',3",4"-pentaacetyl-β-D-cellobiosyl)oxy]spirostan-12-one (3.50 g, 3.63 mmol) and triethylamine (5.10 mL, 36.00 mmol) in dichloromethane (30 mL) was cooled to 0° C. Mesyl chloride (1.59 mL, 22.00 mmol) and dimethylaminopyridine (1.00 g) were added and the reaction was stirred at 0° C. for 2 hours. The reaction was diluted with ethyl acetate, washed with 1N hydrochloric acid solution (2×), sodium bicarbonate solution (1×) and brine (1×), dried over sodium sulfate, filtered and concentrated in vacuo. The residual material was dissolved in dichloromethane and hexanes were added. The dichloromethane was removed in vacuo and the resulting precipitate was filtered, washed with hexanes and dried under vacuum to afford 3.61 g (88.8%) of a colorless solid.

¹HNMR (250 MHz, CDCl₃) δ5.25–3.3 (m, 18H); 3.1 (d, 6H, J=7 Hz); 2.6–1.1 (m, 40H); 1.0 (s, 3H); 0.95 (d, 3H, J=7 Hz); 0.77 (d, 3H, J=7 Hz); 0.7 (s, 3H).

In an analogous manner the following compounds, Preparations Q2–Q3, were prepared from the appropriate starting material using the above general procedure.

Preparation Q2

(3β,5α,25R)-3-[(6',6''-dimesylpentaacetyl-β-D-cellobiosyl)oxy]spirostan-12-one

Preparation Q3

(3β,5α,25R)-3-[(6',6''-dimesyl-pentaacetyl-β-D-cellobiosyl)oxy]spirostane

Preparation R1

(3β,5α,25R)-3-[(6''-deoxy-2',2'',3',3''6'-diazido-penta-acetyl-β-D-cellobiosyl)oxy]spirostan-12-one 2,2'-Azo-bis-(2-methyl)propionitrile (60 mg) was added to a solution of tri-n-butyl tin hydride (0.393 mL, 1.46 mmol) and (3β,5α,25R)-3-[(6''-bromo-6''-deoxy-2',2'',3',3'', 6''-pentaacetyl-β-D-cellobiosyl)oxy]-spirostan-12-one (1.0 g, 0.973 mmol) dry toluene (30 mL) at room temperature. The mixture was heated to a gentle reflux for 3 hours, was cooled and concentrated in vacuo. The product was triturated with hexanes, filtered and washed with hexanes, and the solid was purified by flash chromatography (50% ethyl acetate/hexanes) to afford 0.37 g of the title compound as a colorless solid (40%). FAB MS: 971 (M+Na)⁺. ¹H NMR (300 MHz, CDCl₃) δ5.15 (dd, 1H, J=10.0, 9.0 Hz); 4.85 (m, 3H); 4.5 (d, 1H, J=11.0 Hz); 4.45 (m, 2H); 4.35 (m, 1H); 4.05 (dd, 1H, J=12.0, 6.0 Hz); 3.7 (dd, 1H, J=9.0, 8.0 Hz); 3.6–3.3 (m, 6H); 2.5 (dd, 1H, J=8.0, 7.0 Hz); 2.4 (d, 1H, J=5.0 Hz); 2.35 (dd, 1H, J=13.0, 12.0 Hz); 2.15 (m, 1H); 2.1 (s, 3H; 2.08 (s, 3H); 2.03 (s, 9H); 2.0–1.1 (m, 26H); 1.05 (d, 3H, J=7.0 Hz); 1.02 (s, 3H); 0.85 (s, 3H); 0.77 (d, 3H, J=7.0 Hz).

Preparation S1

(3β,5α,25R)-3-[(6''-amino-6''-deoxy-2',2'',3',3'',6'-penta-acetyl-β-D-cellobiosyl)oxy]-spirostan-12-one Azide Reduction (3β,5α,25R)-3-[(6''-azido-6''-deoxy-2',2'',3',3'',6''-pentaacetyl-β-D-cellobiosyl)oxy]-spirostan-12-one (966 mg, 0.976 mmol) was added as a solution in THF (3 mL) to a solution of stannous chloride (277 mg, 1.46 mmol) in methanol (10 mL) containing 90 mg of aluminum chloride. After stirring overnight at room temperature, the mixture was diluted with ethyl acetate (30 mL) and washed with NaHCO₃ sol (2×) and brine (1×), dried (Na₂SO₄) filtered and concentrated. The residue was purified by flash chromatography (5% methanol/methylene chloride) to afford 435 mg product as a colorless solid (46%) FAB MS: 986 (M+Na)⁺.

Preparation T1

(3β,5α,25R)-3-[(6''-azido-6''-deoxy-2',2'',3',3'',6'-pentaacetyl-β-D-cellobiosyl)oxy]-spirostan-12-one Bromide Displacement with Sodium Azide Sodium azide (240 mg, 3.69 mmol) was added to a solution of (3β,5α,25R)-3-[(6''-bromo-6''-deoxy-2',2'',3',3'', 6''-pentaacetyl-β-D-cellobiosyl)oxy]-spirostan-12-one (1.0 g, 0.923 mmol) in dry DMF (10 mL) at room temperature. The mixture was heated to 60° C. for 5 hours, cooled, and diluted with ethyl acetate (100 mL). The mixture was washed with water (3×) and brine (1×), dried (Na₂SO₄) filtered and concentrated in vacuo. The product was triturated from ethyl acetate/hexanes, filtered and dried to afford 916 mg of the title product as a colorless solid (100%).

FAB MS: 1012 (M+Na)⁺. ¹H NMR (250 MHz, CDCl₃) δ5.15 (dd,1H,J=9.0, 8.0 Hz); 4.90 (m, 3H); 4.5 (m, 3H); 4.3 (m, 1H); 4.1 (dd, 1H, J=12.0, 6.0 Hz); 3.75 (dd, 1H, J=8.0, 7.0 Hz); 3.7–3.40 (m, 6H); 3.35 (dd, 1H, J=8.0, 8.0 Hz); 2.72 (d, 1H, J=5.0 Hz); 2.5 (dd, 1H, J=8.0, 7.0 Hz); 2.4 (d, 1H, J=5.0 Hz); 2.35 (dd, 1H, J=13.0, 12.0 Hz); 2.15 (m, 1H); 2.1 (s, 3H); 2.08 (s, 3H); 2.06 (s, 3H); 2.03 (s, 3H); 2.02 (s, 3H); 2.0–1.1 (m, 21H); 1.05 (d, 3H, J=7.0 Hz); 1.02 (s, 3H); 0.85 (s, 3H); 0.77 (d, 3H, J=7.0 Hz).

Preparation U1

(3β,5α,25R)-3-[(6''-bromo-6''-deoxy-2',2'',3',3'',6'-pentaacetyl-β-D-cellobiosyl)oxy]-spirostan-12-one Bromination Carbon tetrabromide (0.72 g, 2.2 mmol), triphenyl phosphine (1.36 g, 5.2 mmol) and pyridine (0.64 mL, 8 mmol) were added to a solution of (3β,5α,25R)-3-[(2',2'',3',3'',6''-pentaacetyl-β-D-cellobiosyl)oxy]-spirostan-12-one (2.0 g, 2.08 mmol) in methylene chloride (15 mL) at room temperature. After 24 hours, the reaction was quenched by the addition of methanol (1 mL), diluted with ethyl acetate (50 mL) and washed with NaHCO₃ sol. (1×), 1N HCl (1×) and brine (1×). The solution was dried (Na₂SO₄) filtered and concentrated in vacuo. The residue was purified by flash chromatography (55% ethyl acetate/hexanes) to afford the bromide as a colorless solid (2.0 g, 83%). m.p. 225°–230° C. FAB MS: 1050 (M+Na)⁺. ¹H NMR (250 MHz, CDCl₃) δ5.15 (dd,1H,J=9.0, 8.0 Hz); 4.90 (q, 2H, J=9.0 Hz); 4.85 (dd, 1H, J=9.0, 8.0 Hz); 4.95 (m, 3H); 4.3 (m, 1H); 4.1 (dd, 1H, J=12.0, 6.0 Hz); 3.75 (dd, 1H, J=8.0, 7.0 Hz); 3.7–3.40 (m, 7H); 3.35 (dd, 1H, J=8.0, 8.0 Hz); 3.1 (d, 1H, J=5.0 Hz); 2.5 (dd, 1H, J=8.0, 7.0 Hz); 2.4 (d, 1H, J=5.0 Hz); 2.35 (dd, 1H, J=13.0, 12.0 Hz); 2.15 (m, 1H); 2.1 (s, 3H); 2.09 (s, 3H); 2.06 (s, 3H); 2.03 (s, 6H); 2.0–1.1 (m, 21H); 1.05 (d, 3H, J=7.0 Hz); 1.02 (s, 3H); 0.85 (s, 3H); 0.77 (d, 3H, J=7.0 Hz).

Preparation V1

(3β,5α,25R)-3-[2',2'',3',3'',6'-penta-acetyl-6''-tert-butyl-dimethylsilyl-β-D-cellobiosyl)oxy]-spirostan-12-one Monosilylation Tert-butyl dimethyl silyl chloride (0.34 g, 2.28 mmol) was added to a solution of (3β,5α,25R)-3-[(2',2'',3',3'',6'- pentaacetyl-β-D-cellobiosyl)oxy]-spirostan-12-one (2.0 g, 2.07 mmol) in dry dimethyl formamide (10 mL) containing imidazole (280 mg, 4.14 mmol) and N,N-dimethyl 4-amino pyridine (100 mg). After 24 h, an additional 157 mg of tert-butyl dimethyl silyl chloride was added and the mixture stiffed another 24 hours. The mixture was diluted with ethyl acetate (50 mL) and washed with water (3×), 1N HCl (2×) and brine (1×), dried (Na₂SO₄) filtered and concentrated in vacuo to afford the title compound as a colorless foam (2.3 g, 100%). ¹H NMR (250 MHz, CDCl₃) δ5.12 (dd, 1H, J=9.0, 8.0 Hz); 5.05 (dd, 1H, J=9.0, 8.0 Hz); 4.8 (m, 2H); 4.5–3.3 (m, 15H); 2.5 (dd, 1H, J=8.0, 7.0 Hz); 2.4 (d, 1H, J=5.0 Hz); 2.35 (dd, 1H, J=13.0, 12.0 Hz); 2.16 (m, 1H); 2.1 (s, 3H); 2.08 (s, 3H); 2.02 (s, 9H); 2.0–1.1 (m, 20H); 1.05 (d, 3H, J=7.0 Hz); 1.02 (s, 3H); 0.88 (s, 9H); 0.85 (s, 3H); 0.77 (d, 3H, J=7.0 Hz); 0.02 (s, 6H).

Preparation W1

(3β,5α,25R)-3-[2',2",3',3",6'-penta-chloroacetyl-β-D-cellobiosyl)oxy]-spirostan-12-one

Paramethoxy Benzylidene Hydrolysis

Trifluoroacetic acid (19 mL) was added to a solution of (3β,5α,25R)-3-[(4",6"-[4-methoxybenzylidene]-2',2",3',3", 6'-penta-chloro-acetyl-β-D-cellobiosyl)oxy]-spirostan-12-one (23.7 g, 0.019 mol) in dichloromethane (150 mL) and methanol (50 mL). After 4 hours, the mixture was washed with water (3×) NaHCO₃ (2×) and brine (1×), dried (Na₂SO₄) filtered and concentrated. The residue was dissolved in a minimal amount of ethyl acetate and precipitated with hexanes. The solid was filtered and washed with hexanes and dried to afford 19.2 g product as a colorless solid (90%). m.p. 224–226. FAB MS: 1159 (M+Na)⁺. ¹H NMR (250 MHz, CDCl₃) δ5.2 (dd, 1H, J=9.0, 9.0 Hz); 5.1 (dd, 1H, J=9.0, 9.0 Hz); 4.95 (m, 2H); 4.6 (m, 3H); 4.2–3.4 (m, 21H); 3.35 (dd, 1H, J=9.0, 9.0 Hz); 3.1 (bs, 1H); 2.5 (dd, 1H, J=8.0, 7.0 Hz); 2.35 (dd, 1H, J=13.0, 12.0 Hz); 2.1 (m, 1H); 1.9–1.1 (m, 22H); 1.05 (d, 3H, J=7.0 Hz); 1.02 (s, 3H); 0.85 (s, 3H); 0.77 (d, 3H, J=7.0 Hz).

Preparation X1

(3β,5α,25R)-3-[(4",6"-[4-methoxybenzylidene]-2', 2",3',3",6'-penta-chloro-acetyl-β-D-cellobiosyl)oxy]-spirostan-12-one

Paramethoxybenzylidene Formation and Chloroacetylation

Camphorsulfonic acid (3 g) was added to a mixture of (3β,5α,25R)-3-[(β-D-cellobiosyl)oxy]-spirostan-12-one (50 g, 0.066 mol) and anisaldehyde dimethyl acetal (50 mL, 0.29 mol) in 1,2-dichloroethane (1500 mL). The suspension was heated to reflux temperature and 200 mL of solvent was distilled off. After 4 hours at reflux temperature, the gelatinous mixture was cooled to 0° C. and treated with pyridine (160 mL, 1.99 mol) and chloroacetic arthydride (170 g, 1 mmol). The reaction was allowed to warm to room temperature and after 2 hours, the mixture was washed with 1N HCl (3×), NaHCO₃ (1×) and brine (1×), dried (Na₂SO₄), filtered and concentrated in vacuo. The residue was dissolved in a minimum amount of ethyl acetate and the product was precipitated with hexanes. The solid was filtered, washed with hexanes and dried to afford 78.7 g of product as a colorless solid (95%). m.p. 249–251. FAB MS: 1277 (M+Na)⁺. ¹H NMR (250 MHz, CDCl₃) δ7.35 (d, 2H, J=9.0 Hz); 6.88 (d, 2H, J=9.0 Hz); 5.45 (s, 1H); 5.3 (m, 2H); 5.0 (m, 2H); 4.7 (d, 1H, J=7.0 Hz); 4.6 (m, 2H); 4.3 (m, 2H); 4.2 (dd, 1H, J=11.0, 6.0 Hz); 4.2–3.5 (m, 14H); 3.8 (s, 3H); 3.35 (dd, 1H, J=11.0, 10.0 Hz); 2.5 (dd, 1H, J=8.0, 7.0 Hz); 2.35 (dd, 1H, J=13.0, 12.0 Hz); 2.1 (m, 1H); 2.1–1.0 (m, 25H); 1.05 (d, 3H, J=7.0 Hz); 1.02 (s, 3H); 0.85 (s, 3H); 0.77 (d, 3H, J=7.0 Hz).

Preparation Y1

(3β,5α,25R)-3-[(2',2",3',3",6'-pentaacetyl-β-D-cellobiosyl)oxy]spirostan-12-one

Benzylidene Hydrolysis (3β,5α,25R)-3-[(4",6"-benzylidene-pentaacetyl-β-D-cellobiosyl)oxy]spirostane-12-one (0.75 g, 0.712 mol) was added to glacial acetic acid (8 mL) and water (2 mL). The reaction was heated to 80° C. and stirred for 2 hours under nitrogen atmosphere. Upon completion, the reaction was cooled and then was added to ice. The organic material was extracted with ethyl acetate (75 mL), then washed with water (2×), saturated sodium bicarbonate solution (2×), and brine (1×). The organic layer was dried over sodium sulfate, filtered and concentrated in vacuo. The residual material was triturated with hexanes, filtered, washed with hexanes and dried to afford 670 mg (98%) of product as a colorless solid. ¹HNMR (250 MHz, CDCl₃) δ5.25–3.3 (m, 19H); 2.95 (d, 1H, J=7 Hz); 2.6–1.1 (m, 40H); 1.0 (s, 3H); 0.90 (d, 3H, J=7 Hz); 0.8 (d, 3H, J=7 Hz); 0.7 (s, 3H). m.p. 248°–250.7° C.

In an analogous manner the following compounds, Preparation Y2–Y5, were prepared from the appropriate starting material using the above general procedure.

Preparation Y2

(3β,5α,25R)-3-[(2',2",3',3",6'-pentaacetyl-β-D-cellobiosyl)oxy]spirostane

Preparation Y3

(3β,5α,25R)-3-[(2',2",3',3",6'-penta-acetyl-β-D-lactosyl)oxy]-spirostan-12-one

Preparation Y4

(3β,25R)-3-[(2',2",3',3",6'-penta-acetyl-β-D-cellobiosyl)oxy]-5-spirostene

Preparation Y5

(3β,5α,25R)-3-[(2',2",3',3",6'-penta-acetyl-β-D-cellobiosyl)oxy]-12-acetoxy-spirostane

Preparation Z1

(3β,5α,25R)-3-[(4",6"-benzylidene-pentaacetyl-β-D-cellobiosyl)oxy]spirostan-12-one

Benzylidene Formation and Acetylation

A mixture of (3β,5α,25R)-3-[(β-D-cellobiosyl)oxy] spirostan-12-one (0.75 g, 1.00 mmol), camphorsulphonic acid (35 mg), chloroform (25 mL) and benzaldehyde dimethyl acetal (0.50 mL) was heated to reflux temperature under nitrogen atmosphere. The reaction was stirred at reflux temperature for 3 hours. Upon formation of the benzylidene, the reaction was cooled in an ice bath and pyridine (1.60 mL, 20 mmol), dimethylaminopyridine (1.00 g) and acetic anhydride (1.40 mL, 15 mmol) were added. The reaction was warmed to room temperature and stirred for 2 hours. The reaction mixture was then washed with water once. The reaction was partially concentrated in vacuo to remove most of the chloroform. The remaining material was diluted with ethyl acetate, washed with 1N hydrochloric acid solution (2×), saturated sodium bicarbonate solution (1×), water (1×) and brine (1×). The organic layer was then dried over sodium sulfate, filtered and concentrated in vacuo. The residual material was triturated with hexanes, filtered, washed with hexanes and dried to afford 0.88 g (83% yield) of product as a colorless solid.

$^1$HNMR (250 MHz, CDCl$_3$) δ7.45–7.3 (m, 5H); 5.5 (s, 1H); 5.3–3.3 (m, 18H); 2.5–1.05 (m, 40H); 1.0 (s, 3H); 0.90 (d, 3H, J=7 Hz); 0.8 (d, 3H, J=7 Hz); 0.7 (s, 3H).

In an analogous manner the following compounds, Preparation Z2–Z5, were prepared from the appropriate starting material using the above general procedure.

Preparation Z2

(3β,5α,25R)-3-[(4",6"-benzylidene-pentaacetyl-β-D-cellobiosyl)oxy]spirostane

Preparation Z3

(3β,5α,25R)-3-[(4",6"-benzylidene-2',2",3',3",6'-penta-acetyl-β-D-lactosyl)oxy]-spirostan-12-one

Preparation Z4

(3β,25R)-3-[(4",6"-benzylidene-2',2",3',3",6'-penta-acetyl-β-D-cellobiosyl)oxy]-5-spirostene

Preparation Z5

(3β,5α,12β,25R)-3-[(4",6"-benzylidene-2',2",3',3", 6'-penta-acetyl-β-D-cellobiosyl)oxy]-12-acetoxy-spirostane

Preparation AA1

(3β,5α,25R)-3-[(2',2",3',3",4"-pentaacetyl-β-D-cellobiosyl)oxy]spirostan-12-one

Desilylation

A mixture of (3β,5α,25R)-3-[(6',6"-bis-[t-butyldiphenylsilyl]-pentaacetyl-β-D-cellobiosyl)oxy]spirostan-12-one (7.44 g, 4.96 mol) and pyridine (35 mL) was cooled to 0° C. under nitrogen atmosphere. Hydrogen fluoride in pyridine (35 mL) was added and the reaction was gradually warmed to room temperature and allowed to stir for 3 hours. Upon completion, the reaction was cooled and quenched with water. The quenched mixture was dissolved in ethyl acetate, washed with water (1×), 1N hydrochloric acid (4×), brine (1×), dried over sodium sulfate, filtered and concentrated in vacuo. The residual material was triturated with hexanes, filtered, washed with hexanes and dried to afford 3.55 g (74.2%) of product. $^1$HNMR (250 MHz, CDCl$_3$) δ5.25–3.3 (m, 20H); 2.65–1.05 (m, 40H); 1.0 (s, 3H); 0.95 (d, 3H, J=8 Hz); 0.8 (d, 3H, J=8 Hz); 0.7 (s, 3H). FAB MS: 965 (M+H)$^+$. m.p. 232°–233° C.

In an analogous manner the following compounds, Preparations AA2–AA3, were prepared from the appropriate starting material using the above general procedure.

Preparation AA2

(3β,5α,25R)-3-[(2',2",3',3",4"-pentaacetyl-β-D-cellobiosyl)oxy]spirostan-12-one

Preparation AA3

(3β,5α,25R)-3-[(2',2",3',3",4"-pentaacetyl-β-D-cellobiosyl)oxy]spirostane

Preparation BB1

(3β,5α,25R)-3-[(6',6"-di-t-butyldiphenylsilyl-pentaacetyl-β-D-cellobiosyl)oxy]spirostan-12-one

Silylation and Acetylation

A mixture of (3β,5α,25R)-3-[(β-D-cellobiosyl)]oxy] spirostan-12-one (17 g, 0.023 mol), imidazole (10.7 g, 0.158 mol), dimethylaminopyridine (5 g) and N,N-dimethylformamide (300 mL) was cooled to 0° C. under nitrogen atmosphere. Tert-butyldiphenylsilyl chloride (23.4 mL, 0.09 mol) was added, the mixture was warmed to room temperature and stirred for 5 hours. Pyridine (35 mL, 0.45 mol) and acetic anhydride (32 mL ,0.338) mol) were added and the reaction was stirred overnight. The reaction was then partitioned between ethyl acetate (750 mL) and water (500 mL). The layers were separated and the aqueous layer was reextracted with ethyl acetate (1×100 mL). The combined organic layers were washed with water (2×300 mL), 1N hydrochloric acid solution (3×300 mL), brine (1×300 mL), dried over sodium sulfate, filtered and concentrated in vacuo. The crude product was flash chromatographed (5 to 30% ethyl acetate/hexanes) to afford 30.5 g (94% yield) of product as a solid foam. $^1$HNMR (250 MHz, CDCl$_3$) δ7.85–7.3 (m, 20H); 5.3–3.3 (m, 18H); 2.6–1.0 (m, 61H); 0.90 (d, 3H, J=7 Hz); 0.8 (d, 3H, J=7 Hz); 0.7 (s, 3H). MS: 1441 (M+Na)$^+$.

In an analogous manner the following compounds, Preparations BB2–BB3, were prepared from the appropriate starting material using the above general procedure.

Preparation BB2

(3β,5α,25R)-3-[(6',6"-bis-(t-butyldiphenylsilyl)-pentaacetyl-β-D-lactosyl)oxy]spirostan-12-one

Preparation BB3

(3β,5α,25R)-3-[(6',6"-bis-(t-butyldiphenylsilyl)-pentaacetyl-β-D-cellobiosyl)oxy]spirostane

Preparation CC1

(3β,5α,25R)-3-[(β-D-cellobiosyl)oxy]spirostan-12-one

Deacylation

Sodium methoxide (50 mg) was added to a solution of (3β,5α,25R)-3-[(heptaacetyl-β-D-cellobiosyl)oxy] spirostan-12-one (5 g, 4.77 mmol) in THF (75 mL) and methanol (25 mL). The solution was heated to a gentle reflux for 1 hour as a precipitate formed. The mixture was cooled, and concentrated to 25 mL. Methanol (10 mL) and water (10 mL) were added and the precipitate was collected by vacuum filtration and washed with 1:1 methanol:water. The product was dried in a vacuum oven (80° C.) to afford 2.9 g (80%) of the title compound as a colorless solid. m.p. >250° C. FAB MS: 755 (M+H)$^+$. Analysis calc. for $C_{39}H_{62}O_{14}+2H_2O$: C 59.22 H 8.41. Found C 59.54 H 8.64.

In an analogous manner, the following compounds, Preparations CC2–CC7, were prepared from the appropriate starting material using the above general procedure.

Preparation CC2

(3β,5α,25R)-3-[(β-D-lactosyl)oxy]-spirostan-12-one

Preparation CC3

(3β,25R)-3-[(β-D-cellobiosyl)oxy]-5-spirostene

Preparation CC4

(3β,5α,12β,25R)-3-[(β-D-cellobiosyl)oxy]-12-hydroxy-spirostane

Preparation CC5

(3β,5α,25R)-3-[(β-D-cellobiosyl)oxy]-spirostane

Preparation CC6

(3β,5β,25R)-3-[(β-D-cellobiosyl)oxy]-spirostane

Preparation CC7

(3β,5β,25S)-3-[(β-D-cellobiosyl)oxy]-spirostane

Preparation DD (3β,5α,25R)-3-[(Heptaacetyl-α-D-cellobiosyl)oxy]-spirostane

Anomerization

To a solution of (3β,5α,25R)-3-[(heptaacetyl-β-D-cellobiosyl)oxy]spirostane (5.50 g, 5.31 mmol) in methylene chloride (90 mL), a 30% solution of HBr in acetic acid (3.2 mL) was added. The reaction mixture was stirred at room temperature under nitrogen for 67 hours. The reaction was then quenched by the slow addition of saturated sodium bicarbonate solution (60 mL). The organic layer was separated, dried over magnesium sulfate and concentrated in vacuo to afford a yellow solid. The crude product was purified by flash chromatography (50% ethyl acetate/hexanes) to afford 2.378 g of product. This product was purified further by flash chromatography (50% ethyl acetate/hexanes) to afford 1.399 g (25.4% yield) of the title compound. MS (m/e): 1035 (M+H)$^+$, 1057 (M+Na)$^+$. $^1$H NMR (300 MHz, CDCl$_3$) δ5.45–3.2 (m, 18H), 2.4 (m, 2H), 2.2–1.9 (m, 21H), 1.8–0.4 (m, 37H), 0.95 (d, 3H, J=7), 0.9 (s, 3H), 0.8 (s, 3H), 0.6 (d, 3H, J=7).

Preparation EE1

(3β,5α,25R)-3-[(Heptaacetyl-β-D-cellobiosyl)oxy] spirostan-12-one

Zinc Fluoride Promoted Coupling of Free Spirostane

A suspension of (3β,5α,25R)-3-hydroxyspirostan-12-one (3.0 g, 6.97 mmol) and anhydrous zinc fluoride (2.88 g, 27.9 mmol) in dry acetonitrile (175 mL) was dried by removal of 75 mL of acetonitrile by distillation. The suspension was allowed to cool, heptaacetyl-β-D-cellobiosyl bromide (9.75 g, 13.9 mmol) was added and the resulting suspension was heated to 65° C. for 3 hours. After cooling to room temperature, methylene chloride (150 mL) was added, the suspension was stirred for 10 minutes and filtered. The filtrate was concentrated in vacuo to give 10 g of crude product. This material was dissolved in 8:2 chloroform:methanol, preadsorbed on silica gel and purified by flash chromatography (eluent: 1:1 ethyl acetate:hexane followed by pure ethyl acetate) to give 6.81 g (93% yield) of the title material. FAB MS: 1049 (M+H)$^+$. m.p. 220°–221° C. Analysis calc. for $C_{53}H_{76}O_{21}+0.5H_2O$: C 60.11, H 7.34. Found: C 59.90 H 7.24.

In an analogous manner, the following compounds, Preparations EE2–EE7, were prepared from the appropriate starting material using the above general procedure.

Preparation EE2

(3β,5α,25R)-3-[(Heptaacetyl-β-D-lactosyl)oxy]-spirostan-12-one

Preparation EE3

(3β,25R)-3-[(Heptaacetyl-β-D-cellobiosyl)oxy]-5-spirostene

Preparation EE4

(3β,5α,12β,25R)-3-[(Heptaacetyl-β-D-cellobiosyl)oxy]-12-hydroxy-spirostane

Preparation EE5

(3β,5α,25R)-3-[(Heptaacetyl-β-D-cellobiosyl)oxy]-spirostane

Preparation EE6

(3β,5β,25R)-3-[(Heptaacetyl-β-D-cellobiosyl)oxy]-spirostane

Preparation EE7

(3β,5β,25S)-3-[(Heptaacetyl-β-D-cellobiosyl)oxy]-spirostane

Preparation FF (3β,5α,25R)-3-([(heptaacetyl-β-D-maltosyl)oxy] spirostane

Mercuris Bromide/Mercuric Cyanide Promoted Coupling of Silylated Spirostane

Powdered 4A molecular sieves (1 g) were added to a solution of trimethylsilyl tigogenin (1.17 g, 2.4 mmol) and acetobromo maltose (3.36 g, 4.8 mmol) in $CH_2Cl_2$ (15 mL) and $CH_3CN$ (5 mL) at room temperature. After stirring for 15 minutes $Hg(CN)_2$ (2.4 g, 9.6 mmol) and $HgBr_2$ (3.4 g, 9.6 mmol) were added and the mixture stirred at room temperature for three hours. The mixture was diluted with ethyl acetate (50 mL) and filtered. The filtrate was washed with 1N HCl(3×30 mL) and brine (1×30 mL), dried ($Na_2SO_4$) filtered and concentrated in vacuo. The product was purified by flash chromatography (10–20% $EtOAc/CH_2Cl_2$) to afford 400 mg product as a colorless solid. MS 489 $(M+H)^+$. $^1H$ NMR (250 MHz, $CDCl_3$) δ5.35(d, 1H, J=1.0 Hz); 5.2 (dd, 1H, J=4.5, 4.5 Hz); 5.15 (dd, 1H, J=6.0, 5.0 Hz); 4.95 (dd, 1H, J=4.5, 1.0 Hz); 4.65 (dd, 1H, J=5.0, 4.5 Hz); 4.55 (d, 1H, J=6.0 Hz); 4.4 (m, 3H); 4.1 (m, 3H); 3.85 (t, 1H, J=3.0 Hz); 3.8 (t, 1H, J=4.5 Hz); 3.5 (m, 3H); 3.35 (t, 1H, J=5.0 Hz); 2.15 (s, 3H); 2.12 (s, 3H); 2.07 (s, 12H); 2.0 (s, 3H); 2.0–0.5 (m, 27H); 0.98 (d, 3H, J=4.0 Hz); 0.82 (s, 3H); 0.8 (d, 3H, J=4.0 Hz); 0.73 (s, 3H).

Preparation GG (3β,5α,25R)-3-trimethylsilyloxyspirostane

Silylation of Spirostanes

Trimethylsilyl trifluoromethanesulfonate (4 mL, 22.1 mmol) was added dropwise to a solution of tigogenin (6 g, 14.4 mmol) and triethyl amine (6 mL, 45 mmol) in $CH_2Cl_2$ (50 mL) at 0° C. After 1 hour, the mixture was diluted with ether (100 mL) and washed with saturated $NaHCO_3$ solution (2×50 mL) and brine (1×50 mL), dried ($Na_2SO_4$) filtered and concentrated in vacuo. Upon addition of methanol, a precipitate formed which was filtered and washed with methanol and dried to afford 6.2 g product as a colorless solid. MP 197°–198° C. MS 489 $(M+H)^+$. $^1H$ NMR (250 MHz, $CDCl_3$) δ4.35 (q, 1H, J=3.0 Hz); 3.5 (m, 2H); 3.4 (t, 1H, J=5.5 Hz); 2.0–0.5 (m, 27H); 1.0 (d, 3H, J=4.0 Hz); 0.85 (s, 3H); 0.8 (d, 3H, J=4.0 Hz); 0.75 (s, 3H); 0.1 (s, 9H).

Preparation HH (3β,5α,12α,25R)spirostan-3,12-diol (3β,5α,12α,25R)spirostan-3,12-diol: Using the procedure described in *J. Am. Chem. Soc.*, 1954, 76, 4013, (3β,5α, 25R)-spirostan-3-ol-12-one was reduced with lithium aluminum hydride in ether to give a mixture of C-12 alcohols from which the title compound was isolated.

Preparation II 1-(2-thienyl)-ethyl amine hydrochloride

Methoxylamine hydochloride (5 g, 60 mmol) and pyridine (9.5 mL, 120 mmol) were added to a solution of 2-aceyl thiophene (5 g, 40 mmol) in methanol (25 mL) at room temperature. After 3 hours, the mixture was concentrated in vacuo, diluted with ethyl acetate (100 mL) and washed with 1N HCl (3×) and brine (1×), dried ($Na_2SO_4$), filtered and concentrated in vacuo to give a mixture of oxime isomers.

Trifluoroacetic acid (4.9 mL, 65 mmol) was added dropwise to a suspension of sodium borohydride (2.4 g, 65 mmol) in THF (40 mL) at 0° C. A solution of the oxime prepared above (2.0 g, 13 mmol) in THF (5 mL) was then added dropwise. After 2 h, the reaction was heated to a gentle reflux for 2 h, cooled, and quenched by the addition of water (10 mL). The mixture was diluted with methylene chloride (50 mL) and washed with brine (2×) and dried ($MgSO_4$) filtered and concentrated in vacuo. The residue was dissolved in 100 mL of diethyl ether and treated with sat HCl in ether (3 mL). The precipitate was collected by vacuum filtration and washed with ether and dried to afford the title amine as a colorless solid as its hydrochloride salt (950 mg). $^1H$ NMR (250 MHz, d6 DMSO) δ8.7 (bs, 3H); 7.53 (d, 1H, J=4.0 Hz); 7.3 (d, 1H, J=2.0 Hz); 7.05 (dd, 1H, J=4.0, 2.0 Hz); 4.65 (m, 2H); 1.58 (d, 3H, J=7.0 Hz).

Preparation JJ trans-2-hydroxy-cyclopentyl methyl amine

Nitrile Reduction

A solution of trans-2-cyano-cyclopentanol (1.23 g, 11.1 mmol) in THF (10 mL) was added dropwise to a suspension of lithium aluminum hydride (422 mg, 11.1 mmol) in THF (20 mL) at –15° C. After 1.5 hours the reaction warmed to room temperature and then heated to a gentle reflux for 1 hour. The reaction was cooled, and quenched by the sequential addition of $H_2O$ (0.42 mL), 15% NaOH (0.42 mL) and $H_2O$ (1.3 mL). The mixture was diluted with ether (50 mL), dried ($MgSO_4$) filtered and concentrated to give 0.71 g product as an oil. $^1H$ NMR (300 MHz, $CDCl_3$) δ3.9 (q, 1H, J=6.0 Hz); 3.0 (dd, 1H, J=11.0, 4.0 Hz); 2.5 (dd, 1H, J=11.0, 8.0 Hz); 2.0–1.5 (m, 7H); 1.1 (m, 1H).

Preparation KK trans-2-cyano-cyclopentanol

Cyanide Opening of Epoxide

Potassium cyanide (9.65 g, 0.148 mol) and ammonium chloride (7.12 g, 0.131 mol) were added to a solution of cyclopentene oxide (5.0 g, 0.059 mol) in methanol (134 mL) and water (36 mL). The mixture was heated to a gentle reflux for 6 hours then stirred at room temperature overnight. The mixture was concentrated to 50 mL, diluted with ethyl acetate (100 mL) and washed with water (3×), and brine (1×), dried ($Na_2SO_4$), filtered and concentrated in vacuo to afford the alcohol as a brown liquid (1.07 g) which was used without further purification. $^1$H NMR (250 MHz, CDCl$_3$) δ4.52 (q, 1H, J=6.0 Hz); 2.72 (m, 1H); 2.3–1.6 (m, 7H).

Preparation LL

Thiazol-2-yl-methylamine

Azide Reduction

Triphenylphosphine (2.08 g, 7.9 mmol) was added to a solution of thiazol-2-yl-methylazide (1.11 g, 7.9 mmol) in THF (20 mL). After 1 hour, H$_2$O (214 μL) and ammonium hydroxide sol (0.5 mL) were added. The reaction stirred overnight, was concentrated in vacuo, and purified by flash chromatography (5% methanol/methylene chloride) to afford 645 mg of the title product as a tan oil (72%).

$^1$H NMR (250 MHz, CDCl$_3$) δ7.7 (d, 1H, J=2.0 Hz); 7.25 (d, 1H, J=2.0 Hz); 4.2 (s, 2H); 1.7 (bs, 2H).

Preparation MM

2-azidomethyl thiazole

Diphenylphosphoryl azide (3.25 mL, 0.015 mol) and 1,8-diazabicyclo[5.4.0] undec-7-ene (2.25 mL, 0.025 mol) were added to a solution of thiazol-2-yl-methanol (1.44 g, 0.013 mol) in toluene (20 mL) at 0° C. After 1 hour, the reaction was warmed to room temperature and stirred overnight. The mixture was diluted with toluene (20 mL) and washed with H$_2$O (3×) brine (1×), dried (Na$_2$SO$_4$), filtered and concentrated in vacuo. The residue was purified by flash chromatography (30% ethyl acetate/hexanes) to afford the azide as a tan oil (1.1 g, 63%). IR: 2098 cm$^{-1}$.

$^1$H NMR (250 MHz, CDCl$_3$) δ7.8 (d, 1H, J=2.0 Hz); 7.4 (d, 1H, J=2.0 Hz); 4.7 (s, 2H).

Preparation NN1

Methyl-(3-amino-2,2-dimethyl) propionate hydrochloride

Raney nickel (2 g) was washed with water then methanol and added to a solution of methyl 2,2-dimethyl cycano acetate (2.0 g, 0.016 mol) in methanol (75 mL). The mixture was shaken under 40 psi of hydrogen in a Parr apparatus. After 3 hours, the reaction was purged with nitrogen. The catalyst was removed by filtration and the filtrate was acidified by the addition of sat HCl/ether (5 mL). The solution was concentrated to ~5 mL and added to 200 mL of vigorously stirred ether. The resulting solid was collected by vacuum filtration, washed with ether and dried to afford 1.25 g of amine hydrochloride as a colorless solid. m.p. 168°–170° C. $^1$H NMR (250 MHz, CDCl$_3$) δ8.3 (bs, 3H); 3.6 (s, 3H); 2.92 (m, 2H); 1.2 (s, 6H).

In an analogous manner, the following compounds, Preparation NN2–NN3 were prepared from the appropriate starting material using the above general procedure.

Preparation NN2

Methyl-(2-aminomethyl) butyrate hydrochloride

Preparation NN3

1-methoxycarbonyl-1-aminomethyl cyclopropane hydrochloride

Preparation OO1

Trans-2-ethoxycarbonyl-cyclopropyl isocyanate

Diphenylphosphoryl azide (0.54 mL, 2.53 mmol) and triethyl amine (0.35 mL, 2.53 mmol) were added dropwise to a solution of trans-2-ethoxycarbonyl-cyclopropane carboxylic acid (0.4 g, 2.53 mol) in toluene (5 mL) at room temperature. After 1 hour, the mixture was diluted with toluene (10 mL), washed with water (1×), 0.1N HCl (1×) and brine (1×), and dried (Na$_2$SO$_4$). The solution of trans-2-carboethoxy-cyclopropane carbonyl azide was heated at 100° C. for 1 hour producing a solution of the title compound which was used as is.

In an analogous manner, the following compound, Preparation OO2 was prepared from the appropriate starting material using the above general procedure.

Preparation OO2

3-oxo-butyl-isocyanate

I claim:
1. A spirostanyl glycoside compound of Formula I and the pharmaceutically-acceptable salts and hydrates thereof
wherein
Q$^1$ is carbonyl, methylene, R$_1$, R$_2$, and R$_3$ are each independently hydrogen, hydroxy, halo, amino, azido, (C$_1$–C$_6$)alkoxy(C$_1$–C$_6$)alkoxy or —Z—R$_4$;

Z for each occurrence is independently —NH—C (=O)—, —O—C(=O)—N(R$^5$)—, —NH—C(=O)—N(R$^5$)— or —O—C(=S)—N(R$^5$)—;

R$_4$ for each occurrence is independently aryl, aryl(C$_1$–C$_6$) alkyl, (C$_2$–C$_4$)alkenyl, (C$_1$–C$_6$)alkyl, cyclo(C$_3$–C$_7$) alkyl or cyclo(C$_3$–C$_7$)alkyl(C$_1$–C$_6$)alkyl; each R$_4$ optionally mono-, di-, or tri-substituted independently with halo, (C$_1$–C$_4$)alkyl, hydroxy, phenoxy, trifluoromethyl, nitro, (C$_1$–C$_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, dimethylamino, mono- or di-($C_1$-$C_4$)alkylaminocarbonyl, ($C_1$-$C_4$)alkylcarbonyl, ($C_1$-$C_4$)alkoxycarbonyl, pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and $R_5$ for each occurrence is independently hydrogen, ($C_1$-$C_4$)alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with ($C_1$-$C_4$)alkoxycarbonyl;

with the proviso that $R_1$, $R_2$ and $R_3$ are not all hydroxy.

2. A compound according to claim 1 wherein $R_1$, $R_2$ and $R_3$ are each independently hydroxy or —Z—$R_4$, Z is —O—C(=O)—N($R_5$)— and $R_5$ is hydrogen.

3. A compound according to claim 2 wherein the $C^{1'}$ anomeric oxy is beta, the $C^{1''}$ anomeric oxy is beta, $R_3$ is alpha, the $C^5$ hydrogen is alpha, $C^{25}$ is (R), the $C^3$ oxy is beta, $Q^1$ is carbonyl and $R_1$ is hydroxy.

4. A compound according to claim 3 wherein $R_2$ and $R_3$ are —Z—$R_4$ and $R_4$ is 2,4-difluorophenyl.

5. A compound according to claim 3 wherein $R_3$ is hydroxy, $R_2$ is —Z—$R_4$ and $R_4$ is 2,4-difluorophenyl.

6. A compound according to claim 3 wherein $R_2$ and $R_3$ are —Z—$R_4$ and $R_4$ is phenyl.

7. A compound according to claim 3 wherein $R_2$ and $R_3$ are —Z—$R_4$ and $R_4$ is 2-fluorophenyl.

8. A compound according to claim 3 wherein $R_2$ and $R_3$ are —Z—$R_4$ and $R_4$ is 2-methylphenyl.

9. A compound according to claim 3 wherein $R_3$ is hydroxy, $R_2$ is —Z—$R_4$ and $R_4$ is 2,6-dichlorophenyl.

10. A compound according to claim 3 wherein $R_2$ and $R_3$ are Z—$R_4$ and $R_4$ is 2-thienyl-methyl.

11. A compound according to claim 3 wherein $R_2$ and $R_3$ are Z—$R_4$ and $R_4$ is 2-methoxycarbonyl-ethyl.

12. A compound according to claim 3 wherein $R_2$ and $R_3$ are Z—$R_4$ and $R_4$ is thiazol-2-yl-methyl.

13. A compound according to claim 3 wherein $R_2$ and $R_3$ are Z—$R_4$ and $R_4$ is 2-methoxycarbonyl-butyl.

14. A compound according to claim 1 wherein $Q^1$ is carbonyl, $R_1$ is hydroxy, hydrogen, halo, azido, or ($C_1$-$C_6$)alkoxy($C_1$-$C_6$)alkoxy, $R_2$ is hydrogen, halo, azido or ($C_1$-$C_6$)alkoxy($C_1$-$C_6$)alkoxy, $R_3$ is —Z—$R_4$, Z is —O—C(=O)N—($R_5$)—, and $R_5$ is hydrogen.

15. A compound according to claim 14 wherein the $C^{1'}$ anomeric oxy is beta, the $C^{1''}$ anomeric oxy is beta, $R_3$ is alpha, the $C^5$ hydrogen is alpha, $C^{25}$ is (R), and the $C^3$ oxy is beta.

16. A compound according to claim 15 wherein $R_1$ is hydroxy, $R_2$ is hydrogen and $R_4$ is 2-fluorophenyl.

17. A compound according to claim 1 wherein $Q^1$ is carbonyl, $R_3$ is hydroxy, at least one of $R_1$ and $R_2$ is —Z—$R_4$, Z is —NH—C(=O)— and $R_4$ for each occurrence is independently ($C_1$-$C_6$)alkyl.

18. A compound according to claim 1 wherein $Q^1$ is carbonyl, $R_3$ is hydroxy and $R_1$ and $R_2$ are each independently halo or azido.

19. A method of treating hypercholesterolemia which comprises administering to a mammal in need of such treatment a therapeutically effective amount of a compound of claim 1.

20. A pharmaceutical composition for treatment of hypercholesterolemia in mammals which comprises a therapeutically effective amount of compound of claim 1 and a pharmaceutically acceptable carrier.

21. A method of treating atherosclerosis which comprises administering to a mammal in need of such treatment a therapeutically effective amount of a compound of claim 1.

22. A pharmaceutical composition for treatment of atherosclerosis in mammals which comprises a therapeutically effective amount of compound of claim 1 and a pharmaceutically acceptable carrier.

23. A process for preparing a compound of Formula IA

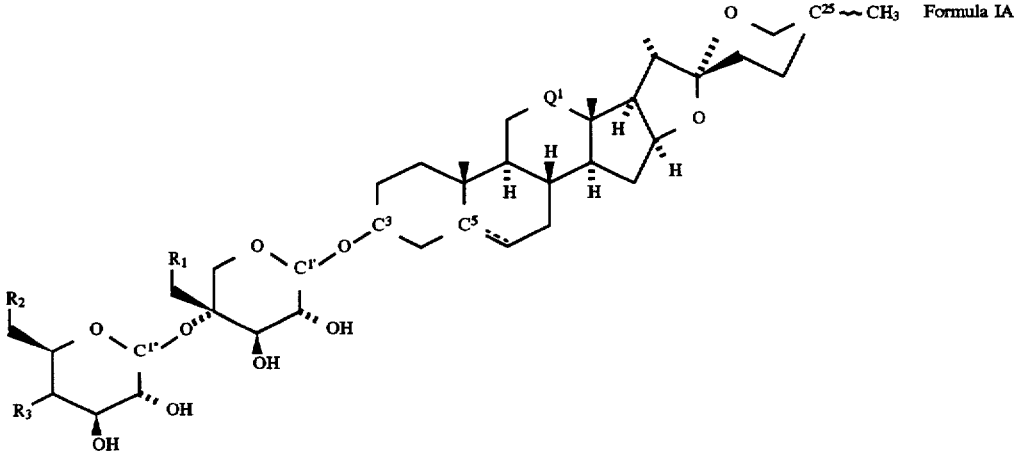

and the pharmaceutically-acceptable salts and hydrates thereof wherein $Q^1$ is carbonyl, methylene,

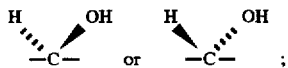

$R_1$, $R_2$ and $R_3$ are each independently hydrogen, hydroxy, halo, amino, azido, ($C_1$-$C_6$)alkoxy($C_1$-$C_6$)alkoxy or —Z—$R_4$;

Z for each occurrence is independently —NH—C(=O)—, —O—C(=O)—N($R^5$)—, —NH—C(=O)—N($R^5$)— or —O—C(=S)—N($R^5$)—;

$R_4$ for each occurrence is independently aryl, aryl($C_1$-$C_6$)alkyl, ($C_2$-$C_4$)alkenyl, ($C_1$-$C_6$)alkyl, cyclo($C_3$-$C_7$)alkyl or cyclo($C_3$-$C_7$)alkyl($C_1$-$C_6$)alkyl; each $R_4$ optionally mono-, di-, or tri-substituted independently with halo, ($C_1$-$C_4$)alkyl, hydroxy, phenoxy, trifluoromethyl, nitro, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkylsulfonyl, dimethylamino, mono -or di-($C_1$-$C_4$)alkylaminocarbonyl, ($C_1$-$C_4$)alkylcarbonyl, ($C_1$-$C_4$)alkoxycarbonyl, pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and $R_5$ for each occurrence is independently hydrogen, ($C_1$-$C_4$)alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with ($C_1$-$C_4$)alkoxycarbonyl;

with the proviso that $R_1$, $R_2$ and $R_3$ are not all hydroxy which process comprises deprotecting a compound of Formula IID optionally mono-, di-, or tri-substituted independently with halo, ($C_1$-$C_4$)alkyl, hydroxy, phenoxy, trifluoromethyl, nitro, ($C_1$-$C_4$)alkoxy, methylenedioxy, oxo, ($C_1$-$C_4$)alkylsulfanyl, ($C_1$-$C_4$)alkylsulfinyl, ($C_1$-$C_4$)alkyisulfinyl, dimethylamino, mono-or di-($C_1$-$C_4$)alkylaminocarbonyl, ($C_1$-$C_4$)alkylcarbonyl, ($C_1$-$C_4$)alkoxycarbonyl, pyrrolidinylcarbonyl wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl; and $R_5$ for each occurrence is independently hydrogen, ($C_1$-$C_4$)alkyl or $R_5$ is such that when taken together with the nitrogen to which it is attached and with $R_4$, wherein $R_4$ is a covalent bond, it forms pyrrolidinyl, piperidinyl, N-methylpiperazinyl, indolinyl or morpholinyl and such cyclic group may be substituted on carbon with ($C_1$-$C_4$)alkoxycarbonyl.

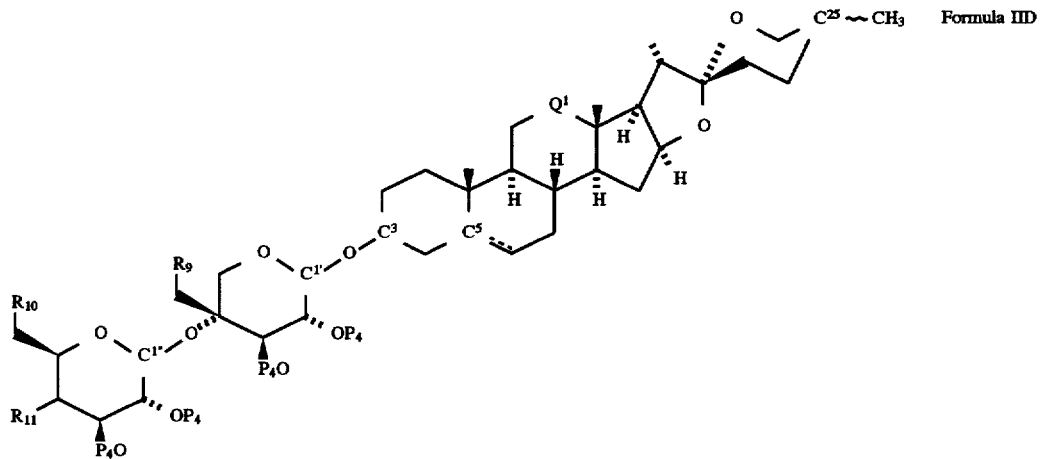

Formula IID wherein $Q^1$ is carbonyl, methylene,

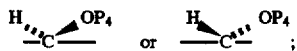

$P^4$ is an alcohol protecting group;

$R_9$, $R_{10}$ and $R_{11}$ are each independently, hydrogen, hydroxy, halo, amino, azido, ($C_1$-$C_6$)alkoxy($C_1$-$C_6$)alkoxy, —Z—$R_4$ or an alcohol protecting group attached through an oxy;

Z for each occurrence is independently —NH—C(=O)—, —O—C(=O)—, —O—C(=O)—N($R^5$)—, —NH—C(=O)—N($R^5$)— or —O—C(=S)—N($R^5$)—;

$R_4$ for each occurrence is independently aryl, aryl($C_1$-$C_6$)alkyl, ($C_2$-$C_4$)alkenyl, ($C_1$-$C_6$)alkyl, cyclo($C_3$-$C_7$)alkyl or cyclo($C_3$-$C_7$)alkyl($C_1$-$C_6$)alkyl; each $R_4$ 24. The process according to claim 23 wherein $R_{10}$ and $R_{11}$ are each —O—C(=O)—N($R_5$)—$R_4$, $R_9$ is an alcohol protecting group attached through an oxy, $R_5$ is hydrogen and the Formula IID compound is deprotected by reaction with a nucleophilic base in a polar solvent at temperatures of about 0° C. to about 100° C.

25. The process according to claim 24 wherein the $C^{1'}$ anomeric oxy is beta, the $C^{1''}$ anomeric oxy is beta, $R_{11}$ is alpha, the $C^5$ hydrogen is alpha, $C^{25}$ is (R), the $C^3$ oxy is beta, $Q^1$ is carbonyl and the alcohol protecting group is acetyl or chloroacetyl.

26. The process according to claim 25 wherein $R_4$ is 2,4-difluorophenyl, phenyl, 2-fluorophenyl, 2-methylphenyl, 2-thienyl-methyl, 2-methoxycarbonyl-ethyl, thiazol-2-yl-methyl or 2-methoxycarbonyl-butyl.

* * * * *